(12) United States Patent
Vitaliano et al.

(10) Patent No.: US 7,393,924 B2
(45) Date of Patent: Jul. 1, 2008

(54) SMART BIO-NANOPARTICLE ELEMENTS

(76) Inventors: Franco Vitaliano, 4 Longfellow Pl. #2105, Boston, MA (US) 02114;
Gordana Vitaliano, 4 Longfellow Pl. #2105, Boston, MA (US) 02114

(*) Notice: Subject to any disclaimer, the term of this patent is extended or adjusted under 35 U.S.C. 154(b) by 278 days.

(21) Appl. No.: 11/024,424

(22) Filed: Dec. 30, 2004

(65) Prior Publication Data
US 2007/0141163 A1    Jun. 21, 2007

Related U.S. Application Data

(60) Provisional application No. 60/534,354, filed on Jan. 6, 2004.

(51) Int. Cl.
    *C07K 14/00* (2006.01)
(52) U.S. Cl. .................................................... 530/350
(58) Field of Classification Search .................. None
    See application file for complete search history.

(56) References Cited

U.S. PATENT DOCUMENTS

| | | | |
|---|---|---|---|
| 5,427,767 A * | 6/1995 | Kresse et al. | 424/9.32 |
| 6,756,039 B1 * | 6/2004 | Yeates et al. | 424/192.1 |
| 7,033,834 B2 | 4/2006 | Valerio et al. | |
| 7,037,520 B2 | 5/2006 | Smyth Templeton | |
| 7,048,949 B2 | 5/2006 | Sligar et al. | |
| 7,060,291 B1 | 6/2006 | Meers et al. | |
| 7,063,860 B2 | 6/2006 | Chancellor et al. | |
| 7,101,532 B2 | 9/2006 | Aikawa et al. | |
| 7,101,570 B2 | 9/2006 | Hope et al. | |
| 7,108,863 B2 | 9/2006 | Zalipsky et al. | |
| 7,112,330 B1 | 9/2006 | Buonamassa et al. | |
| 7,112,337 B2 | 9/2006 | Huang et al. | |
| 7,268,116 B2 | 9/2007 | Liang | |

FOREIGN PATENT DOCUMENTS

WO    WO 2004/001019    * 12/2003

OTHER PUBLICATIONS

Antonny et al., Self-assembly of minimal COPII cages, EMBO Rep. Apr. 2003; vol. 4, pp. 419-424.*
Cheng, et al, Cryo-electron Tomography of Clathrin-coated Vesicles: Structural Implications for Coat Assembly, J. Mol. Biol. (2007) 365, 892-899.
DeNardo, et al, Effect of Molecular Size of Pegylated Peptide on the Pharmacokinetics and Tumor Targeting in Lymphoma-Bearing Mice, Clinical Cancer Research, vol. 9, 2003.
Fath, et al, Structure and Organization of Coat Proteins in the COPII Cage, Cell 129, 1325-1336, Jun. 29, 2007.
Fotin, et al, Molecular model for a complete clathrin lattice from electron cryomicroscopy, Nature, vol. 432, Dec. 2, 2004.
Fotin, et al, Structure determination of clathrin coats to subnanometer resolution by single particle cryo-electron microscopy, Journal of Structural Biology, 156 (2006) 453-4.
Guo and Linstedt, COPII-Golgi protein Interactions regulate COPII coat assembly and Golgi size, The Journal of Cell Biology, vol. 174, No. 1, Jul. 3, 2006 53-63.
Matsuoka, et al. Surface structure of the COPII-coated vesicle, PNAS Nov. 20, 2001 vol. 96 No. 24 13706-13709.
Sanford and Kumar, New proteins in a materials world, Current Opinion in Biotechnology 2005, 16:416-421.
Smith, et al. Clathrin coats at 21 Å resolution: a cellular assembly designed to recycle multiple membrane receptors, EMBO Journal vol. 17 No. 17 pp. 4943-4953, 1998.
Yokoyama and Ryan, Highly cooperative control of endocytosis by clathrin, unpublished, Department of Biochemistry, Weill Medical College of Cornell University.
Crowther, et al, 1976, On the structure of coated vesicles. J. Mol. Biol., 103, 785-798.
R.A. Crowther and B. M. F. Pearse, Assembly and Packing of Clathrin into Coats, The Journal Of Cell Biology, vol. 91 Dec. 1981 790-797.

* cited by examiner

*Primary Examiner*—Robert B. Mondesi

(57) ABSTRACT

The invention in suitable embodiments is directed to isolated bio-nanoparticle elements and isolated bio-nanoparticle platforms employing such isolated bio-nanoparticle elements. In one aspect, the isolated bio-nanoparticle elements are formed with purified Clathrin and or with purified coatomer I/II self-assembling protein molecules.

28 Claims, 5 Drawing Sheets

SMART BIO-NANOPARTICLE ELEMENTS

FIELD OF THE INVENTION

This application claims priority to Jan. 6, 2004, USPTO Application No. 60/534,354, with the provisional title, "Intelligent Bio-Structures". The invention relates generally to the field of nanoparticles, and more specifically, in one embodiment, to smart bio-nanoparticle elements formed from materials comprised of self-assembling protein molecules. In another embodiment, the invention relates to a multipurpose, multifunction nanoscale bio-nanoparticle platform, such as a drug discovery platform, electronics platform, information processing platform, telecommunication platform and the like, using such smart bio-nanoparticle (SBN) elements.

BACKGROUND OF THE INVENTION

Structures at the nanometer scale are sometimes referred to as nanoparticles. One example of nanoparticles is Fullerenes, which are the third allotropic form of carbon and form nanoparticles that may be an empty cage or the cage may contain cargo. The latter cage form is usually termed an endohedral Fullerene. Nanoscale endohedral Fullerenes can be used to stabilize reactive species inside the Fullerene cage, as in $N@C60$ or $Sc2C2@C84$. In addition, doped endohedral Fullerenes offer electronic and magnetic properties and might also be applied to electronics and information processing. Endohedral Fullerenes also have potential for biomedical applications such as targeted drug delivery, as well as other application areas.

In one application area, for example, the ability of endohedral Fullerenes to sequester one or more metal atoms, which may be toxic, inside the Fullerene cage has led to a research effort aimed at exploring their potential as contrast-enhancing agents for magnetic resonance imaging. Contrast agents enhance the quality of MRI images, aiding in the detection and diagnosis of injuries or abnormalities in the human body. The leading commercial MRI contrast agents are gadolinium (III) chelates such as gadolinium-diethylenetriaminepentaacetic acid, also known by its brand name Magnevist. Gadolinium III ($Gd3+$) works so well because of its unique electronic structure—it is the only ion with seven unpaired electrons. Once injected into the body, $Gd3+$ can magnetically "tickle" water protons present in tissues, accelerating their relaxation between radio-frequency pulses. Faster relaxation leads to higher signal intensity and therefore greater contrast in the MRI images. Encapsulating the gadolinium inside a Fullerene cage might prove safer, and such endohedrals potentially offer additional advantages. For example, the trimetallic-nitride-containing endohedral Fullerenes can accommodate three metal atoms inside each cage, potentially offering a more potent agent.

But before such endohedral Fullerenes can be tested and used in vivo, they must be made water-soluble. All endohedral Fullerenes exhibit extreme hydrophobicity, which must be overcome for many applications, especially for in vivo medical applications. One way to overcome this problem is to attach hydroxyl groups to the outer surface of the Fullerene cage. Compared with Magnevist, a commercially available contrast agent, prepared polyhydroxylated $Gd@C82$ can provide as much as 20 times better signal enhancement for water protons at much lower gadolinium concentration.

Although promising, there are problems with C82 endohedral Fullerenes. Most studies of metallofullerenes have centered on C82 isomers primarily because their solubility allows them to be more easily separated from empty Fullerenes and purified using high performance liquid chromatography (HPLC). But studies of polyhydroxylated $Gd@C82$ in rats revealed a significant, and potentially harmful uptake of the material by the reticular endothelial system, such as the lung, liver, and spleen. A similar uptake pattern of a polyhydroxylated derivative of $Ho@C82$ has been observed in these tissues, as well as in bone.

According to the Unites States Environmental Protection Agency (2003), which is funding research on nanoparticle toxicity, there is a serious lack of information about the human health and environmental implications of manufactured nanomaterials, e.g., nanoparticles, nanotubes, nanowires, Fullerene derivatives, and other nanoscale materials. Little is known about the fate, transport, and transformation of nanosized materials after they enter the environment. As the production of manufactured nanomaterials increases and as products containing manufactured nanomaterials are disposed of, these materials could have harmful effects as they move through the environment.

Forthcoming study results, including those funded by the EPA, may not be encouraging for pharmaceutical applications of Fullerenes like imaging contrast agents, because the metal-containing agent must be excreted without long-term retention in tissues. Unwanted organ and tissue retention also applies to targeted drug delivery systems using endohedral Fullerenes, which are about one nanometer in diameter. Organ and tissue retention issues also raise environmental concerns in general when in vitro endohedral Fullerenes or carbon nanotubes containing a metal or a toxic substance are free-floating in the air and are either inhaled into the lungs where they are absorbed into the body, and/or are absorbed into the body through contact with the skin.

Another drawback of C82 endohedral Fullerenes is that they are difficult to make in large quantities and with high purity, which is necessary for pharmaceutical applications and non-medical applications, like nanoscale electrical circuits. Generally, the success rate of creating endohedral Fullerenes is only about 1:10,000. This very poor success rates also leads to high costs. Endohedral Fullerenes cost as much as $1,000 per gram, in comparison to empty C60 cages, which cost only about $30 per gram.

Metallofullerenes in the C60 family, such as $Gd@C60$, have not been seriously considered for pharmaceutical applications because its members are generally insoluble and air-sensitive. On the plus side, $M@C60$ compounds can be produced in a carbon arc in yields up to 10 times higher than soluble $M@C82$ species. Water-soluble and fully air stable Fullerene fractions that are largely $Gd@C60$ have been experimentally produced. However, this material may contain several different isomers, rendering it unfit for many applications.

Besides using metal atoms, molecular clusters, and reactive species for medical imaging, chemists doing NMR spectroscopy have also encapsulated noble-gas atoms inside Fullerene cages and studied the interactions between the host and guest. In addition to Fullerene-caged helium, neon, argon, krypton, and xenon have also been put into Fullerenes, making unusual and highly stable noble-gas compounds in which no formal bond exists between the noble gas and the surrounding carbons. These compounds typically are made by heating the Fullerene in the presence of a suitable gas at 650° C. and 3,000 atmospheres. Under these conditions, though, no more than one in 1,000 Fullerene cages ends up with a noble-gas atom inside, making large scale production infeasible, as well as very costly.

Aside from helium for NMR spectroscopy, xenon ($129Xe$) is the only other noble-gas isotope having a spin of one-half, which makes the nucleus easily observable using NMR spectroscopy. But all endohedral Fullerenes suffer from a severe cargo carrying limitation, as the hollow core of the endohedral Fullerene is only seven to eight angstroms in diameter. Therefore, when trying to force xenon into C60, you get three to five times less xenon inside than helium, because xenon is so much larger. Such a tight fit brings into play another negative aspect common to all endohedral Fullerenes: the cage is highly conductive. When charge transfer to the Fullerene cage occurs, it distorts.

For example, xenon's 5p electrons are much closer to and interact much more strongly with the Fullerene's p electrons. When you alter the cage environment in any way, such as by making a Fullerene adduct, the cage may pucker slightly and the dimensions may change. The modified cage or the new group on the outside will interact very strongly with the enclosed cargo in ways that aren't easy to describe or predict. This cage distortion is not specific to xenon, and may occur with any enclosed particles that interact with the Fullerene cage. Endohedral Fullerene charge transfer and subsequent cage distortion is unacceptable in commercial and medical applications because results will not be consistent and predictable, and may also be harmful and injurious in some circumstances, like in vivo applications. This cage distortion drawback also potentially entails significant legal and medical liability issues.

The ability of endohedral Fullerenes to encapsulate various types of cargo is also limited. Apart from noble gases, the encapsulated metal atom can only be an alkali metal, alkaline earth metal, Sc, Y, U, or a lanthanide metal, with the most unusual of these species being Sc3N@C80, which has a nitride nitride-bridged Sc3N cluster inside a Fullerene. Most of the other metals in the periodic table do not form endohedral metallofullerenes, but rather form insoluble metal carbides and other unextractable materials.

Along with their limited cargo carrying capacity; charge transfer to the cage; organ and tissue retention; extreme hydrophobicity; and their difficulty of manufacture and very high cost, their cargo type limitations further limit the commercial and scientific potential of endohedral Fullerene-based endohedrals, for example, in the fabrication of nanoscale electronic integrated circuits.

Nanoscale integrated circuits from endohedral Fullerenes ("NICE"), apparently resolves at least one of these problems, namely, fabrication. NICE is the only known methodology that has been shown to produce macroscopic amounts of metal-containing endohedral Fullerenes. NICE uses a unique resistless proximal probe-based nanolithography technique to produce thin films of Fullerenes containing metal atoms. The films are characterized by laser desorption mass spectrometry and optical spectroscopy (IR and UV-vis absorption) among other methods. It is possible to dissolve the material and separate the endohedral compound from the empty Fullerenes and other material in the films. In this way macroscopic amounts of purified endohedral Fullerenes can be prepared, which up to now have been Li@C60. Material production and yield optimization for C60 endohedrally doped with other alkalis (Na, K) and the lanthanide La will also be developed at some point with NICE. A further innovative aspect of NICE is the additive approach taken to nanofabrication that uses a shadow mask technique whereby complex patterns such as rings and intersecting lines are readily produced. With the NICE method, the material composition of the as-deposited line can be varied, allowing for the formation of junctions within a single layer.

But NICE does not address the issues of limited cargo carrying capacity of endohedral Fullerenes, which is limited to just one to three atoms. Nor does NICE overcome the complex issues of charge transfer and endohedral cage distortion, which depend on certain quantum parameters of molecules, such as: point set groups, energies of electron levels, dipole (multipole) moments, electron affinity, ionization potential, molecular orbitals, electron density, electrostatic-potential derived charges, bond orders, net atomic charges, free valences, total energy, energy of formation, singlet and triplet UV/Visible spectra, IR and Raman spectra, polarizabilities, hyperpolarizabilities, magnetic moments, NMR properties, geometry optimization, atoms in molecules properties, etc. Nor does NICE overcome the issues of tissue and organ retention of potentially toxic endohedral Fullerenes when used in vivo, or the potentially harmful results of environmental exposure to endohedral Fullerenes. Nor does NICE overcome the extreme hydrophobicity of endohedral Fullerenes. Finally, NICE, which fabricates endohedral Fullerenes carrying metal cargo, does not fabricate Fullerenes that carry noble gases, and also does not overcome the fundamental cargo material type limitations of endohedral Fullerenes.

Methodologies such as NICE typically involve a "top down" assembly approach, and employ some form of lithography and replication. Top down approaches can be time consuming, expensive and exacting, and wasteful of materials if not performed correctly.

Another type of nanostructure, also sometimes referred to as a nanoparticle, consists of liposomes (spherical vesicles) that have been used as an alternative to in vivo endohedral Fullerenes because of the unique advantages of liposomes, which include their ability to protect their in vivo cargo from degradation, their ability to target their cargo, which can be a drug to the site of action, and to reduce the toxicity of side effects.

Another type of in vivo nanoparticle is comprised of lipids that has a surfactant agent and a cosurfactant agent and may also contain therapeutic agents, and possibly a steric acid. These lipid-based cages are 40 to 150 nanometers in size. These nanoparticles may be used to deliver entrapped agents across various biological barriers, such as the transmucosal passage, and also to overcome the blood-brain barrier (BBB) and the blood-cerebrospinal fluid barrier (CSG). As a general aspect, certain classes of surfactants have been shown to be effective at crossing these biological barriers and for allowing passage into the brain and CSF of various kinds of coated vesicles and nanoparticles having entrapped agents.

Another example of an in vivo nanoparticle is a therapeutic agent delivery system comprising a capsid formed from a coat protein of a bacteriophage selected from the group consisting of MS-2, R17, fr, GA, Q.beta, and SP, and with a foreign moiety enclosed in the capsid. The foreign moiety cargo is of a size sufficiently small to be enclosed in the capsid and the foreign moiety is linked to a RNA sequence comprising a translational operator of the bacteriophage. The translational operator binds to the coat protein during formation of the capsid.

The foregoing in vivo nanoparticle delivery approaches, including others in the prior art show promise as biological encapsulation methods and have the potential for becoming effective therapeutic agent delivery systems, especially those systems using surfactants. However, all of the foregoing biological cages, just like endohedral Fullerenes and others in the prior art, also suffer from various limitations that are unique to their various material compositions. For example, developmental work on liposomes and lipid nanoparticles has been limited, due to their inherent problems such as low encapsulation efficiency, rapid leakage of water-soluble drugs in the presence of blood components, and poor storage stability.

Furthermore, studies have concluded that the use of liposomes is an inefficient method of gene transfer for gene therapy, which incorporates functional genes into the cell to replace the action of dysfunctional genes. Inside of the body, liposomes fuse with cell membranes and deliver DNA to the cell via diffusion. However, studies have concluded that the use of liposomes is an inefficient method of gene transfer. Not only is plasmid size limited but gene loading is also poor: only one in every 100-10,000 liposomes contain intact DNA. In addition, many liposomes are taken into the cell by endocytosis, instead of releasing their DNA by diffusion. This leads to excessive breakdown of the DNA and results in poor transfection efficiency.

For many of these reasons, drug delivery systems using nanoparticles comprised of biodegradable polymers are emerging as one of the most widely used systems because of their numerous strengths, such as ease of fabrication, well-understood materials, and the ability to attach targeting moieties and barrier-passing surfactants.

Polymeric delivery systems were first used to provide the controlled release of many common drugs. Early polymers used were non-biodegradable and had to be surgically removed once its drug had been released. To avoid this inconvenience, researchers began searching for biodegradable alternatives. Successful controlled release systems have increased patient compliance in the administration of malaria drugs and several types of contraceptives in developing countries where patients have limited access to their physicians. In addition, such systems have also made improvements in the veterinary field, simplifying drug administration to animals. Controlled drug release has many advantages, including the ability to supply more constant drug levels, enable more efficient utilization of the drug, and the ability to locally deliver the agent and confine it to that area. In addition, decreased costs and frequency of administration add to the attractive features of biodegradable drug delivery systems.

Biodegradable polymers are generally divided into two categories: surface eroding polymers and bulk-eroding polymers. In surface-eroding polymers, erosion is confined to the polymer surface. In bulk-eroding polymers, erosion occurs throughout the entire cross-section of the polymer. However, the wide majority of polymers erode by a combination of both mechanisms. Degradation leads to erosion and is achieved by polymer chain scission, usually by hydrolysis.

For example, one biodegradable polymer nanoparticle approach uses sub-150 nm nanoparticles capable of transporting and releasing therapeutic agents, such as nucleic acids. DNA release in gene therapy applications is initially controlled by surface erosion followed by bulk erosion: as the backbone bonds hydrolize, channels form in the polymer allowing water to reach the interior of the nanoparticle. As water penetrates, bulk erosion occurs and the DNA is released. In one example, a biodegradable polymer nanosphere surface has attached to it a targeting moiety. In another nanoparticle embodiment, a biodegradable polymer nanosphere surface has attached to it a masking moiety. In yet another embodiment both targeting and masking moieties are attached to a nanosphere surface. In another biodegradable polymer example, surfactants have also been applied. For example, one nanoparticle mechanism uses biodegradable polybutylcyanoacrylate nanoparticles overcoated with polysorbate 80 for the purposes of crossing the BBB and CSF and delivering therapeutic agents.

The advantages and benefits of using biodegradable polymer nanospheres, including those that use surfactants and targeting moieties, are significant for in vivo targeted drug delivery. But they also create new classes of problems, and also do not overcome some existing ones, some of which issues are enumerated herein:

First, therapeutic agent models using in vivo biodegradable polymer nanospheres, liposomes, lipids, and caspid delivery nanoparticles, as well as endohedral Fullerenes, and others in the prior art still consist of an in vitro model being applied to an in vivo system, and clinical drug trials may show that promising in vitro results do not positively transfer to in vivo environment, especially in humans. This results in significant lost opportunity costs, as well as wastes large amounts of time, resources, and capital.

Second, side effect profiles are not satisfactorily addressed by the foregoing in vivo targeted delivery systems and in the prior art, and side effects may in fact be exacerbated because a highly potent concentration of a therapeutic agent will be delivered to highly targeted areas of interest. One possible consequence of in vivo targeted delivery systems is that dosing regimens, especially off-label use, may have to be significantly recalibrated by health care givers, necessitating new training and learning.

Third, the ability to cross various biological barriers into the brain and CSF, for example, using surfactants, and to deliver in vivo targeted concentrations of both small and large molecule payloads past these barriers will raise a host of new issues concerning agent efficacy, dosing and side effect profiles. As a consequence, individual patient factors such as genotype, phenotype, age, gender, ethnicity etc., may come into play more than ever, and these factors are not addressed by delivery systems in the prior art. Furthermore, once biological barriers to the brain and the CSF are commonly breached—especially by large molecule payloads that heretofore were not possible to typically deliver—new short and or long-term biological effects may also come into play and create important biological changes at the inter-cellular and intra-cellular level. Therefore, new, highly targeted drug regimens will need to be closely monitored and controlled after agent delivery for maximum efficacy and patient safety, and such monitoring and critical adjustments will need to be done on the fly and in vivo if they are to be maximally effective. However, all the foregoing in vivo delivery systems and others in the prior art lack such an in vivo ability to intelligently monitor, control, react, and dynamically adjust cellular processes after delivery of their agent payload to a target, as well as fail to take into account unique, individual patient factors.

Fourth, the materials comprising the foregoing delivery systems and others in the prior art are "dumb" materials. Although they may necessarily follow the control laws that regulate in vivo biochemical reactions and physiological processes, current in vivo delivery systems and others in the prior art do not feature or are not comprised of materials having the innate ability or characteristics to utilize and or leverage these control laws to intelligently respond to changing in vivo conditions. For example, the materials of the foregoing delivery systems and others in the prior art do not manifest an in vivo capability or the intelligence to dynamically alter a prescribed course of agent delivery in the face of an unexpected biological and or drug interaction, and in that sense, the regulatory control laws actually work against these dumb delivery systems. Once these dumb materials are set in motion, they cannot alter their course of behavior and are therefore highly static, fixed function systems.

Fifth, all the foregoing in vivo delivery systems and others in the prior art, with the possible exception of Fullerenes, lack structural persistence. Once the nanoparticles find their target and deliver their cargo, their job is finished and their various types of coatings rapidly disband, which means that the functionality of these various agent delivery systems and others in the prior art is severely time constrained. This temporal constraint represents a significant nanoparticle design limitation. Structural persistence for a period of time is a highly desirable quality for any nanoparticle or nanostructure as it permits the addition of temporal-based functionalities to the nanoparticles. For example, it may be highly advantageous for a nanoparticle to loiter for some period in an area after its initial agent delivery in order to monitor the situation and to potentially make a decision to deliver more agent cargo for improved agent efficacy.

Sixth, the ability to have multiple targeting moieties and one or more types of agents, while possible, is not currently practical with all of the foregoing systems, including others in the prior art. Multiple targets presume either on the fly smart target prioritization for a single cargo type or multiple cargo types that can be intelligently orchestrated and delivered in a dynamic environment—qualities that all of the foregoing delivery systems and others in the prior art currently lack.

Seventh, precise, highly ordered placement of cargo elements with minimal inter-cargo spacings is not possible with any of the foregoing in vivo agent delivery systems and others in the prior art, which are basically hollow nanospheres with no internal structural elements except for the cargo they may be carrying. Internal precision ordering of such agent cargo within the nanoparticle can, for example, enable the precise, intelligently controlled spatial and or temporal release of agents. Minimal inter-cargo spacings within the nanoparticle also afford the ability to tightly pack agents, especially mixed agents types—e.g., a diagnostic agent and a therapeutic agent—into the same nanoparticle with minimal interference between agents. Precision ordering and spacing within a nanoparticle is therefore in of itself an integral component of a targeted system, amplifying and extending the capabilities of agents carried within the nanoparticle.

Eighth, all current delivery systems and others in the prior art are limited to carrying cargo just within their cavities. Currently, they have no capabilities for building aggregated complexes of self-assembled structures that dynamically bind together one or more elements, some of which may be heterogeneous and external to the nanoparticle, into complex systems having one or more external elements, cavities and payload types. Current in vivo delivery systems and others in the prior art therefore do not make possible the assembly of sophisticated, complex nanostructures that fully exploit all the manifold possibilities of targeted agent delivery.

Ninth, there is no provision or capability for programming algorithmically-driven behaviors into the current targeted agent delivery systems and others in the prior art, with the possible exception of endohedral Fullerenes, and their capability for becoming smart, programmable and or self-directed systems to perform complex and sophisticated tasks in vivo is therefore severely limited, if not impossible.

Tenth, there is currently no provision or capability for integrating current agent delivery systems and others in the prior art, with the possible exception of endohedral Fullerenes, into other smart devices and mechanisms either in vivo or in vitro, either functionally or logically, including with other devices and operators at a distance (e.g., telemedicine), thereby limiting their overall therapeutic, diagnostic, therapeutic and system expansion capabilities.

Thus, there exists a need for an improved nano-structure element that overcomes the limitations of in vivo and in vitro endohedral Fullerenes, as well as overcomes the limitations of biodegradable polymer nanospheres, liposomes, lipid-formed systems, caspids and other agent delivery systems in the prior art for in vivo applications.

SUMMARY OF THE INVENTION

The invention, in one aspect, remedies the deficiencies of the prior art by providing a nanoscale smart bio-nanoparticle (SBN) element, which may be employed in a scalable, smart bio-nanoparticle platform. An SBN platform according to the invention may be used, for example, in biomedical, electronics, telecommunications, and information processing applications.

In one embodiment, the SBN element is formed from one or more nanoscale cargo elements contained within a self-assembling protein cage. In some configurations, cargo elements include one or more metals. In other embodiments, the cargo elements are exclusively non-metal cargo elements that may include gases, as well as other cargo elements like drugs, optics, polymers, etc. One advantage of the invention is that it inhibits charge transfer between the cage and its enclosed cargo and prevents cage distortion. Another advantage of inhibiting charge transfer is that it reduces limitations on the make up of enclosed cargo elements. According to one feature, the SBN element is formed using a "bottom-up" fabrication approach. According to such an approach, various self-assembling and self-directed approaches are employed. Using such an approach, the SBN platform can be formed from the ground up, one element at a time, for highly specific nano-scale tasks. Another advantage of the "bottom-up" fabrication approach is that it reduces the amount of superfluous material that surrounds each cargo element within the cavity, reducing the cargo element's exposure to contaminant background radiation and thereby improving the functional effectiveness of the cargo. A further advantage of the bottom-up self-assembly of the SBN element is that it enables the precise, highly ordered placement of cargo elements with minimal inter-cargo spacings, thus avoiding a significant drawback to the use of endohedral Fullerenes, and also of other prior art endohedral Fullerene approaches, such as precise ion implantation through masks, and manipulation of single atoms using probes. In addition, the invention can maintain its structural integrity at room temperature in vitro and vivo, which eliminates the need for elaborate structure stabilizing mechanisms, like cooling systems. In one embodiment, the cavity defined by the cage is larger than those described in the Fullerene art, so the invention can incorporate a larger variety and number of cargo elements. According to another feature, the proteins that form the cage can be bio-engineered using commercially available biotechnology tools and other tools and techniques known in the art to contain different cargo elements, which makes the invention more versatile and cost-effective than the existing Fullerene art. Unlike existing Fullerene systems where the cargo elements must be inserted into an existing structure, the invention, in one embodiment, provides individual protein molecules that self-assemble around the cargo elements to form the cage, which makes the addition of cargo elements easier.

Another advantage of the invention is that the SBN protein material does not exhibit extreme hydrophobicity. A further advantage of the invention is that it provides a protein structure that can be bio-engineered to prevent in vivo SBN and or cargo uptake by organs, tissue, and bone and the SBN and or its cargo are secreted quickly and easily. In the converse, another advantage is that the SBN protein material and or its cargo can be bio-engineered for highly selective uptake by targeted cells, tissue, organs, bone, as well as other organic and inorganic matter.

Unlike current nanoparticle in vivo agent delivery systems, and also of other prior art, the invention's biological model is consistent from in vitro to in vivo, making drug discovery safer, more efficacious, more time and cost effective, and overall, a much more rapid process. Further unlike existing nanoparticle in vivo agent delivery systems, and also of other prior art, the invention, in one embodiment, provides for individual patient factors such as genotype, phenotype, age, gender, ethnicity etc., to be taken into account and factored into dosing and administration consideration. Also unlike existing nanoparticle in vivo agent delivery systems, and of other prior art, the invention, in one embodiment, provides for dynamic, in vivo dosing regimens that significantly reduce drug side effect profiles. And further unlike existing nanoparticle in vivo agent delivery systems, and of other prior art, the invention, in one embodiment, provides for the ability to intelligently monitor, control, react, and further adjust biological processes after delivery of agent cargo payload, and to do so on the fly and in vivo. Further unlike existing nanoparticle in vivo agent delivery systems, and of other prior art, the invention, in one embodiment, provides a structure that maintains its structural integrity long enough to do useful work for a time certain period. Also unlike existing nanoparticle in vivo agent delivery systems, and of other prior art, the invention, in one embodiment, provides bottom-up self-assembly of the SBN element and the precise, highly ordered placement of cargo elements with minimal inter-cargo spacings. Further unlike existing nanoparticle in vivo agent delivery systems, and of other prior art, the invention, in one embodiment, provides for the ability to attack multiple in vivo targets on the fly using smart target prioritization for a single cargo type and or multiple cargo types that can be intelligently orchestrated and delivered in a dynamic in vivo environment. Also unlike existing nanoparticle in vivo agent delivery systems, and of other prior art, the invention, in one embodiment, provides for smart materials that may deliberately exploit and leverage regulatory control laws, and these smart materials may dynamically and interactively respond to changing in vivo environments using various self-directed behaviors. Also unlike existing nanoparticle in vivo agent delivery systems, and of other prior art, the invention, in one embodiment, provides for the ability for building aggregated, complex self-assembled structures that dynamically bind together one or more exogenous, heterogeneous elements into complex systems having one or more cavities and payload types. The invention therefore makes possible the assembly of smart, complex delivery vehicles that fully exploit all the possibilities of targeted agent delivery systems.

Further unlike existing nanoparticle in vivo agent delivery systems, and of other prior art, the invention, in one embodiment, provides for a capability for targeted agent delivery systems that deliberately leverage and utilize biological control laws and may act as smart, self-directed systems. Moreover, unlike existing nanoparticle in vivo agent delivery systems, and of other prior art, the invention, in one embodiment, provides a capability for its integration into other smart devices and mechanisms, some of which may be heterogeneous, either in vivo or in vitro, and either functionally or logically, including with other devices and operators at a distance, thereby significantly enhancing the overall capabilities of the invention.

In general, in one aspect, the invention features an SBN element that includes a cage defining a cavity in which one or more cargo elements are located. The cage is formed from a plurality of self-assembling protein molecules. In a further embodiment, at least one of the cages includes a cargo element.

In one embodiment, one or more SBN elements and or SBN-related elements and in any combination include synthetic materials that are organic and or inorganic in composition.

In various embodiments of the invention, the cage is substantially larger than one nanometer in diameter, including sizes that can exceed about 50 or even about 100 nanometers in diameter. According to one embodiment, the self-assembling cage is a functional substitute for $C_{60}$, $C_{80}$, $C_{82}$, and other types of empty Fullerene cages, as well as a substitute for cargo carrying endohedral Fullerenes. Furthermore, empty cage Fullerenes, carbon nanotubes, cargo carrying endohedral Fullerenes and other nanoparticles such as liposomes, caspids, lipid-formed vesicles, polymer, polybutylcyanoacrylate, and cetyl alcohol nanoparticles, but not limited to such, may be carried as ordered cargo within the self-assembling protein cage.

The relatively large size of the cage and its structural components allows for a large and wide variety of possible cargo elements, especially in contrast to the limited cargo capacity of Fullerenes. The SBN and or cargo elements may also modify, process, manipulate, encode and decode, input, output, transmit, communicate, store and or read information using techniques known in the art, in vivo and in vitro.

Preferably, the cage has faceted geometry. In some embodiments the cage is symmetric with respect to a plane. In one embodiment, ordered cargo elements are linearly positioned at vertices along a single plane using circulant ordering. In one particular embodiment, the self-assembling protein molecules that make up the cage are clathrin molecules, which may be biologically engineered. In another embodiment, the self-assembling protein molecules that make up the cage are coatamer protein molecules, which also may be biologically engineered.

According to another feature, once inside the SBN, cargo is protected from the external environment, and the SBN is stable with respect to dissociation and any cargo toxicity is sequestered from the surrounding environment.

According to one feature, an SBN element and or cargo elements may use a reservoir of unassembled SBN materials and or cargo materials to re-supply, reassemble and regenerate defective and or destroyed and or inoperable SBN and or cargo elements.

In some configurations, the cage contains a single cargo element, while in other configurations it contains multiple cargo elements. In some cases, each of the cargo elements is or includes a metal. Alternatively, some of the cargo elements are or include non-metal elements.

According to one feature, the cargo elements may include one or more research, therapeutic, diagnostic, assay, or prosthetic agents. Such agents may be, for example, nano-structured and/or may include chemical, biological and/or metallic materials. The agents may be or include organic or inorganic materials or a combination thereof.

According to one SBN embodiment, a cargo element contains an ion with one or more unpaired electrons. According to one in vivo application for enhanced medical imaging, paramagnetic lanthanide or transition metal ion complexes are cargo elements that decrease the NMR relaxation times of nearby proton nuclei of H2O molecules, leading to brighter images and enhanced contrast between areas containing the contrast agent and the surrounding tissues.

According to another feature, one or more cargo elements may be or include nanoscale assay systems, diagnostic devices and agents, sensors, therapeutic devices and agents, and/or prostheses, in any combination. Some or all of the cargo elements may operate under the control and influence of other SBN elements, and altogether may comprise a scalable, nanoscale information-processing platform for SBN-based biomedicine.

According to another feature, the SBN uses its material properties and directed self-assembly to address all issues associated with nanotechnology information processing devices: Atomic and molecular scale device design, their interconnection, nanofabrication and circuit architectures.

In another configuration, the invention features the ability to intelligently respond to in vivo and or in vitro environmental conditions and manifest special functions. Protein molecules used by the invention can perform a physical form of bio-computation via their dynamic (energy-consuming) self-assembly actions. They compute, not by moving electrons around in transistor circuits, but by moving molecules around and adding or removing them from constantly modified nanostructures. Mere molecules can act in complex, coordinated fashion—they are executing a kind of physical "computer program". The invention may use this bio-mechanism to develop self-directed, self-assembly processes. The invention in one embodiment yields a new and novel way to build incredibly small structures that manifest "bio-intelligence." The seat of this intelligence within the invention materials lies in their deliberate utilization and taking advantage of biological control laws.

The various control laws that regulate biochemical reactions and physiological processes often display features that allow biomolecules or biological structures to perform more tasks than are reasonably expected from a simple mechanical device. A distinctive hallmark of the intramolecular dynamics of biomolecules is the concerted and interlocking steps of conformational changes that lead to a purposeful action: each part fits spatially and each step fits temporally (kinetically) with an element of anticipation of the purposeful outcome. These concerted and interlocking steps are sometimes referred to as closed entailment loops (Rosen). The overall process exhibits intentionality that is conducive to the suggestion of a master hand behind the design. Of course, the evolutionary mechanism, and now bio- and genetic engineering replace the need of a master hand. In one embodiment, the invention takes deliberate advantage of these biological control laws, and via the use bio- and genetic engineering methods known in the art makes use of these control laws to regulate complex in vivo and in vitro biochemical reactions and physiological processes. An example of biological control laws at work is the automatic self-directed, self-assembly in vitro and in vivo of Clathrin and coatamer proteins, which are both highly complex structures.

In the invention, the artificially-induced and or natural binding of an SBN element to a cell membrane, other tissue, and or an in vitro element such as, for example, but not limited to, a pathogen and the resulting biological processes and interactions may lead to a series of deliberately controlled, extended, modulated, purposefully, and or self-directed behaviors of bioengineered SBN materials that provide real time, self-adaptive, self-regulatory in vivo and or in vitro behaviors on the part of the SBN. The deliberately extended and or modified behaviors, functionalities, and characteristics of a bioengineered SBN constitute a smart bio-computer that is an analog to electronic processing systems directed by software-based algorithms.

In one SBN embodiment, intramolecular dynamics of biomolecules and the concerted and interlocking steps of conformational changes lead to deliberately purposeful actions. For example, each SBN element fits spatially and each step in a process fits temporally (kinetically) with an element of anticipation of the purposeful outcome. In one example embodiment, conformational changes and or non-covalent bonding of an SBN structural element to a cell membrane may lead to the precise dispatch and sequenced delivery of selected cargo agents from the SBN structure to the target cell. Alternatively, a new series of interlocking steps between a part of a cell membrane and all or a subset of the materials comprising an SBN structure may cause the cessation of agent delivery to the target cell. In another example case, the spatially and temporally defined control events between the cell and the bioengineered SBN materials may cause the SBN structure to release diagnostic and monitoring agents to determine the most appropriate course of therapeutic action. The calculated utilization of biological control laws by SBN materials may, for example, provide for a sophisticated drug delivery system that provides optimal dosing by altering its drug delivery behavior and also producing minimal side effect profiles.

In one SBN embodiment, graphs are used. By utilizing graphs and Lie algebras, including Clifford algebras, geometrically-derived algorithms produce one or more elements whose geometric structures possesses certain desired properties and capabilities for an SBN and constituent SBN materials. Graphs, geometrical pictures, simple or complex, are used in mathematical models for the study of the production of SBN proteins and their spatial folding, with applications to drug design and genomics. Graphs provide a simple beginning to many complicated objects. In such a situation one hopes to show how combinatorial properties of the graph are reflected in the resulting object—does the simple object "control" the complicated one? The complicated objects in this instance are highly infinite operator algebras, like Infinite-dimensional Lie algebras. Even elementary examples illustrate the passage from graph to algebra, like the construction of a tree, and while the boundary of a tree is space, the boundary of a graph is an algebra.

According to another feature, the invention is an improvement over in vivo biodegradable nanoparticles in the prior art because in some invention embodiments it may use molecular-imprint technology. Molecular imprinting, or biomimetic chemistry that deals with imitations of natural binding entities, such as enzymes and antibodies, involves preorganization of polymerizable monomers around an imprinting molecule. Following polymerization and removal of the imprint molecule, the solid polymer contains binding sites that are complementary in size and shape to the template. This cavity, in one embodiment, can facilitate catalysis of certain reactions and may also be used for shape selective separations. In other embodiments, imprinted polymers embodiments may facilitate the fabrication of SBN membrane materials to achieve selective diffusion; as chromatographic supports for the separation of enantiomers and oligonucleotides by SBN elements; to provide the recognition element for SBN chemical sensors, and for the synthesis of polymeric materials that mimic biological receptors that are targeted by SBN elements and or play a role in the design of new drugs. Other SBN embodiments may utilize imprinted membranes and thin films that also function as an artificial cell wall for the selective transport of targeted drugs, peptides and biologically important molecules.

According to another feature, biodegradable films may also be used as a pliable template for biological elements, which elements are pressed into a biodegradable film and then removed, leaving a physical mold of the biological element's shape. The film can then be hardened and used by an SBN to detect that particular biological element, which may be, but is not limited to, a particular receptor, protein, or cell, since its complex imprint shape on the film will bind only to that particular biological element. Molecular imprinting polymerization renders a polymer matrix with a series of cavities, or imprints, that are complementary in size, shape and position of chemical functionalities to a template molecule. These imprints enable the polymer matrix to rebind the template molecule selectively from mixtures of closely related compounds. One illustrative invention embodiment provides for a molecular-level process for biodegradable capsule production and produces nanocapsules with surface feature sizes at the molecular level.

In one embodiment, the molecular-level imprint process provides for a smart targeting system using biodegradable nanocapsules for delivery of one or more SBN cargo elements and or one or more non-SBN elements in vivo or in vitro. In another embodiment, molecular imprinting is used for the production of molecule-specific cavities that mimic the behavior of natural receptor binding sites, without the temperature sensitivity of the natural systems. Artificial polymers may be built for any target molecule. The polymers are prepared in the presence of a template molecule that interacts with the polymer network via ionic, covalent or hydrogen bonding interactions. Target specificity of the correct docking position for an imprinted nanocapsule embodiment is provided by the geometric pattern on the nanocapsule that locks onto its complementary shape on the docking site, forming a transient complex. The shape of the docking pattern matters more than non-covalent bonds, because, with the exception of electrostatic interactions, non-covalent bond interactions are extremely short ranged (no more than a few angstroms). Various biodegradable materials may be used in various embodiments for imprinting, including, but not limited to, bio-base materials, polymers, biological elements, and other materials such as biodegradable plastics and films.

In one application, SBN elements perform targeted agent delivery in vivo or in vitro, wherein the agents are one or more research, diagnostic, therapeutic, prosthetic, and or assay agents.

In one application, SBN elements perform targeted agent delivery in vivo or in vitro using as appropriate ligands, and or targeting moieties, and or other vectors.

In another application, an intelligent, nanoscale, cell-sized platform comprised of SBN elements performs smart molecular-level and or cellular-level target site loitering, monitoring, repair, construction and or dynamic, interactive control of systems, in vitro and in vivo. SBN biomedical platforms include, but are not limited to, imaging, sensor, genetic and protein assay, diagnostic, drug delivery, prosthetic, and intra-cellular, tissue, organ, and or circulatory engineering, modification and repair platforms, including implantable defibrillators, pacemakers, coronary stents, and angioplasty devices and or systems.

According to one illustrative configuration, one or more cargo elements that interfere with a SBN's operation if carried in the same protein cage as another cargo element type is instead carried in a separate SBN element protein cage that exclusively carries non-interfering cargo elements, thereby inhibiting disruptive interference with SBN operations. Such non-interfering-only cargo cages may be functionally and or physically linked with other SBN element cages carrying other cargo element types.

In another aspect, the protein cage features no cargo elements at all. According to one embodiment, empty self-assembling cages include highly ordered scaffolding for self-assembling multi-layer, multi-dimensional, multi-SBN element and multi-non SBN element systems.

In another aspect, the faceted geometry of the protein cage enables a shape programmable system to which other elements may be bonded, fastened, and or affixed using molecular or chemical means and or otherwise attached.

As a general aspect, an SBN element and its cargo elements may take any suitable form, and multiple SBN element embodiments may be further combined in any suitable manner to create multifunction, scalable platforms, including scalable information processing platforms that use some or all SBN and or non-SBN elements and cargo as bits that are programmable into a plurality of logical states.

The SBN element, in one configuration, includes receptor molecules, natural and or synthetic, for capturing and ordering the placement of the cargo elements inside the cage.

The SBN element, in one configuration, includes adapter molecules disposed between the receptor molecules and the cage to couple the receptor molecules to the cage inside the cavity.

In another SBN element configuration, molecular or chemical bonding is used to attach directly cargo elements internally or externally to the cage in an ordered arrangement. In other SBN element configurations, a short molecular tether is used to attach cargo elements internally or externally to the cage in an ordered arrangement. In another embodiment, site directed cysteine mutagenesis is used to incorporate elements into the SBN protein materials. In other SBN element configurations, receptors, molecular tethers, direct bonding and cysteine mutagenesis are used in any combination to attach and orderly position cargo elements within the cage.

In some configurations, the cargo elements located within the cage form one or more permeable, semi-permeable, and or non-permeable cavities.

In some configurations, the SBN element includes a vesicle located within the cage, with one or more cargo elements located within the vesicle. In such a configuration, receptor molecules extend through the vesicle to capture and order one or more cargo elements within the vesicle. According to one embodiment, the vesicle is protein-based. According to a feature of this embodiment, the protein-based vesicle inhibits charge transfer between the vesicle and its enclosed cargo elements.

In another configuration, cargo elements within a vesicle may not be attached to receptors, and the cargo may be free floating within the cavity of a non-permeable vesicle, for example, in an encapsulated fluid or gas. In other configurations, both the self-assembling cage and vesicle may be devoid of cargo. According to one feature, the cage, cargo elements within the cage, and/or a vesicle within the cage including its cargo elements, respond to certain external and/or internal stimuli, which can be, for example, mechanical, chemical, biochemical, biological, metabolic, covalent, non-covalent, ionic, photonic, sonic, acoustical, thermal, fluidic, electromagnetic, magnetic, radioactive, or electrical in nature. An example of such a stimulus response is deformation of the geometry of a cargo element within a cage, deformation of a vesicle within a cage, and/or deformation of the cage itself and or other conformational changes.

In another configuration, the invention features a scalable SBN information-processing platform that may include one or more embodiments of the SBN elements described above. The scalable information-processing SBN platform may also include an encoder, e.g., a predetermined or specific DNA sequence that deliberately encodes at least a subset of the protein cargo elements within the SBN to take the form of specified sequence, as well as a decoder for reading information from at least a subset of the protein-based information processing elements. Examples of such a bio-system decoder are, but not limited to, a dye-based protein assay, a quantum dot-based assay, or other protein assay methods known in the art. Another example of encoders/decoders is the use NMR and ESR and other methods known in the art that can effect and discern protein behaviors and their physical characteristics. Another example of encoders/decoders is the use of photons of different wavelengths and photo detectors.

In general, in another embodiment, an SBN element and an SBN platform are physically and/or functionally cooperative with other suitable types or forms of elements, agents, organisms, materials, substances, components, devices, and or systems, in vitro and/or in vivo.

In another embodiment, an SBN element and an SBN platform are physically and/or functionally combined, embedded and or incorporated into one or more other suitable elements, agents, materials, and or substances in vitro and/or in vivo.

According to another illustrative embodiment, an SBN element and an SBN platform are embedded and or incorporated into one or more suitable devices, components, systems, organisms, and or mechanisms in vitro and/or in vivo.

In general, in a further aspect, the invention is directed to a method of forming an SBN element, including the steps of forming in vitro from self-assembling protein molecules, such as clathrin and or COPI and or COPII molecules, a cage defining a cavity, and locating one or more cargo elements within the cavity.

In general, in a further aspect, the invention is directed to a method of forming an SBN element comprised of one or more types of materials, including the steps of providing one or more embodiments of the SBN elements described above to deliberately carry out a series of tasks in accordance with the control laws that regulate biochemical reactions and physiological processes.

In general, in another aspect, the invention is directed to a method of forming a scalable SBN platform, including the steps of providing one or more embodiments of the SBN elements described above, and utilizing cargo contained in one or more SBN and or non-SBN elements to deliberately carry out a series of tasks, which tasks are externally directed or internally self-directed, or a combination thereof.

In general, in a further aspect, the invention is directed to a method of forming a scalable SBN information-processing platform, including the steps of providing one or more embodiments of the SBN elements described above. In one embodiment, the platform includes locating at least one cargo element, capable of expressing a plurality of logical states that is located within or externally attached to the SBN, for example, quantum dots that express logical states via the use of different wavelengths of light.

BRIEF DESCRIPTION OF THE DRAWINGS

The foregoing and other aspects of the invention may be more fully understood from the following description, when read together with the accompanying drawings in which like reference numbers indicate like parts.

DESCRIPTION OF THE ILLUSTRATIVE EMBODIMENTS

Figure 1:
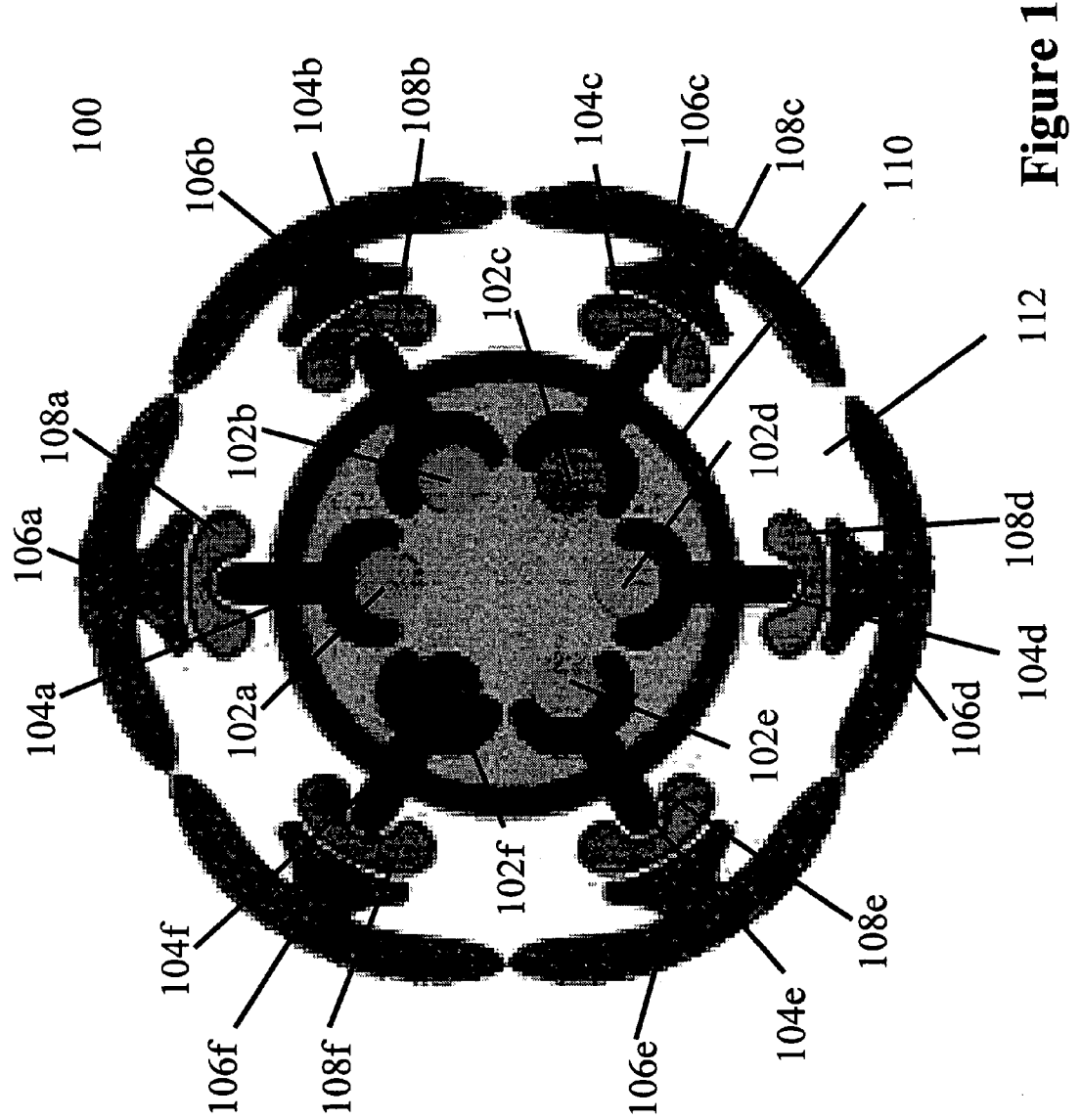
FIG. 1 is a conceptual cross-sectional view of a biological endohedral cage (SBN) element according to an illustrative embodiment of the invention.

FIG. 1 is a conceptual cross-sectional view of a biological endohedral cage (SBN) element 100 according to an illustrative embodiment of the invention using Clathrin. The SBN element 100 includes one or more cargo elements 102a-102f, a plurality of receptor molecules 104a-104f, a plurality of protein molecules 106a-106f formed into a cage 106, and a plurality of adapter molecules 108a-108f, as well as a vesicle 110. The protein molecules 106a-106f self-assemble in vitro to form the cage 106 that defines a cavity 112.

As shown, the receptor molecules 104a-104f each bond with a respective cargo element 102a-102f, and the adapter molecules 108a-108f bond the receptor molecules 104a-104f to the protein molecules 106a-106f, respectively. The bonding may be either covalent or non-covalent—the latter type including ionic interactions, hydrophobic interactions, or hydrogen bonds—depending on the application, system design, receptor design, cargo type and/or the interaction/application environment. Some G protein-coupled receptors (GPCRs) use covalent bonds, which are individually strong (e.g., it takes energy to break the covalent bond). In some instances, the clathrin molecule attaches covalently to the solution termini of alkanethiol SAMs/SPMs via covalent bonding. In other illustrative embodiments, electrostatic (ionic) bonding may be employed.

Most GPCRs do not form covalent bonds with their ligand when bound in the receptor. Noncovalent interactions are individually weak but collectively strong, such as with a substantial number of noncovalent interactions working together to hold a structure together, or a surface topography that enables substantial areas of two interacting surfaces to approach each other closely. Ligands generally bind to receptors via ionic, hydrophobic hydrogen and van Der Waal bonds, which often involve short-range interactions between molecules and the same molecule. These short-range non-covalent bond interactions and forces also underlie the intramolecular processes collectively referred to as conformational changes of proteins.

Cage 106 can be naturally occurring or biologically engineered and/or can use synthetic proteins in whole or in part. Also, the receptor molecules 104a-104f can be naturally occurring or biologically engineered and/or can use synthetic proteins in whole or in part to recognize specific cargo elements 102a-102f. Likewise, the adapter molecules 108a-108f can be naturally occurring or biologically engineered and/or can use synthetic proteins in whole or in part to recognize and couple to particular receptor molecules 104a-104f.

Optionally, the protein cage 106 forms to enclose (e.g., to "coat") a vesicle 110 within the cavity 112. ARF-GTP, appropriate lipids, and cytosolic factor(s) are used for AP-1 clathrin coated vesicle assembly. Recruitment of AP-1 (Assembly Polypeptides) onto liposomes is ARF-dependent and facilitated by cytosolic ARF Guanine Nucleotide-Exchange Factor (GEF). Lipid composition is important and modulates ARF and AP-1 binding. The vesicle 110 can be formed, for example from naturally occurring membrane material, such as L-a-Phosphatidylinositol-4, 5-bisphosphate or from synthetic membrane materials, such as a fully synthetic liposome like one containing DOPC DOPE cholesterol or from a mixture of both, for example, from synthetic lipids such as L-a-Phosphatidylcholine (PC) from soybeans containing 20% PC (Sigma P5638).

In one embodiment, adapter molecules tether the vesicle 110 to the cage 106. The adapter molecules 108a-108f, in turn, bond to receptor molecules 104a-104f disposed around the periphery of the vesicle 110. According to the illustrative embodiment, the receptor molecules 104a-104f extend through the vesicle 110 to capture the cargo elements 102a-102f.

In one illustrative embodiment, the self-assembling protein molecules 106a-106f are clathrin molecules, and the clathrin cage 106 can be of any suitable size. According to the illustrative embodiment, the clathrin cage 106 has a diameter greater than about one nanometer. In various other illustrative embodiments, the clathrin cage 106 can have a diameter between about one nanometer and about fifty nanometers, a diameter between about fifty nanometers and about one hundred nanometers, or a diameter greater than about one hundred nanometers. The vesicle 110 may have any suitable size, such that its diameter is less than that of the clathrin cage 106.

In one embodiment, cargo elements 102a-102f are cavity forming and are non-permeable, semi-permeable, and or permeable, and or can change from one permeable state to another.

In another embodiment, vesicle 110 is cavity forming and non-permeable, semi-permeable, or permeable, and or can change from one permeable state to another.

Figure 2:
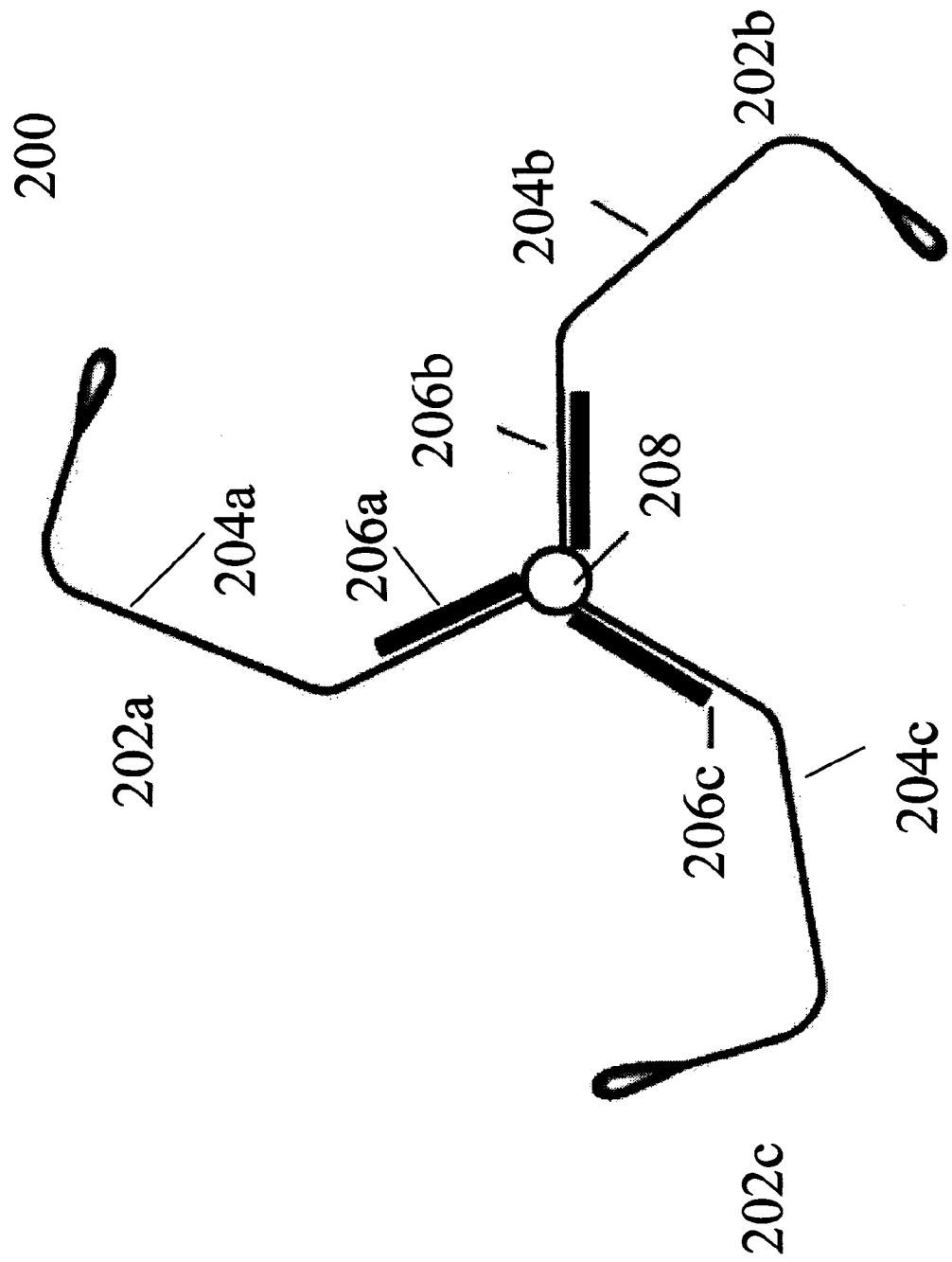
FIG. 2 is a conceptual diagram depicting a clathrin triskelion of the type employed in an illustrative embodiment of the invention.

FIG. 2 is a conceptual diagram depicting a basic unit of clathrin, a three-armed pinwheel structure called a triskelion 200. The filamentous portion of a clathrin triskelion leg is formed by a continuous superhelix. Clathrin is composed of three polypeptides, three 190 kDa subunits ("heavy chains") and three 24-27 kDa subunits ("light chains"), which combine to create a distinct three-legged triskelion 200. It is this morphology that allows clathrin to form its unique polyhedral network. The three-arms 202a-202c extend radially from a hub section 208. Each arm 202a-202c includes one heavy chain section 204a-204c, respectively, and one light chain section 206a-206c, respectively. The heavy chain sections 204a-204c are relatively flexible and can adopt different geometry's within the clathrin cage 106. In one illustrative embodiment, the clathrin triskelia 200 are biologically engineered to modify and/or enhance the properties of the heavy chain sections 204a-204c, including the heavy chain terminal domain that provides multiple interaction sites for the variety of adaptor proteins that bind ligands. In one illustrative embodiment, the clathrin triskelia 200 are biologically engineered to modify and/or enhance the properties of the three 24-27 kDa subunits ("light chains").

In another embodiment, clathrin cage 106 is formed by three-legged triskelion 200, wherein clathrin cage 106 morphology is bioengineered to form polyhedral networks, some of which have, but are not limited to, 60, 70, 72, 80, or 82 vertices.

In another illustrative embodiment, the clathrin triskelia 200 are biologically engineered to modify and/or enhance the clathrin light chain section 206a-206c located proximal to the center of clathrin triskelion 200 to accept free radical molecules such as nitroxide molecule spin labels for electron paramagnetic resonance (EPR) based SBN applications. In the nitroxide example, the molecules are attached to a short molecular tether to clathrin light chain section 206a-206c by site directed cysteine substitution mutagenesis, followed by reaction of the unique cysteine with a specific molecular spin label.

In another embodiment, elements, materials and substances, including other biological elements such as ligands, receptors and adaptors, may also be bonded, fastened, and or affixed to and or incorporated into clathrin triskelia 200 and or heavy chain sections 204a-204c and or light chain sections 206a-206c by site directed cysteine substitution mutagenesis and or attached via molecular tethers. Studies by means of site-directed mutagenesis of proteins have demonstrated that the buried interior of a protein can tolerate considerable diversity of residue substitution with only minor effects on the structure, stability, and function. Despite what appears to be a highly complex three-dimensional jigsaw, the buried protein is not tightly packed, but maintains a fluid-like environment, at least for certain parts and at certain times. For example, activation of an enzyme often involves the conformational change from a taut (tense) form (T state) to a more relaxed form (R state), whereas inactivation involves the reversal of the change. Thus, proteins are endowed with a malleability that is compatible with gradualism, as opposed to featuring abrupt and potentially destructive or disruptive changes. Apparently, the tolerance has been built in the evolutionary selection of 20 different kinds of amino acids as the building blocks of proteins. The amino acid redundancy with regard to polarity and steric property (shape) when coupled with the fluid-like environment permits a protein to tolerate a major packing fault most of the time ("gradualism").

In one embodiment, the invention takes full advantage of such protein flexibility and plasticity, as well as the forgiving nature of proteins to create bioengineered structures using site-directed mutagenesis on cage 106, and or cargo elements 102a-102f, and or receptors 104a-104f and or adaptors 108a-108f and or vesicle 110, and or into clathrin triskelia 200 and or heavy chain sections 204a-204c and or light chain sections 206a-206c and or on targeting moieties, and or on elements bonded, fastened, and or affixed to cage 106 and or on Coatamer proteins I and II.

In another embodiment, no molecular tether is involved. In one configuration, a free radical molecule may be attached directly to cage 106. In another embodiment, a free radical molecule may be attached to receptors 104a-140f.

In another embodiment, free radicals circulating within an in vivo environment are scavenged by clathrin triskelion 200 via molecular tethers attached to clathrin light chain section 206a-206c and or by direct cage covalent and or non-covalent bonding.

Figure 3:
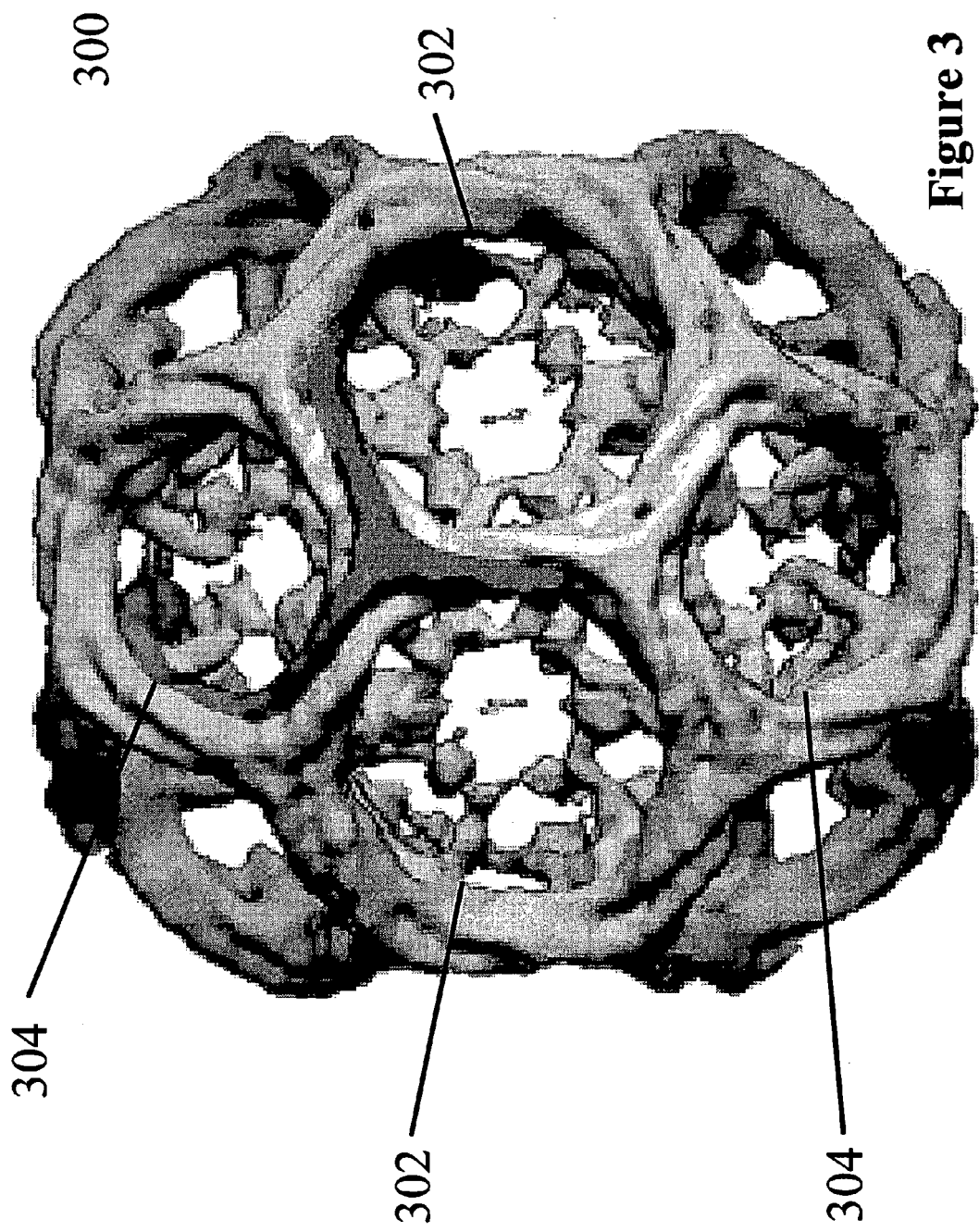
FIG. 3 is a computer generated frontal view of an actual clathrin protein cage, formed according to an illustrative embodiment of the invention.

Clathrin networks are formed when several triskelia of the type depicted in FIG. 2 associate together to form a lattice or cage 300, as illustrated by FIG. 3. The clathrin cage 300 includes a symmetrical pattern of hexagons 302 and pentagons 304. In the illustrative embodiment, the clathrin cage 106 has icosahedral geometry.

As mentioned above, naturally in vivo occurring clathrin cages 106 assemble around membranes to form vesicles. Referring again to FIG. 1, the adapter molecules 108a-108f couple clathrin proteins 106a-106f to receptor molecules 104a-104f disposed around the periphery of the vesicle 110. According to one illustrative embodiment, the clathrin cage 106 is formed around the vesicle 110 in vitro using synthetic, natural, or mixed lipid monolayers or bilayers and purified receptor 104a-104f and adapter 108a-108f molecules. For example, in one illustrative embodiment, clathrin cage 106 is formed by biologically engineered clathrin proteins 106a-106f and adapter molecules 108a-108f, such as AP-2 and AP180, to a PIP2-containing lipid monolayer. According to one feature of the invention, the receptor molecules 104a-104f are biologically engineered by means known in the art to recognize and associate with specific molecules that serve as the cargo elements 102a-102f. According to another feature, the adapter molecules 108a-108f are biologically engineered to recognize specific receptor molecules 104a-104f and couple the receptor molecules 104a-104f to the clathrin cage 106.

Alternatively, the clathrin cage 106 can be formed in vitro, without the vesicle 110, by changing the pH or ionic strength of the solution in which the clathrin proteins 106a-106f are located.

Below pH 6.5, purified clathrin triskelions self-assemble in vitro into a polyhedral lattice (cages) without vesicles, but typically only form cages at physiological pH in the presence of stoichiometric quantities of purified AP-1 or AP-2 adaptor molecules or the neuron-specific assembly proteins AP-180 and auxilin. Recombinant hubs, formed from residues 1074-1675 of the clathrin heavy chain, are trimeric structures that reproduce the central portion of the three-legged clathrin triskelion, extending from the vertex to the bend in each leg, comprising the binding sites for clathrin light-chain subunits. Without light-chain subunits, recombinant hubs self-assemble reversibly at physiological pH, while hubs with bound light chains self-assemble below pH 6.5, similar to purified clathrin. Inhibition of hub assembly by light-chain subunits is a key to controlling spontaneous clathrin self-assembly at physiological pH. The mean curvature of baskets (cages without vesicles) is adjustable by the pH level and by other environmental conditions. As can be deduced from the formation of the microcages, a clathrin network can have such a pH-controlled curvature, even in the absence of a membrane bilayer. In addition, a conserved negatively charged sequence of three residues (23-25) in the clathrin light-chain subunits regulates the pH dependence of hub assembly. Also, two classes of salt bridge (high affinity and low affinity bridges) play a dominant role in driving clathrin assembly. Basket closure depends on the presence of TDD domains (terminal and distal domains). A connection between the proximal and distal domains is not required for curvature, and the TDD themselves can orient the assembling hubs in a favorable angle for polyhedron formation.

Figure 4:
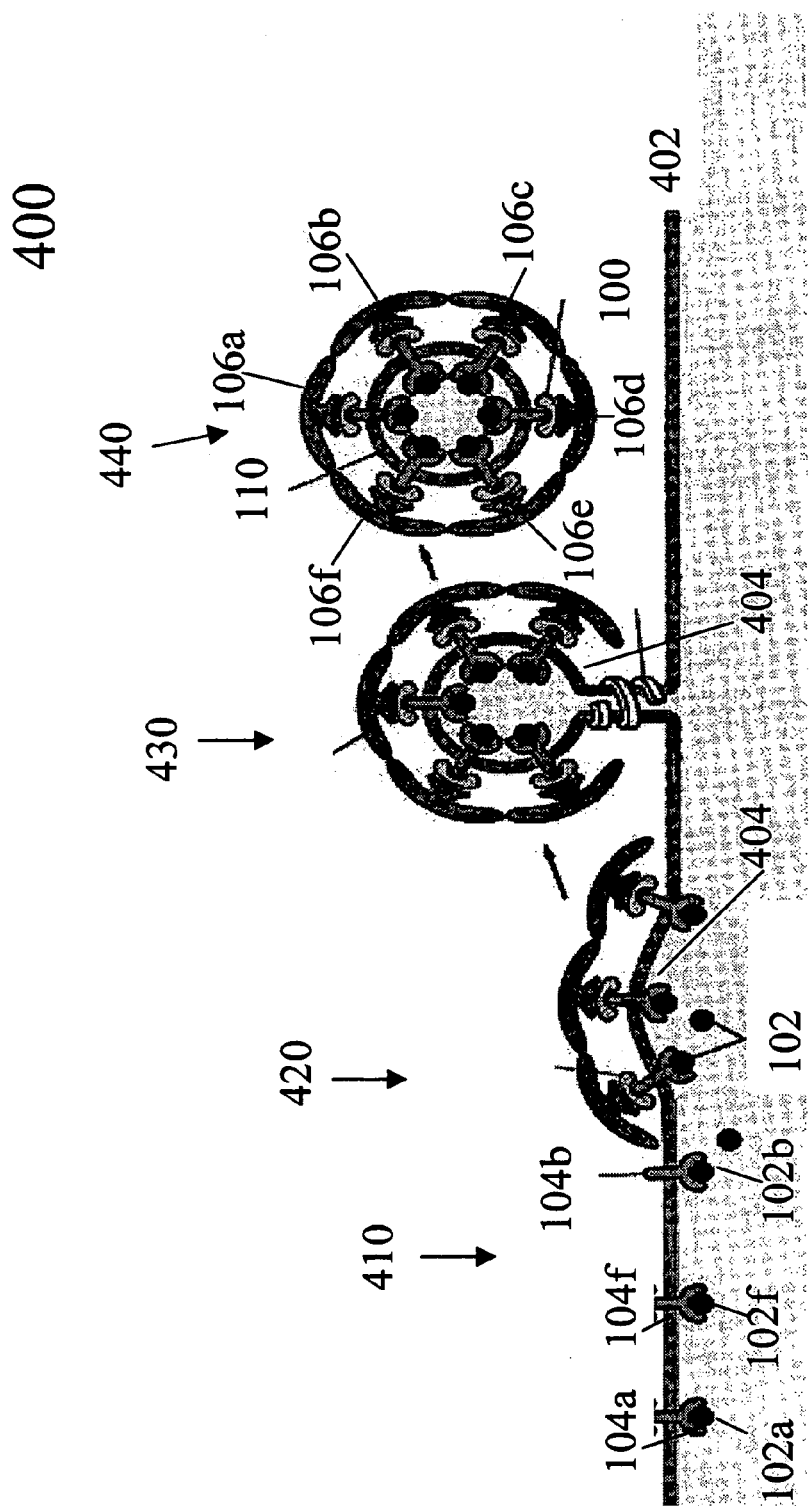
FIG. 4 is a flow diagram depicting conceptually the formation of an SBN element in vitro according to an illustrative embodiment of the invention.

FIG. 4 is a flow diagram 400 depicting, conceptually, the formation of an SBN element 100 according to an illustrative embodiment of the invention. The process by which the clathrin molecules 106a-106f obtain cargo molecules 102a-102f in vivo is known as endocytosis, wherein a cell takes in macromolecules by forming vesicles derived from the plasma membrane. Clathrin also transports proteins from the Golgi complex to other organelles. Clathrin-mediated endocytosis is a process by which the cells internalize receptors, transmembrane channels, transporters and extracellular ligands such as hormones, growth factors and nutrients. In neurons, endocytosis is critical to allow rapid synaptic vesicle regeneration. In addition, endocytosis of ligand-activated receptors is essential for the proper attenuation of a variety of signal transduction processes, as well as for co-localization of activated receptors with downstream signaling molecules.

The endocytosis process begins when proteins bound to receptors accumulate in coated pits, which are specialized regions of the membrane where it is indented and coated on its cytoplasmic side with a bristle-like coat composed of two proteins: clathrin and protein adapters. Most, if not all, intracellular transport vesicles are encased in a proteinaceous coat, one class of which is clathrin-coated vesicles (CCVs). CCVs mediate the transport of lysosomal hydrolases from the trans-Golgi network, as well as the efficient internalization of extracellular solutes such as nutrients, hormones, growth factors, and immunoglobulins at the plasma membrane.

By deliberately utilizing and or modifying the SBN formation process, the invention can produce specific, custom tailored outcomes. For example, referring to FIGS. 1 and 4, in the case where a vesicle 110 is desired, the cargo molecules 102a-102f are initially located behind a membrane, such as a cytosol membrane 402. As shown at 410, the receptor molecules, such as the receptor molecules 104a, 104b and 104f, bond with the cargo molecules, such as the cargo molecules 102a, 102b and 102f, respectively, through the membrane 402. As shown at 420, the clathrin molecules, such as the clathrin molecules 106a, 106b and 106f then bond through the adaptor molecules, such as the adaptor molecules 108a, 108b and 108f, respectively, to the receptor molecules, such as the receptor molecules 104a, 104b and 104f, respectively, to begin to form a clathrin coated vesicle (CCV) with icosahedral symmetry. Regulatory processes within membrane 402 cause clathrin bud 404 to form at 420. As shown at 430 and 440, after forming completely around the bud 404, the clathrin cage 106 pinches off (scissions) from the membrane 402 leaving it with the cargo molecules 102a-102f inside the vesicle 110. After excision, the bud 404 has evolved into clathrin cage 106, a complete CCV with a symmetric icosahedral structure.

The heat shock cognate protein, hsc70, helps to regulate the endocytosis aftermath of CCV uncoating and disassembly in vivo and in vitro. Hsc70 also promotes uncoating and disassembly of Coatamer I and II vesicles. In cells overexpressing ATPase-deficient hsc70 mutants, uncoating of CCVs is inhibited in vivo. In a preferred embodiment, maintaining CCV and clathrin cage and or Coatamer I and II vesicle integrity in the invention over prolonged periods of time in vivo and in vitro may be applied by methods such as, but are not limited to, an over expression of ATPase-deficient hsc70 mutants, and or the use of a monoclonal antibody against hsc70 to block the hsc70-mediated release of clathrin from coated vesicles to specifically inhibit the heat shock-induced nuclear migration of hsc70; any or all of which anti-disassembly and anti-dissolution techniques may be additionally created and modified as appropriate via bioengineering techniques to inhibit or promote CCV and or Coatamer I and II vesicles and or non-vesicle cage disassembly and or the release of cargo. In one embodiment, disassembly and dissolution of cage 106 and or cargo elements 102a-102f, and or vesicle 110 is inhibited and controlled and or promoted on a timed-release basis and or by using one or more specific stimuli.

In one invention embodiment, coatamer coat proteins are used instead of clathrin coat proteins, preferably in those applications where coatamer coating and uncoating characteristics may be more desirable than those of Clathrin.

In one illustrative embodiment, the self-assembling protein molecules 106a-106f are Coatamer I or II molecules, and the coatamer cage 106 can be of any suitable size. According to the illustrative embodiment, the coatamer cage 106 has a diameter greater than about one nanometer. In various other illustrative embodiments, the coatamer cage 106 can have a diameter between about one nanometer and about fifty nanometers. In various embodiments, cargo elements 102a-102f are contained within Coatamer I and or II vesicles, which can be readily formed using in vitro processes, and may also be bioengineered. COPI-coated vesicles can also be formed from synthetic liposomes.

Coatamer proteins (COPI and COPII) also play a role in exocytosis, which refers to the fusion of intracellular vesicles with the plasma membrane. It occurs via two major processes, a constitutive pathway and a regulated pathway. These are the major ways that the cell secretes materials, wherein a cell secretes macromolecules (large molecules) by fusion of vesicles with the plasma membrane. Coatamer-coated vesicles, which are typically less than fifty nanometers in size, are also involved in vesicular transport between the Golgi apparatus, endoplasmic reticulum and plasma membrane. Coatamer I vesicles shuttle elements from the Golgi to the endoplasmic reticulum (ER). Coatamer II vesicles shuttle elements from the ER to the Golgi. Coat-protein subunits (COPs) require ATP to assemble into a coat and unlike clathrin coats, the coatomer coat remains on the vesicle until docking occurs. In some instances, coatamer proteins are also involved in endocytosis, but are unrelated to Clathrin.

In one invention embodiment, clathrin and coatamer protein coated vesicles may be used together in the same SBN, taking advantage of their respective capabilities.

According to one illustrative embodiment, the clathrin coated vesicle assembly process is carried out by preparing clathrin-coated vesicles 110 for incorporation of SBN cargo elements, such as the cargo elements 102a-102f, from cytosolic preparations, including methods, but are not limited to, as essentially described in Takei, et al., Cell, 94: 131-141 (1998). Liposomes are prepared as described in Reeves, et al., J. Cell Physiol., 73: 49-60 (1969). Essentially, lipids are solubilized in a 1:2 mixture of chloroform and methanol, and dried in a rotary evaporator. The preparation is rehydrated in a stream of water-saturated nitrogen for twenty minutes. Lipids are then placed in a flask with gently degassed 0.3 M sucrose. The flask is flushed with nitrogen, sealed, and left undisturbed for two hours at 37 degrees Celsius. Liposomes are then recovered by centrifugation at 12,000×g for ten minutes and resuspended in cytosolic buffer prior to incubation.

Cytosolic preparations are made by any convenient method. Numerous methods are described in the prior art. See, e.g., Huttner, et al., J. Cell Biol., 96: 1374-1388 (1983), incorporated by reference herein. Essentially, viable cells are collected by centrifugation and resuspended in hypotonic lysis buffer. Membranes are disrupted by homogenization, and the cytosolic fraction is collected after pelleting membrane debris. Briefly, cells obtained from culture are transferred to hypotonic lysis buffer (100 mM HEPES (pH7.9), 15 mM MgCl2, 100 mM KCl, 0.1 M DTT) and centrifuged. The resulting pellet is resuspended in phosphate buffered saline and centrifuged. The supernatant is decanted. A volume of lysis buffer is then added that is about five times the pellet volume. The pellet is gently resuspended and placed on ice in lysis buffer for 15 minutes. The suspension is then centrifuged for 15 minutes at 420×g. The supernatant is removed and discarded and the pellet is resuspended in a volume of lysis buffer equal to twice the pellet volume. Cells are disrupted by ejection through a syringe, and the disrupted cells suspension is centrifuged at 10,000×g for 20 minutes. The resulting supernatant is the cytosolic fraction.

Next, clathrin coated proteins are extracted from clathrin-coated vesicles 110 obtained from organic tissue. According to one illustrative embodiment, but is not limited to, bovine brain tissue is used. Coat protein is extracted from coated vesicles in a buffer containing 0.8 M Tris-HCl (pH 7.4), 2 mM EGTA, 0.03% sodium azide, 0.5 mM DTT, and 1 mM PMSF for fifteen minutes at room temperature. The preparation is then centrifuged at 100,000×g for one hour at room temperature to produce a supernatant containing soluble coat protein. The isolated proteins are used directly or frozen in liquid nitrogen at −70 degrees Celsius.

The resulting clathrin-coated vesicles 110 can be visualized under electron microscopy as described below.

According to one illustrative embodiment, but is not limited to, recombinant clathrin formation may be achieved in the following exemplar manner. Stoichiometric quantities of adaptor element 206 proteins AP-1 and AP-2 are required for clathrin self-assembly at physiological pH. However, in vitro clathrin self-assembly occurs spontaneously below about pH 6.5. Recombinant terminal and distal domain fragments are produced and combined with recombinant-produced hub fragments in assembly buffer as described below in order to induce formation of closed clathrin cages, such as the cage 106, for use in the invention.

In one illustrative technique, bovine clathrin heavy chain cDNA encoding heavy chain amino acids 1-1074 (SEQ ID NO: 1) is cloned into the pET23d vector (Novagen) between the NcoI (234) and XhoI (158) sites. Expression of the cloned sequence results in a terminal and distal domain fragments having a C-terminal polyhistidine tag. Hub fragments corresponding to amino acids 1074-1675 (SEQ ID NO: 2) are cloned into vector pET15b (Novagen) between the BamHI (319) and XhoI (324) sites. Expression of the hub fragments produces the proximal leg domain and central trimerization domain of the clathrin hub with an N-terminal polyhistidine tag. Vectors containing the heavy chain and hub domains are expressed in $E.$ $coli$ by induction with 0.8 mM isopropyl-B-D-thiogalactopyranoside for 3 hours at 30 degrees Celsius. Expressed proteins are purified from bacterial lysate in binding buffer (50 mM Tris-HCl (pH7.9), 0.5M NaCl, 5 mM imidazole) in a nickel affinity resin using the polyhistidine tag. Proteins are eluted with 100 mM EDTA and dialyzed against 50 mM Tris-HCl (pH7.9). Hub fragments are further purified using size exclusion chromatography on a Superose 6 column (Pharmacia).

In another exemplar technique, Clathrin assembly reactions are performed using expressed heavy chain and hub fragments by overnight dialysis at 4 degrees Celsius in assembly buffer (100 mM 2-(N-morpholino) ethanesulfonic acid, pH 6.7, 0.5 mM MgCl2, 1 mM EGTA, 1 MM Tris (2-carboxyethyl)-phosphine hydrochloride, 3 mM CaCl2. Assembly reactions are centrifuged for 5 minutes at 12,000 rpm. The supernatant is then centrifuged for 45 minutes at 45,000 rpm (100,000×g). The pellets are resuspended in assembly buffer, and protein composition is determined on SDS-PAGE. The efficiency of cage 106 formation can be determined by electron microscopy by diluting assembly reactions 1:5 in 10 mM Tris pH7.9, and placing aliquots on a glow-discharged carbon-coated grid, using 1% uranyl acetate as the stain. Cage 106 formation is assessed by counting the numbers of cages 106 having closed, defined edges and visible hexagonal/pentagonal lattice structure.

According to another illustrative embodiment, clathrin coated proteins are extracted and prepared from clathrin-coated vesicles 110 obtained from non-bovine organic tissue, including from human tissue, in whole or in part. In another embodiment, clathrin coated proteins are extracted and prepared from clathrin-coated vesicles 110 obtained by donor/recipient tissue matching using established techniques. In another embodiment, clathrin coated proteins are prepared, in whole or in part, by using cloning and or other genetic manipulation techniques known in the prior art to produce genetically-matched tissue for an intended recipient.

No membrane proteins are essential for the coatamer vesicle formation process. Liposomes of simple and defined compositions are sufficient to create a platform for the binding of coatomer and Arf1p and for the production of synthetic COPI vesicles that approximate in size the authentic vesicles formed from Golgi membranes. Thus, as was shown for COPII, and also was shown recently for the clathrin coat, COPI subunits assemble in a regular manner that dictates the size and shape of a coated vesicle. In each case, acidic phospholipids promote coat protein recruitment. However, each coat differs in the specificity of the acidic lipid requirement and in the dependence for vesicle formation on the presence of a small GTP-binding protein. The major subunits of COPII bind to liposomes and bud vesicles only in the presence of Sarlp-guanosine 5'[γ-imidylyl]triphosphate. (Clathrin vesicles form from acidic liposomes even in the absence of GTP-binding protein.)

According to one illustrative embodiment, the coat protein complex I (COPI)-coated assembly process is carried out by preparing coatamer-coated vesicles for incorporation of SBN cargo elements, such as the cargo elements 102a-102f, from cytosolic preparations, including methods, but are not limited to, as essentially described in Spang, et al., Proc. Natl. Acad. Sci. USA. 1998 Sep. 15; 95 (19): 11199-11204. Coatamer, a complex of seven distinct subunits or COPs, and ADP-ribosylation factor (ARF, an N-myristylated small GTP-binding protein) are the only cytoplasmic proteins needed for the assembly and budding of COP-coated vesicles.

Synthetic coat protein complex I (COPI)-coated vesicles form spontaneously from large (≈300 nm in diameter), chemically defined liposomes incubated with coatamer, Arflp, and guanosine 5'[γ-thio]triphosphate. Coated vesicles are 40-70 nm in diameter, approximately the size of COPI vesicles formed from native membranes. The formation of COPI-coated buds and vesicles and the binding of Arflp to donor liposomes depend on guanosine 5'[γ-thio]triphosphate. In contrast to the behavior of the COPII coat, coatamer binds to liposomes containing a variety of charged or neutral phospholipids. However, the formation of COPI buds and vesicles is stimulated by acidic phospholipids. In the absence of Arflp, coatamer binds to liposomes containing dioleoylphosphatidic acid as a sole acidic phospholipid to form large coated surfaces without forming COPI-coated buds or vesicles. Arflp-GTP and coatamer comprise the minimum apparatus necessary to create a COPI-coated vesicle.

Complex I (COPI)-coated vesicles materials: Phospholipids and their derivatives may be purchased from Avanti Polar Lipids. Phosphatidylinositol 4-phosphate (PIP), phosphatidylinositol 4,5-bisphosphate ($PIP_2$), cytidine 5'-diphosphate-diacylglycerol, ergosterol, and other reagents may be obtained from Sigma. Proteins resolved by SDS/PAGE are stained with SYPRO Red (Molecular Probes). *Escherichia coli* BL21(DE3) strains, which coexpress yeast N-myristoyl-transferase and either wild-type or dominant activated yeast Arflp, are provided by R. Kahn (Emory Univ.). N-myr-yArflp (wild-type) and N-myr-yArflp (Q71L) are purified as described. Yeast coatamer are prepared as described by Hosobuchi et al.

Preparation of Liposomes and Binding of COPI Proteins: Liposomes are made from a mixture containing 80% (by weight) phospholipids and 20% ergosterol. Dried lipids are hydrated at 2.3 mg/ml and extruded five times through a 400-nm polycarbonate filter (Poretics) to prepare liposomes as described. The phospholipid mix contains, unless indicated, 49 mol % dioleoylphosphatidylcholine (DOPC), 21 mol % dioleoylphosphatidylethanolamine (DOPE), 8 mol % phosphatidylinositol (PI) from soybean, 8 mol % dioleoylphosphatidylserine (DOPS), 5 mol % dioleoylphosphatidic acid (DOPA), 2.2 mol % PIP, 0.8 mol % $PIP_2$, 2 mol % cytidine 5'-diphosphate-diacylglycerol, 2 mol % 7-(nitrobenz 2-oxa-1,3 diazol-4yl)-(NBD-) derivative of DOPE, and 2 mol % 1-oleoyl-2-NBD-N-aminododecanoyl-sn-glycero-3-phosphocholine. A portion (11 μl) of this mixture is incubated with 20 μg Arflp or ArflQ71Lp in 25 mM Hepes (pH 7.4), 0.5 mM $MgCl_2$, 1 mM EDTA, 1 mM DTT, 100 mM NaCl, and 0.14 mM GTP-γ-S or guanosine 5'[γ-thio]triphosphate for 1 h at 30° C. The reactions are chilled on ice, and 37.5 μg of coatamer is added. After 15 min, the samples are fixed and processed for electron microscopy as described below. For sedimentation analysis, liposomes incubated with a combination of ArflQ71Lp or Arflp, coatamer, and nucleotide are loaded on top of a linear sucrose gradient (0.2-1.8 M sucrose) in 20 mM Hepes (pH 7.4), 150 mM potassium acetate, 5 mM MgCl2, and 250 mM sorbitol. The gradient is centrifuged for 16 h at 55,000 rpm in a Beckman TLS55 rotor. Fractions (23×100 μl) are collected from the top. For analytical purposes, the fractions are collected into a microtiter plate, and the fluorescence of the NBD-phospholipids in each fraction is analyzed by using a STORM 860 image analyzer (Molecular Dynamics). In preparative scale reactions, fractions from four identical gradients are combined and processed for electron microscopy as described earlier. For flotation analysis, liposomes are made with various combinations of phospholipids. The resulting liposomes are incubated with Arflp and coatamer in the presence of guanine nucleotide as described above. Liposomes are recovered by flotation centrifugation, and liposome-bound proteins are analyzed by SDS/PAGE and SYPRO Red staining. COPII binding to these liposomes is carried out as described.

Electron Microscopy: After the binding reaction, either total reactions or sucrose gradient-separated liposomes are fixed with 2% glutaraldehyde and 1% osmium tetroxide in cacodylate buffer for 1 h on ice. Fixed samples are sedimented by centrifugation at 100,000×g for 45 min. Pellets are contrasted with tannic acid and are embedded in Epon. Thin sections are contrasted further with uranyl acetate and lead citrate and are photographed in a Philips CM10 electron microscope (Philips Electron Instruments, Eindhoven, Netherlands). Photographs taken at a calibrated magnification are printed on paper. The size and number of the different species of liposomes are assessed on the enlarged photographic prints.

In one embodiment, cage 106 has icosahedral geometry. In some embodiments, the cage is symmetric with respect to a plane. In one embodiment, receptors 104a-104f, adaptors 108a-108f, and or cargo elements 102a-102f are linearly positioned at cage 106 vertices along a single plane using circulant ordering, and which structures also may use directed self-assembly via graphs and an algebra, for example, a Lie algebra.

In one illustrative embodiment, cage 106 and or cargo elements 102a-102f and or vesicle 110 and or element 100 are permanently stable with respect to dissociation in vivo and or in vitro.

In another illustrative embodiment, disassembly and dissolution in vivo and or in vitro of cage 106, and or cargo elements 102a-102f, and or vesicle 110, and or element 100 are deliberately inhibited and controlled.

In one illustrative embodiment, cage 106 and or elements 102a-102f and or vesicle 110 and or element 100 may remain for a time certain or estimated time in vivo and or in vitro before the onset of dissociation of cage 106 and or elements 102a-102f and or vesicle 110 and or element 100.

In one illustrative SBN embodiment, dissociation of in vivo and or in vitro of cage 106, cargo elements 102a-102f and or vesicle 110 and or other elements comprising element 100 may occur in whole or in part.

In one illustrative SBN embodiment, cavity forming cargo elements 102a-102f and or cargo elements within cavity forming vesicle 110 may contain one or more cage 106 uncoating and dissociation agents that are used for controlled release of agents or cargo from one or more cage 106, cargo elements 102a-102f, and or vesicle 110.

Clathrin and or coatamer protein uncoating and dissociation agents may include, but are not limited to, ATPase (UA), a cognate heat shock protein (hsc70), cystolic factors, and ATP that promote the release of clathrin coat protein and or coatamer coat protein, as well as promote the release, in whole in part, of cargo elements 102a-102f from their adaptor proteins 108a-108f. Such uncoating and dissociation methods may be further modified in whole or in part by bioengineered techniques.

According to one feature, the protein receptors 104a-104f shield cargo elements 102a-102f in the same clathrin cage 106 from interacting with each other. According to a further feature, the protein adaptors 108a-108f shield cargo elements 102a-102f in the same clathrin cage 106 from interacting with each other. According to another feature, the vesicle 110 shields cargo elements within vesicle 110 in the same clathrin cage 106 from interacting with each other. According to another feature, the shielding properties of the cage 106 shields and inhibits chemical and molecular interactions between the external in vivo and or in vitro environment and element 100, According to a further feature, cage 106 protectively sequesters cargo elements contained within cargo elements 102a-102f and or vesicle 110 from the external in vivo and or in vitro environment.

Preferably, some SBN elements include cargo, such as a molecule having an unpaired electron, a transition metal ion, which can be found in the active centers of many proteins (metalloproteins), or a material having any defect that produces an unpaired electron.

SBN cargo elements may include, for example and without limitation, one or more cosmetics, pharmaceuticals, biologicals, radioactive agents, magnetic iron oxide nanoparticles, or other substances, and also may contain one or more nanoscale biosensors, diagnostic systems, or other nano-devices for in vivo delivery of targeted therapy to combat diseases, such as cancer and HIV. In vivo delivery of such nano-biomedical systems may utilize a variety of techniques, like degradable coatings and nanoscale electromechanical systems, which are capable of being harmlessly dissolved or harmlessly passed through the body. SBN-related cargo elements may contain, for example, but not limited to, smart nano-prostheses that supplement or enhance cell, tissue, or organ functioning, thereby providing them with augmented capabilities. Some or all such cargo may operate under the control and influence of various other SBN elements, and comprise another type of SBN platform.

In another illustrative SBN embodiment, self-assembling cage 106, and or cargo elements 102a-102f, and or vesicle 110, which may also be self-replicating, self-adapting, self-repairing, self-regulating, and or self-regenerating, contain one or more cargo agents for studying, discovering, preventing, curing, and or healing tree, plant, grain, grass, agricultural, vegetable, and fungal diseases, disorders, infestations, and or blights.

In another illustrative SBN embodiment, self-assembling cage 106, and or cargo elements 102a-102f, and or vesicle 110, which may also be self-replicating, self-adapting, self-repairing, self-regulating, and or self-regenerating, contain one or more cargo agents for nourishing and promoting growth in trees, plants, grains, grasses, agriculture, vegetables and fungi.

In another illustrative SBN embodiment, therapeutic agent cargo elements may also contain one or more genetic material cargo for studying, discovering, designing, and enabling of genetically engineered elements, for example, genes, cells, and other biological elements and products in trees, plants, grains, grasses, agriculture, vegetables and fungi.

The invention, in one embodiment, offers an improvement over previous developmental efforts to use nanoparticles as in vivo cargo carriers, such as liposomes, but not limited to, for drug delivery, which nanoparticles heretofore have been limited, due to inherent liposome problems such as low encapsulation efficiency, rapid leakage of water-soluble drugs in the presence of blood components, and poor storage stability. In one embodiment, multiple liposomes may be carried in vivo within one or more cage 106, and or sequestered as cargo within cavity forming elements 102a-102f, and or contained within cavity forming vesicle 110. By using one or more cage 106, cavity forming elements 102a-102f and or cavity forming vesicle 110 to carry liposomes, the invention overcomes the low encapsulation efficiency of liposomes by using an ensemble method that employs large numbers of agent-carrying liposomes, which in the aggregate provide effective dosing ranges of one or more diagnostic or therapeutic agents. Sequestering liposomes within cage 106, cavity forming cargo elements 102a-102f, and or cavity forming vesicle 110 also overcomes two other problems with "naked" liposomes; rapid leakage of water-soluble drugs in the presence of blood components, and poor storage stability.

In one embodiment, the invention is an improvement over biodegradable polymer nanospheres, liposomes, lipids, caspid agent delivery systems, as well as endohedral Fullerenes and other nanoparticles in prior art, because the invention enables aggregated, complex self-assembled structures that bind together one or more elements that may be heterogeneous, which also may be exogenous to cage 106, into complex systems having one or more cavities and payload types.

In one embodiment, one or more cage 106, receptors 104a-104f, adaptors 108a-108f, cargo elements 102a-102f, and or vesicle 110 are conjugated with one or more elements, agents, materials, and substances, including elements, agents, materials and substances developed by $3^{rd}$ parties. These elements, agents, materials, and substances may be used singly or mixed together in any combination, and may be used for medical and biological research, diagnosis, therapy, or prosthetic purposes.

In one illustrative embodiment, cage 106, and or cargo elements 102a-102f and or vesicle 110 and or bonded elements are coated in whole or in part with other elements, materials, and substances that are natural and or synthetic.

In another embodiment, one or more SBN element 100 comprise an in vitro and or in vivo model and or system for research study, including a model and or system for the research and development of new drugs, therapies, prosthetics, and drug delivery systems, including an accelerated drug discovery process.

In one illustrative embodiment, the invention enables a biological model that is consistent from in vitro to in vivo.

In another embodiment, one or more SBN element 100 comprise a model and or system for doing clinical trials of one or more types of agents in vivo or in vivo, including targeted agent delivery, in humans and animals.

In another illustrative SBN embodiment, self-assembling cage 106, and or cargo elements 102a-102f, and or vesicle 110, and or their bonded elements, which may also be self-directing, self-replicating, self-adapting, self-repairing, self-regulating, and or self-regenerating, contain one or more agents for studying, discovering, designing, creating and or doing trials of cosmetic agents and or therapies for humans and or animals.

In one embodiment, one or more SBN elements and or SBN-related elements and in any combination include one or more pharmaceutical agents, including, but not limited to, drug discovery agents; drug designer agents; drug research and development agents; drug fabrication agents; drug controller agents; drug modifier agents, targeted drug delivery agents; clinical drug trial agents.

In one embodiment, one or more SBN elements and or SBN-related elements and in any combination include one or more cell, tissue, organ and or circulatory repair elements, including, but not limited to regenerative agents and restorative agents.

In one embodiment, one or more SBN elements and or SBN-related elements and in any combination include one or more therapeutic elements; diagnostic elements; prosthetic elements, and surgical elements, but not limited to, which elements may also be comprised of one or more SBN elements and or SBN-related, in whole or in part.

In another illustrative SBN embodiment, a therapeutic or disease preventive drug delivery system include, but is not limited to, one or more antibiotics, antibacterials, vaccines, antiviral and anti-parasitic drugs, cytostatics, vitamins, proteins and peptides, including enzymes and hormones and or other biological elements.

In another embodiment, one or more SBN element 100 include one or more elements having the capability to input, read, process, analyze, output and report on information gathered by various diagnostic, test, sensor, and assay elements.

In another illustrative embodiment, one or more SBN element 100 contain one or more in vivo or in vitro sensor systems, assay systems, and or therapeutic drugs in any combination to do real-time genetic-based (trait-based) and or phenotype (state-based) drug dosing to determine how an individual's external environment and or genotype and or phenotype affects the person's need and capability of metabolizing a drug, and thereby deliver the drug at optimally effective and safe doses.

Per one embodiment of the invention, in vivo and or in vitro assays for accurate drug dosing are custom tailored to the individual's phenotype, genotype, gender, and or other individual specific variables. One of the most important issues in clinical pharmacology that has not received sufficient attention in research, as well as in the day-to-day clinical care setting, is the remarkably large inter-individual variability in drug responses and side effect profiles. Such variability, which can be 40-fold or more, has been demonstrated with practically all classes of psychotropics, making it difficult to formulate rational guidelines for the dosing and the interpretation of biological parameters (such as the plasma or serum drug concentrations) that might be associated with therapeutic response. Although much remains unknown, a number of factors have been demonstrated to be important determinants of such variability. These include genetics, disease state, nutritional status, concurrent use of drugs, and other pharmacoactive substances, but also demographic factors such as age, gender, and ethnicity.

Regarding gender, little research has been conducted on the effects of psychotropic drugs on women. Most studies are done on laboratory animals. Animal research provides evidence that pharmacologic and pharmacodynamic differences exist between male and female animals when psychotropic drugs are used. However, few studies of this sort are performed with humans. Most drugs studied in humans involve young men, usually male medical students who volunteer to participate. However, differences exist between men and women in muscle mass and adipose tissue distribution, and all psychotropic drugs are lipophilic or fat-soluble. This is important because the higher fat-to-muscle ratio in women allows more drugs to be stored in body fat and prevent them from getting to the sites where they are active. Therefore, important differences exist and should be considered in terms of how psychotropic drugs should be administered. The reluctance of most pharmaceutical companies to include women in studies for new medications results from the desire to avoid the potential liabilities that may occur with women. There is a fear of litigation, particularly with respect to studies with women of childbearing age. Pharmaceutical companies are concerned about the potential for a lawsuit if a woman were to become pregnant and teratogenesis occurred.

In studies of drug use by women, the phases of the menstrual cycle are rarely taken into account. The menstrual cycle has dramatic effects on a woman's body, yet drugs are rarely given with consideration of this fact. Because the hormonal fluctuation encountered during the menstrual cycle may affect the outcome of studies with a particular drug, the desired positive effect might not result. Studies that test new drugs with women usually are conducted with postmenopausal women. Although elderly people often use drugs, high rates of anxiety and depression occur more frequently in women of childbearing age, yet psychotropic drugs are not studied adequately in the younger female population.

In one embodiment, in vivo and or in vitro response dosage adjustments are manipulated prior to introduction into the body, and or on the fly in the body per one or more factors affecting an individual, including such factors as, but not limited to, genotype, phenotype, disease state, metabolic state, nutritional status, concurrent use of drugs, and other pharmacoactive substances, and also demographic factors such as age, gender, and ethnicity.

One or more drugs within cage 106, cargo elements 102a-102f, and or vesicle 110 and their delivery may be manipulated and or dosages adjusted in vivo and post introduction into the patient by the use of, but not limited to, one or more sensor elements, assay elements, diagnostic elements, and patient data input and output elements. Such elements, contained in SBN element 100, may take one or more patient factors into account, and constitute a dynamic therapeutic delivery embodiment of the invention. Side effect profiles may also thereby be reduced.

In another embodiment, in vitro adjustments to one or more drugs within cage 106, cargo elements 102a-102f, and or vesicle 110, and their delivery and or dosage are manipulated and or formulated pre-introduction into the body to adjust various dosing parameters based on one or more individual factors and data, that may include one or more individual patient factors, which are manually input by a healthcare giver and or automatically determined by an apparatus known in the art, and constitute a pre-defined, static embodiment. Side effect profiles may also thereby be reduced.

In another embodiment, one or more dynamic and pre-defined static configurations are combined in one or more SBN element 100.

In one embodiment, cage 106 and or cargo elements 102a-102f and or vesicle 110 contain one or more patented drugs that are about to go off patent, and or have already gone off patent, and which drugs' efficacy may be beneficially altered and or enhanced by use of the invention. This beneficial change in efficacy may be achieved by the invention's ability to dynamically and or statically adjust the drug's responses and dosages arising from inter-individual variability due to one or more factors, such as, but not limited to, genotype, phenotype, disease state, metabolic state, nutritional status, concurrent use of drugs, and other pharmacoactive substances, and also demographic factors such as age, gender, and ethnicity of the patient. Side effect profiles may thereby be reduced. New patent filings for about to go off patent drugs and drugs already off patent may be enabled by this invention embodiment due to increased drug efficacy, and or by a better safety profile for the drug.

In another embodiment, cage 106, cargo elements 102a-102f, and or vesicle 110 may contain one or more non-gender specific drugs, and which drugs' efficacy may be increased, because drug responses arising from one or more inter-individual variability factors, such as, but not limited to, genotype, phenotype, disease state, metabolic state, nutritional status, concurrent use of drugs, and other pharmacoactive substances, and also demographic factors such as age, and ethnicity, are dynamically and or statically factored into the drug embodiment and its delivery. Side effect profiles may also thereby be reduced. New patent filings for new non-gender-specific drugs may be enabled by this invention embodiment.

In another embodiment, cage 106 and or cargo elements 102a-102f and or vesicle 110 may contain one or more gender-specific drugs, and which drugs' efficacy may be increased, because drug responses arising from one or more inter-individual variability factors, such as, but not limited to, genotype, phenotype, disease state, metabolic state, nutritional status, concurrent use of drugs, and other pharmacoactive substances, and also demographic factors such as age, gender, reproductive cycle state, muscle mass and adipose tissue distribution, hormone types and levels, and ethnicity, are dynamically and or statically factored into the drug embodiment and its delivery. Side effect profiles may also thereby be reduced. New patent filings for new gender-specific drugs may be enabled by this invention embodiment.

In one embodiment, one or more SBN elements and or SBN-related elements and in any combination include genetic agents, including, but not limited to proteins; peptides; DNA and DNA variants, RNA and RNA variants such as iRNA and siRNA, RNA-induced silencing complex (RISC) and other genetic-modifying agents.

In another illustrative SBN embodiment, therapeutic agent cargo elements may also contain one or more oligonucleotides in antisense therapy. These antisense DNA drugs work by binding to messenger RNAs from disease genes, so that the genetic code in the RNA cannot be read, stopping the production of the disease-causing protein.

In another illustrative SBN embodiment, therapeutic agent cargo elements may also contain one or more RNAi (RNA interference) elements and or RNAi variants such as small interfering RNA molecules (siRNA), but not limited to, that may collaborate with proteins in the cell and may form a complex called a RISC (RNA-Induced Silencing Complex). RNAi and or RISCs may be used to head off a genetic disease before the first symptom appears, based on an analysis of an individual's predisposition to certain diseases. This methodology is a way of silencing a specific gene, for example, genes that direct cancer cells to proliferate or that create overproduction of proteins that cause rheumatoid arthritis. Basically, RNAi works by scanning RNA templates that may cause a disease and cleaving that RNA template, and enzymes then destroying the template before it can complete its actions on the offending DNA. One of the key barriers to successful RNAi therapy is their finding their way to a specific site in the body and then the RNAi not degrading rapidly before it can do useful work. In one illustrative SBN embodiment, RNAi, siRNA and or RISC elements may be intelligently targeted by and sequestered within an SBN element such that the RNAi successfully seeks out and destroys potentially harmful genetic elements and or other genetic processes.

In another illustrative embodiment, one or more in vivo or in vitro cage 106, and or the cargo elements 102a-102f, and or vesicle 110, and or receptors 104a-104f, and or adaptors 108a-108f, and or triskelion 200, and or three-arms 202a-202c, and or heavy chain section 204a-204c, and or light chain section 206a-206c utilize the effects of chirality. Chiral molecules, which exist in pairs of stereoisomers, are like a pair of hands, where one form is left, the other right. These two stereoisomers or enantiomers are structurally identical, with the same physical properties, differing only in their three-dimensional spatial arrangement. Just like a pair of hands, they are non-superimposable mirror images and have no planes of symmetry, and are described as R and S form. If a plane of polarized light is passed through a sample of each enantiomer, one will rotate the light to the left (levorotatory or (−)-enantiomer), and the other to the right (dextrorotatory or (+)-enantiomer). If the light is passed through a 50:50 mix, no rotation would be observed: this mixture is racemic and optically inactive. Confusingly, the rotation of the plane of polarized light does not always equate to the absolute configuration of the molecule, so the terms R and S are not necessarily equivalent to (−) and (+).

For example, drugs work by reacting with receptors in the body that have a specific physical shape. Going back to the hand analogy, these receptors can be viewed as gloves, and one 'hand' will fit better into this 'glove', or active site. If both enantiomers are able to fit the receptor, the binding will be less tight and therefore the drug will be less active. Using the more active isomer of a drug has several advantages:

- It leads to opportunities for 'racemic switching', whereby a drug that has previously been marketed as a racemate can be re-developed and introduced as its optically active form. This is a useful for companies wishing to extend the patent protection of a key product
- It provides a means to double drug manufacture by switching production from the racemate to the pure enantiomer
- Less waste will be produced from avoiding having to manufacture the unwanted isomer
- The dosage given to a patient will be automatically halved
- There is less likelihood of side effects from the unwanted isomeric form.

One or more of the chirality features and benefits listed above may be applied, in one embodiment, to cage 106, cargo elements 102a-102f, vesicle 110, receptors 104a-104f, adaptors 108a-108f, triskelion 200, three-arms 202a-202c, heavy chain section 204a-204c, light chain section 206a-206c, ligands, targeting moieties, and or vectors.

According to another feature, the self-assembling proteins that make up the cage 106 naturally shields the cargo elements contained within the cage 106 from electron charge transfers and prevent distortion of the cage 106. Such charge transfer and structure distortion would make cage 106 unsuitable for reliable operation. Thus, the cage 106 shields cargo elements 102a-102f, and or vesicle 110, consequently reducing the tendency of the system towards structural distortion and improper functioning. The shielding properties of the cage 106 also inhibit adverse charge transfer interactions between various cages and their respective cargo.

According to one feature, the natural shielding capabilities of the cage 106 allow for direct molecular or chemical bonding of suitable cargo elements to the cage 106 without causing distortion of the cage 106, as exemplified by the non-distorting bonding of the adaptors 108a-108f and the receptors 104a-104f to the cage 106.

In one embodiment, one or more elements may be bonded, fastened, and or affixed (hereinafter, "bonded elements") to SBN elements by one or more means, for example, but not limited to, by being included in a modified protein sequence of one or more elements comprised of cage 106, receptors 104a-104f, adaptors 108a-108f, cargo elements 102a-102f, and or vesicle 110 and or bonded elements, and or attached via a cysteine residue and or optional further spacer, and or by covalent bonding, site directed mutagenesis, cysteine residues, genetically engineered mutation and or modification, peptides, proteins, DNA, antibodies, and monoclonal antibodies, and via other bioengineering techniques known in the art.

In one embodiment, one or more elements comprised of cage 106, receptors 104a-104f, adaptors 108a-108f, cargo elements 102a-102f, and or vesicle 110 and or bonded elements are self-directing, self-assembling, self-repairing, self-regenerating, and or self-replicating.

In one embodiment, one or more elements comprised of cage 106, receptors 104a-104f, adaptors 108a-108f, cargo elements 102a-102f, and or vesicle 110 and or bonded elements are self-adapting and or self-regulating.

In another illustrative embodiment, cage 106, and or cargo elements 102a-102f, and or vesicle 110, and or element 100 and or bonded elements are coated in whole or in part with chemical elements, materials, and or substances that are natural and or synthetic.

In one embodiment, one or more SBN elements and or bonded elements, and in any combination are internally and or externally coated or treated in whole or in part with surfactants, including, but not limited to, surfactant agents selected among soy-bean phosphatidylcholine, dioleyl phosphatidylcholine, dipalmitoyl phosphatidylcholine, hydrogenated soy-bean phosphatidylcholine, phosphatidylethanolamine and phosphatidylserine), and or with cosurfactants, including, but not limited to cosurfactant agents selected among ethanol, propanol, isopropanol, butanol, sodium taurocholate, sodium glycocholate, propylene glycol, butyric acid and benzoic acid);

In one embodiment, one or more SBN elements and or SBN-related elements, and in any combination, are internally and or externally coated or treated in whole or in part with steric stabilizers including, but not limited to, steric stabilizers selected among dipalmitoyl phosphatidyl ethanolamine-PEG, PEG-stearate, the esters of the fatty acids from the myristic acid to the docosanoic acid with methyl ether PEG, the diacylphosphatidyl ethanolamines esterified with methyl ether PEG and the polylactates and the polyglycolactates esterified with methyl ether PEG.

In one embodiment, one or more SBN elements and or SBN-related elements and in any combination include nanoparticle elements such as, but not limited to, polymer-based, polybutylcyanoacrylate-based, and cetyl alcohol-based nanoparticles, empty cage Fullerenes, endohedral Fullerenes and carbon nanotubes, cells, liposomes, and micelles.

In one embodiment, one or more SBN elements and or SBN-related elements and in any combination include sensor elements, including, but not limited to, radioactivity sensors; chemical sensors; biological sensors; electromagnetic sensors; acoustic sensors; visible, infrared, and or ultraviolet wavelength sensors; tactile sensors; pressure sensors; volumetric sensors; flow sensors; and temperature sensors.

In one embodiment, self-assembling empty cage 106 elements and or cage 106 and or cargo elements 102a-102f and or vesicle 110 and or receptors 104a-104f and or adaptors 108a-108f and or bonded elements are configured to operate in harsh and or demanding environments.

In one embodiment, self-assembling empty cage 106 elements and or cage 106 and or cargo elements 102a-102f and or vesicle 110 and or receptors 104a-104f and or adaptors 108a-108f and or bonded elements are radiation hardened, and or radio frequency (RF) shielded, and or thermally shielded, and or chemically shielded, in whole or in part, and in any combination.

According to one embodiment, cage 106, and or the cargo elements 102a-102f, and or vesicle 110, and or receptors 104a-104f, and or adaptors 108a-108f, and or triskelion 200, and or three-arms 202a-202c, and or heavy chain section 204a-204c, and or light chain section 206a-206c may use an in vivo and or in vitro reservoir of unassembled SBN materials, cargo element materials and or bonded element materials to re-supply, reassemble and or regenerate defective and or destroyed and or inoperable SBN elements and or bonded elements.

In one embodiment, one or more functionalization elements and in any combination, are bonded and or tethered and or otherwise incorporated into one or more SBN elements, including functionalization elements such as, but not limited to, nano-lasers, quantum dots; photonic dots; nanoscale DNA chips; protein assay chips; assay elements; environmental, protein, phenotype, DNA, and or metabolic assay and analysis elements.

In another illustrative embodiment, cage 106, cargo elements 102a-102f, and or vesicle 110 contain one or more biodegradable in vivo and or in vitro asymmetric resonant cavity (ARC) high-Q ("whispering gallery mode") nano-lasers, wherein lasing of the contained nanostructure is triggered by appropriate deformations of the nanocavity, which deforming forces may be mechanical, acoustic, sonic, chemical, biochemical, biological, metabolic, covalent, non-covalent, ionic, photonic, sonic, thermal, fluidic, electromagnetic, magnetic, radioactive, or electrical, but are not limited to such forces.

The highest Q optical resonators are dielectric microspheres or nanospheres in which the high Q modes are created by a total internal reflection of light circulating just inside the sphere. These high Q modes are known as whispering gallery modes or alternatively as morphology-dependent resonances. If the dielectric is a liquid droplet containing an appropriate dye then the droplet acts as a high Q micro- or nano-resonator to support lasing action when optically pumped.

The Q factor within the microsphere or nanosphere remains high up to a critical deformation and then decreases rapidly. Beyond this critical deformation, the laser light emission from the deformable microcavity or nanocavity becomes highly directional and controllable. This ray optics model for deformable droplets has evolved to generally describe the spoiling of the high-Q (whispering gallery) modes of deformable ring-shaped cavities as they are deformed from perfect circularity. A sharp threshold has been found for the onset of Q-spoiling as predicted by the KAM theorem of non-linear dynamics. Beyond a critical deformation the escaping light emerges in certain specific directions that may be predicted. The deformations considered can be quite large, ranging from 1-50% of the undeformed radius, assuming that they maintain the convexity of the cavities. Such "asymmetric resonant cavities" (ARC) possess unique advantages, such as:

1. The ability to tune the Q-value and resonant frequency of the ARC by appropriate deformations.
 2. When deformed in situ, designing a Q-switched ARC laser.
 3. The ability to couple a high-Q/WG mode out of the ARC with strong directionality.

But whispering gallery ARC lasers in the prior art have two drawbacks. First, due to excessive internal reflection, they emit only a few microwatts of optical power. Second, the direction of the emitted light is not well defined. However, it was demonstrated both experimentally and computationally in later art that for high-index semiconductor materials (index of refraction n >2), the WG modes may not be relevant to the lasing properties of the cavities. Rather, above a critical deformation level, the light pulses travel in a bow-tie pattern rather than operating in the "whispering-gallery" mode of circular microlasers. The resonant modes of "bow-tie" shapes suffer less internal reflection and emit light in four narrow, controllable beams and are responsible for the improved performance of the lasers in the presence of large geometric deformations. These lasers emit light in specific directions.

A new type of semiconductor microlaser was developed in the art that was a dramatic improvement over earlier related lasers by using better resonator optics, chaos theory, semiconductor quantum-engineering. Demonstrated was a peak power output increase by several orders of magnitude (from ~10 mW to ~10 mW) and with output directionality than that obtained from a non-deformed (circular cylindrical) laser or previous conventional circular QC-disk lasers by fabricating them in a geometry that is smoothly deformed from circular symmetry. These lasers are, in fact, quadrupolar; that is, they have a circular cross section that has been elongated in one direction and squeezed in the perpendicular direction. At small deformations this results in chaotic whispering-gallery resonances, which are explained below. At larger deformations the lasers operate on bow-tie-shaped modes that are completely new to these little resonators and are highly advantageous. It is in the changing of the edges of the figure that creates different patterns, and the more complex the figure the more complex the patterns. Thus, geometry affects the expression of laser light.

A new parameter for laser design was thus introduced into the art: deformation of the resonator. In conventional lasers, the output power depends on the resonator length, whereas here the power increases exponentially with deformation. It is remarkable that the transition from whispering-gallery modes to bowtie modes appears at certain deformations where simultaneously the spectral properties are also improved.

The optical physics of such resonators is nontrivial and interesting because the ray dynamics in such a case is partially chaotic, and standard real-space ray tracing is not helpful in analyzing their properties. Instead, phase-space methods taken from nonlinear classical dynamics such as the surface-of-section method have allowed a much clearer picture of the physics, leading to qualitative predictions for the high-intensity emission directions from quadrupole-deformed ARCs.

A surprising observation has also been reported in the art of directional tunneling escape from nearly spherical fused silica optical resonators, in which most of the phase space is filled with nonchaotic regular trajectories. Experimental and theoretical studies in the prior art showed that 2-d "chaotic" modes dominated the lasing emission, which had been previously argued but not experimentally shown. However, later prior art showed the droplet shape deformation was not controlled and could not be manipulated to turn the effect on and off.

The latest work in the art shows shapes that are quadrupole, elliptical, and hexadecapole ARCs. In other art, 2-d "chaotic" modes were experimentally shown, and shape deformation was also controlled using shaped polymer micro-cavity lasers.

Other work in the art has also found the following: (1) there is a remarkable and reproducible difference in the lasing emission patterns from ARC lasers with very similar boundary shapes. (2) The basic difference between chaotic (quadrupole) and nonchaotic (elliptical) ARC emission patterns is in agreement with the predictions based on the adiabatic model. (3) Nonetheless, the persistence of highly directional emission patterns for highly deformed quadrupolar ARCs is inconsistent with the adiabatic model and is a quite surprising experimental discovery. (4) A new theoretical model attributes the high-emission directions observed for the chaotic shapes to the flow pattern produced by the unstable manifolds of short periodic orbits; this flow pattern differs significantly from the adiabatic model. This model was shown to explain both the persistence of narrow emission peaks in the quadrupole at high deformation and the major shift in emission directionality at large deformation for ARCs with hexadecapole deformation. It also predicts that completely chaotic boundary shapes, such as the stadium, can nonetheless exhibit highly directional emission.

In one embodiment, the invention will replicate and improve upon ARC laser models and methods known in the art, by uniquely and for the first time with a controlled series of boundary shapes for ARC organic dye nanolasers comprised of deformable liquid droplets enclosed in vesicle 110, which is encapsulated (hosted) in a protein-based cage 106, forming a biodegradable, biomolecular guest-host optical system. Further, the entire biomolecular system automatically self-assembles at the nanoscale. Optical pumping of this novel ARC nanolaser is provided by various means known in the art.

In one ARC embodiment, the geometry of enveloping cage 106 is manipulated by varying pH that in turn can determine the geometry of the enclosed nanodroplet (vesicle 110). In another ARC embodiment, Clathrin coated pits are formed by controlled geometric aggregation of cage 106, which exerts certain conformational (deformational) forces on the vesicle 100, and hence on the encased nanodroplet. In another ARC embodiment, conformational changes in lipid bilayers produce conformational changes in cage 106 cage, and thus give additional control, by inclusion or exclusion of these forces, over the SBN platform and the cross sectional shape and geometry of the nanodroplet encased in vesicle 110. Any changes in the conformation of lipids in the membrane of vesicle 110 changes the multiple physical attributes of the membrane. E.g., vesicle 110 membrane properties such as membrane fluidity, bilayer thickness, surface charge distribution, and lateral pressure effect the structure and function of intrinsic membrane proteins within vesicle 110. Membrane interactions can also be induced in vesicle 100 due to thermal fluctuations, and such interactions are known as entropic interactions. Membrane induced interactions are generally long-range interactions and may also influence the phase behavior of membrane proteins in vesicle 110, even if stronger short-range interactions are present. Mechanical forces may also act on vesicle 110 membranes. Hydrodynamic forces, viscous forces and thermal forces may also be utilized in various ARC embodiments. In another ARC embodiment, acoustic or sonic forces act on the cage 106 and or vesicle 100, thereby deforming them sufficiently to create an ARC nanolaser.

In a preferred ARC nanolaser embodiment, a dyed droplet with or without additive scattering particles is contained within a cavity forming, non-permeable element 110, which may be comprised of biological elements and or non-biological elements and that may be biodegradable in whole or in part. The non-permeable cavity forming element 110 may be comprised of, for example, but not limited to, lipids, micelles, caspids, macrophages, blood cells and other biological and chemical elements, as well as biodegradable materials made of bio-base materials such as, for example, biodegradable plastics and films, and also biodegradable polymers like that composed of OPLA® (Open-cell PolyLactic Acid). In another ARC nanolaser embodiment, the non-permeable cavity-forming element 110 may utilize molecular-imprinted materials.

In one embodiment, forces, for example, photonic, mechanical, fluidic, thermal, sonic, or electromagnetic, but not limited to, deform the cavity forming elements 110. Accordingly, the dyed droplet carried within the cavity-deforming element 110 is also deformed, and the so deformed droplet becomes a deformable high-Q optical resonator. Photons resonate within the deformed droplet cavity. At critical deformations that tune the Q-value and resonant frequency of the droplet cavity, lasing occurs, and stimulated light emissions from the droplet are released in a highly directional and controlled manner from the droplet and escape from the cavity element 110 and cage 106.

In one embodiment, the result is a Q-switched ARC droplet nanolaser that provides a room temperature, ultralow-threshold, highly controllable, strongly directional, ultrabright laser light source device that operates at the nanoscale, and also features the capability to store light.

An alternative illustrative embodiment of the ARC nanolaser uses a cavity forming element 110, but substitutes the dyed liquid droplet with an "ARC photonic dot", which is comprised of one or more quantum dots contained in the high-Q three-dimensional nanocavity of the cavity forming element. Selectable quantum dot energy level emissions and/or cavity deformation precisely excite the whispering gallery modes in the cavity-forming element.

In one embodiment, various calculated critical deformations of the cavity forming element and/or at specific quantum dot energy emissions may also assist in tuning the Q-value and resonant frequency of the ARC photonic dot, lasing occurs and stimulated light emissions from the ARC photonic dot are released in a highly directional and controlled emission manner from the cavity forming element 110 and cage 106. In one embodiment, the Q-switched ARC photonic dot provides a room temperature, ultralow-threshold, highly controllable, ultrabright laser light source device that operates at the nanoscale, and also features the capability to store light.

In another ARC laser embodiment, a droplet ARC nanolaser and a photonic ARC nanolaser are combined to create a hybrid droplet/photonic dot ARC nanolaser.

In one illustrative SBN embodiment, one or more ARC nanolasers are used as the excitation light source for one or more non-ARC related quantum dots and or photonic dots bonded, attached, or tethered to one or more SBN elements, and one or more quantum dots and or photonic dots may be illuminated and made to fluoresce by using one or more ARC nanolaser beams.

In another ARC laser embodiment an ARC nanolaser may be coated with one or more surfactants and or cosurfactants.

In another ARC laser embodiment, an ARC nanolaser may be conjugated with one or more other elements, materials, and substances.

In another ARC laser embodiment, an ARC nanolaser may be self-replicating, self-repairing, self-adaptive, self-regenerating, self-regulating, and or self-regenerating.

In one ARC laser embodiment, geometrically derived algorithms such as graphs and Lie algebras, including Clifford algebras, and or biological control laws produce one or more ARC laser elements with certain desired properties and capabilities.

In another ARC laser embodiment, an ARC nanolaser use a reservoir of unassembled SBN materials to furnish, repair, reassemble, and or to regenerate one or more new ARC nanolaser and or nanolaser elements in the event one or more ARC nanolasers and or nanolaser elements become defective, destroyed, and or otherwise inoperable.

Optical pumping of the dyed droplet and or excitation of a quantum dot is done through methodologies known in the art. Outgoing light from the cavity-forming element can be directed and controlled through methodologies known in the art.

In another ARC laser embodiment, an ARC nanolaser comprise a platform comprised of one or more ARC nanolasers elements and or non-ARC nanolaser elements.

In another ARC laser embodiment, an ARC nanolaser functionality and operation follow and or are governed by internally and or externally directed behaviors, e.g., via pulsed ultrasound.

In one illustrative SBN embodiment, one or more ARC nanolasers are coated in reflective and or non-reflective coatings in whole or in part.

In another embodiment, one or more ARC nanolasers are used in vivo or in vitro for precisely destroying one or more structures within a specific cell, constituting an intra-cellular nano-surgery system.

In one embodiment, the invention comprises a sonodynamic therapy method, in which non-thermal ultrasound is used causing one or more in vivo ARC nanolasers to deform and to emit coherent light, thereby destroying specific cells at specific locations in the body. In one illustrative sonodynamic embodiment, ultrasound transducer-tipped catheters are used to deform one or more ARC nanolasers and trigger in vivo lasing at precise locations in the body.

In another illustrative embodiment, one or more ultrasound devices with ultrasound transducers implanted in transdermal patches are used to deform one or more ARC nanolasers and trigger in vivo lasing at precise locations in the body.

In another illustrative sonodynamic embodiment, ultrasound echo contrast microbubbles may be used to deform one or more ARC nanolasers and trigger in vivo lasing. The microbubbles reached by an ultrasound signal resonate with a specific frequency depending on microbubble diameter and act as echo enhancers, producing acoustic impedance that is very high—the shock wave is high enough to deform an ARC nanolaser. However, the main resonance frequency is not the only resonance frequency of the bubble itself and multiple frequencies of the fundamental one are emitted, just like in a musical instrument. The advantage of the harmonic over the fundamental frequency is that only contrast agent microbubbles resonate with harmonic frequencies, while adjacent tissues do not resonate, or else their harmonic resonation is very little. In another embodiment, a powerful ultrasound beam is used that cause contrast agent microbubbles to explode, producing a strong and very short backscatter echo. In one embodiment, microbubbles may be "tuned" in vivo to elicit different deformations of one or more ARC nanolasers, thereby producing different light wavelengths for different imaging, and diagnostic or therapeutic purposes.

In another embodiment, in vivo or in vitro cage 106, cargo elements 102a-102f, and or vesicle 110 may simultaneously comprise a lasing and a non-lasing structure.

In one embodiment, one or more quantum dots and or photonic dots known in the art are utilized, and are bonded, attached, or tethered to cage 106, cargo elements 102a-102f, receptors 104a-104f, adaptors 108a-108f, triskelion 200, three-arms 202a-202c, heavy chain section 204a-204c, light chain section 206a-206c, and or to one or more bonded elements, and or to one or more ligands, targeting moieties, and or vectors, and or are contained within vesicle 110.

Because quantum dots are only about one to ten nanometers in size, their electrons are compacted, causing them to emit light or to act as a fluorescent tag. One of the key advantages of quantum dots is their ability to act as broadly tunable nano-emitters that are excitable with a single wavelength light source. Using an available quantum dot spectrum of one or more colors known in the art, in addition to one or more quantum dot colors in the infrared spectrum it is possible to finely tune quantum dots by, for example, slightly varying the size of quantum dot. The size of the dot controls its emission color, e.g., 2 nm quantum dots luminesce bright green while 5 nm quantum dots luminesce red.

In one embodiment, one or more types of light sources known in the art activate one or more quantum dots and or photonic dots.

Quantum dots known in the art have characteristics that are more desirable than fluorescent dyes. Dyes fade quickly, can be toxic to cells, and cannot be used together because each dye requires a different light wavelength to be visible. Quantum dots fluoresce or stay lit much longer then dyes, and as previously noted, one or more different wavelength quantum dots are excitable with a single wavelength light source. In one embodiment, quantum dots are bonded chemically to biological molecules and become bioconjugated nanoparticles. In one SBN embodiment, one or more fluorescence-quenching molecules are conjugated to one or more quantum dots to enable the on/off fluorescent detection of a specific target in vivo or in vitro. When conjugated to biological molecules known in the art that can quench their fluorescence, fluorescent quantum dots can be made, for example, to stick to the surfaces of, or to be taken up, for example, by specific bacteria, proteins, or cells. For example, adenine, quanine and tryptophan quench all fluorescence from green-emitting quantum dots, and quench more than 80 percent of the fluorescence from red emitting quantum dots. Once the conjugated quenching molecule is removed from the quantum dot by active enzymes on or in a bacterium or cell the quantum dots once again fluoresce, thereby enabling a photonic-based detection system.

In one SBN embodiment, quantum dots are tagged to proteins in vivo and or in vitro and their specific wavelength glow enables the identification of specific pathologies, disorders, metabolic states, proteins or DNA making it possible to diagnose various diseases. Because quantum dots glow with bright fluorescent colors, they improve the sensitivity of diagnostic tests for molecules that are difficult to detect, such as those in cancer cells, or even the AIDS virus. For example, it is possible to tell how much protein is on each cell by the amount of light transmitted in a particular emitted color. In one embodiment, a change in the concentration of proteins on each cell may be an early indication of cancer. In another SBN embodiment, one or more tags trace specific proteins in cells for cancer diagnosis or monitor the effectiveness of drug therapy in vivo or in vitro.

In one embodiment, quantum dots and or photonic dots are freely released in vivo or in vitro from cage 106, and or from cargo elements 102a-102f and or from within vesicle 110. Cells will incorporate any quantum dots known in the art that underlie them and cells will ingest all the dots they pass over. This particular embodiment thereby provides a convenient and rapid way for assessing the cells' potential to metastasize, or spread (as a cancer) from one part of the body to another. Because the quantum dots go into cells as "inert spectators," the dots have no discernible effect on cells. The cells remain healthy and even continue to divide, with each cell division reducing the number of dots in any given cell.

In vivo quantum dots in some of the art have been limited by difficulties in obtaining nanocrystals that are biocompatible. To address this problem, in one SBN embodiment, one or more quantum dots are encapsulated in one or more materials or substances known in the art, such as, but not limited to, phospholipid block-copolymer micelles, which render the quantum dots suitable and safe for in vivo use.

In another illustrative embodiment, cage 106, and or cargo elements 102a-102f, and or vesicle 110 contain one or more quantum dots and or photonic dots that are coated in whole or in part in one or more surfactants and or cosurfactants, other materials, and or substances.

In one SBN embodiment, one or more different sized quantum dots, and or photonic dots, are used as one or more contrast markers in magnetic resonance imaging (MRI), in positron emission tomography (PET) for in-vivo molecular imaging, or as fluorescent tracers in optical microscopy.

In one SBN embodiment, one or more nanoscale quantum dot assays using tiny permutations of color tag a million or more different proteins or genetic sequences in a process called multiplexing. In one embodiment, one or more quantum dots of various sizes are excited at the same wavelength but have different emission wavelengths, and act as probes in experiments where multiple fluorescent measurements need to be made simultaneously, such as flow cytometry or confocal microscopy.

In another embodiment, one or more LuxR proteins and lux bioluminescence genes and or other luminescent causing genes known in the art are utilized and are bioengineered and incorporated into cage 106, cargo elements 102a-102f, vesicle 110, receptors 104a-104f, adaptors 108a-108f, triskelion 200, three-arms 202a-202c, heavy chain section 204a-204c, light chain section 206a-206c, bonded elements, ligands, targeting moieties, and or vectors, which may also be conjugated with one or more other elements, materials, and substances.

Bioluminescence is turned on by the presence of certain diseases, disorders, metabolic states, pathogens, toxins, genotypes and phenotypes, as well as chemical, nuclear, and biological elements and activities, but not limited to such.

Bioluminescence light-emitting reactions are quite distinct for different organisms, with the only common component being molecular oxygen. Therefore, significant differences have been found between the structures of the luciferases and the corresponding genes from one luminescent organism to another. These distinctive properties may be manipulated via bioengineering techniques known the art to produce distinctive bioluminescence SBN embodiments.

According to one illustrative embodiment, luxA and luxB genes encode the a and b subunits of luciferase (a heterodimer in the form ab). The luxCDE genes code for polypeptides (transferase, synthetase, and reductase) that are required for the conversion of fatty acids into the long-chain aldehyde required for the luminescent reaction. The aldehyde is formed when an acyl group that was transferred from the synthetase to the reductase is reduced with NADPH. Beforehand, the fatty acid was activated by synthetase to form acyl-AMP, which in turn reacts with a specific cysteinyl residue located close to its carboxyl terminal. Acylation of the synthetase, in contrast to acyl-AMP formation, occurs efficiently only when the synthetase is bound to the reductase subunit. The fatty acid activated by the synthetase was formed when the transferase accepted the fatty acyl group onto a serine residue from acyl-ACP, acyl-CoA, and other acyl donors followed by the transfer to water or other acceptors. The cleavage, activation, and reduction of fatty acyl groups to form fatty aldehyde are highly specific for substrates with chain lengths of 14 carbons, providing strong evidence that tetradecanal is the natural substrate for the bioluminescent reaction.

According to one illustrative embodiment, bioluminescence LuxR proteins and genes work in the following manner, e.g., in bacteria:

Two lux operons: luxR (left) and luxICDABEG (right) are both controlled by the same operator luxI—VAI (diffusible autoinducer) synthase.

LuxR is able to activate transcription of lux operon in the presence of sufficient VAI (10-9M).

lux box—20 bp inverted repeat 40 bp upstream of transcription start site.

luxR and luxI mediate cell-density response.

Low density—luxI transcribed at basal levels.

High density—luxI transcription activated by LuxR-VAI interaction.

LuxR is able to both positively and negatively autoregulate its expression.

Low VAI conc.—positive autoregulation.

High VAI conc.—negative autoregulation.

Positive—requires VAI and LuxR binding to lux box to activate transcription of both operons.

Negative—requires VAI, LuxR, lux box and DNA sequences within the luxI operon that are upstream of the promoter for luxI operon.

All known chromosomal examples of repression at a distance in prokaryotes involves operons that are regulated by cAMP-CRP.

LuxR—requires GroEL and GroES for folding into active conformation so activated by stress (heat shock, starvation) and or requires cAMP-CRP for activation so affected by catabolite repression. The transcription is repressed by iron, so in low iron conditions there is very high luminescent activity.

luxICDABEG—positively regulated by LuxR; negatively regulated by LexA (like SOS genes); positive autoregulation by LuxI LuxR superfamily—proteins similar to C-terminus of LuxR (sites of DNA-binding and transcriptional activation).

LuxR family—proteins similar to all of LuxR.

Summary:

LuxR
- Transcription activated by cAMP-CRP
- Transcription repressed by iron
- Transcription repressed by LuxR-AI complex (negatively autoregulated)
- Protein folded into active conformation by GroEL and GroES (stress proteins)
- Interaction of LuxR and Al is either direct or indirect (signal transduction)

luxI Operon
- Transcription activated by LuxR-AI complex
- Transcription repressed by LexA
- Basal-level transcription at low cell densities
- Maximal transcription at high cell densities
- "Quorum Sensing"

(Quorum—the minimum number of members required to be present before an assembly can transact business. A minimum behavioral unit.)

In one embodiment, luminescent causing genes provide optical pumping sufficient to excite one or more in vivo and or in vitro quantum dots and or photonic dots.

In one SBN embodiment, gold metal nanoparticle probes with sensor ligands and using electrical charges are bonded to cage 106, and or be cargo elements 102a-102f, and or are contained within vesicle 110, and or attached to receptors 104a-104f, adaptors 108a-108f, triskelion 200, three-arms 202a-202c, heavy chain section 204a-204c, light chain section 206a-206c, bonded elements, and or be attached to ligands, targeting moieties, and or vectors. The gold particles carry short strands of artificial DNA (oligonucleotides) tailored to match known segments of biological DNA that are implicated in, or linked to, disease. The oligonucleotides, made up of 24 bases, are attached to the gold particles, about 13 nanometers (13×10-9 m) in diameter, via a sulfur atom. When such a molecule probe finds its target DNA, the two interact and the result is the formation of a polymeric cluster that affects its plasmon resonance, and there is a color change from red to blue. The color change is reversible and the temperature at which this occurs is quite specific, much more so than with conventional DNA mutation probes, again offering a sensitivity that adds to the certainty of correct identification. This "melting transition" can be monitored at 260 or 700 nm. This one-pot color-change method can identify the target even when it is in the presence of other strands with base imperfections. The method is so sensitive that in one embodiment it can detect a mutant strand of DNA that has one wrong base, regardless of where the rogue base is located. In one embodiment, gold nanoprobes may be utilized as diagnostic sensors in vivo and or in vitro. In another embodiment, the color change and light emissions are sufficient to optically pump an in vivo and or in vitro ARC nanolaser, a quantum dot, photonic dot, and or a photosensitive liposome, lipid, or cellular membrane or other photosensitive material.

In one embodiment, optical pumping and excitation of one or more in vivo or in vitro ARC nanolasers is done via one or more quantum dots, photonic dots, genetically engineered proteins using LuxR proteins and lux bioluminescence genes, and or gold metal nanoparticle probes with sensor ligands and using electrical charges, but not limited to such.

In another embodiment, one or more ARC nanolasers, genetically engineered proteins using LuxR proteins and lux bioluminescence genes, and or gold metal nanoparticle probes with sensor ligands and using electrical charges, hereinafter, "Light Sources", but not limited to such photonic sources, produce light or luminesce in the presence of one or more chemicals, toxins, biological agents, radioactive elements, various diseases such as cancer and HIV, various genotypes, phenotypes, environmental elements, different metabolic actions and states, various cell types, various proteins, and or by encountering blood clots, but not limited to.

In another illustrative in vivo or in vitro embodiment, one or more SBN element 100 and Light Sources are used as fluorescent probes in biological staining and diagnostics, including, but not limited to, fluorescence detection of target molecules in cell biology, biochemistry, analytical chemistry and genetics, with additional applications in DNA sequencing, real-time PCR assay, flow cytometry, cell sorting, enzyme-linked immunoassays, ligand-binding assays and laser-scanning confocal microscopy.

In one illustrative embodiment, one or more SBN element 100 contain one or more Light Sources that are tuned to specific wavelengths, for example, to wavelengths that detect and or destroy certain kinds of one or more diseased cells.

In another SBN embodiment, one or more SBN element 100 and Light Sources are used in vivo or in vitro for precisely destroying one or more blood clots.

In one SBN embodiment, light emissions from one or more sources of photons, for example, but not limited to, Light Sources provide optical pumping sufficient to excite an ARC nanolaser in vivo or in vitro. The resulting ARC laser emissions and local tissue heating cause agents trapped in one or more thermally sensitive cargo elements 102a-102f and or vesicle 110 to be triggered and released, thereby forming a targeted agent delivery system. Diagnostic and therapeutic agents may be simultaneously delivered via this site-specific delivery embodiment by using one or more thermally sensitive cargo elements 102a-102f and or vesicle 110.

In one illustrative SBN embodiment, one or more SBN element 100 and Light Sources form a photodynamic therapy (PDT) system for cancer treatment, whereby a drug or dye is administered to the patient either intravenously or by injection. The drug travels through the blood stream and localizes on cancer cells. After an appropriate time (24-78 hours) the localized drug is activated with one or more Light Sources. The drug destroys the cancer cells, while leaving the normal tissue intact.

In one PDT embodiment, drugs are localized on cancer cells, and this singlet oxygen reacts with the cancer cell, killing it. The accepted mechanism for PDT involves the interaction of an excited state of the drug or dye with the ground state of oxygen. A molecule of the drug absorbs a photon of red light and is excited to the first excited singlet state. If this singlet state is long lived energy can be transferred from the singlet state to the triplet state through interstitial crossing. This triplet state can react with local oxygen molecules created by an excited state of oxygen called singlet oxygen. Singlet oxygen is cytotoxic and destroys nearby cells.

There may be one of two mechanisms by which singlet oxygen can attack a cell, according to the type of PDT embodiment. In one PDT embodiment, the drug is localized on the outside of the cell membrane, and the singlet oxygen destroys the micro vascular of the cell, and the cell dies due to lack of oxygen. In another PDT embodiment, the dye is left for a longer period of time before light activation, and the dye may permeate the cell membrane and attack the mitochondria of the cell, leading to programmed cell death or apotosis.

In a two-photon PDT embodiment, multiphoton excitation is made possible by using the high peak power of a femtosecond laser source. Two-photon excitation allows low average power IR radiation to be used for excitation. This results in two key benefits: 1) deeper penetration depth of light, 2) new PDT treatments of skin melanoma without the addition of a drug or dye.

In another illustrative SBN embodiment, one or more SBN element 100 and one or more Light Sources may be a light source for use in a photodynamic therapy (PDT) system for age related macular degeneracy (AMD).

In one illustrative embodiment, SBN embodiment, one or more SBN element 100, bonded elements, and or Light Sources include one or more nanoscale passive and or active linear or nonlinear optic components and/or particle detectors and/or other cargo sufficient to implement in vivo or in vitro optical system arrays.

In another illustrative SBN embodiment, one or more SBN element 100 and or Light Sources are sufficient to implement in vivo or in vitro genetic and protein nanoscale optical biological assay systems. In one illustrative configuration, one or more SBN elements contain one or more nano-scale DNA chips known in the art, and or one or more nano-scale DNA chips known in the art to detect DNA samples formed from bonding with the target DNA on a chip, and or reference DNA nano-chips. In another embodiment, DNA chips are implemented via SBN elements in whole or in part.

In another illustrative configuration, one or more SBN elements 100 contain one or more nanoscale protein array techniques known in the art. The array surfaces are designed to bind to one or more hydrophobic, hydrophilic (cation or anion) or specific ligands, and also include a protein array reader known in the art. In one embodiment, nanoscale protein arrays are implemented in whole or in part via SBN elements.

In another illustrative embodiment, one or more SBN elements 100 and or one or more Light Sources are used in a multiplexed analysis system that provides a nanoscale replacement for DNA-chip technology and can be used in vivo and or in vitro for the analysis of genetic variance, proteomics, and gene expression.

In another SBN embodiment, one or more SBN 100 element and or one or more Light Sources are used in vivo or in vitro and act as detection, diagnostic and tracking agents for chemical, biological, and or nuclear elements and activities, but not limited to such.

In another embodiment, one or more Light Sources in one or more SBN element 100 produce specific light emissions and or thermal energies caused by their coming into contact with a particular metabolic state, medical disorder, disease pathology, genotype, phenotype and or other specific stimuli, and one or more entrapped agents are thereby selectively triggered and released from cage 106, cargo elements 102a-102f and or vesicle 110. In doing so, they form a targeted agent delivery system without exposing the entire body—or an indiscriminate area—to a similar dose of light, thermal energy, and or agents. The agents may be delivered in vivo by means known in the art.

In one illustrative embodiment, photonic energies from one or more Light Sources thermally operate on sequestered cargo elements 102a-102f, and or vesicle 110 that may have one or more entrapped materials, such as, but not limited to, therapeutic, diagnostic, and or therapeutic agents within an aqueous interior, and or that may have one or more entrapped nanoparticles such as liposomes, micelles, proteins, other biological and or bioengineered elements, including organic, inorganic, and synthetic materials, and or that may have one or more hydrophobic materials bound to a lipid bilayer membrane. The well-known permeability increase at the phase transition temperature provides a means to trigger release of an entrapped agent, like a therapeutic agent for example, in locally heated tissues contained within cargo elements 102a-102f and or vesicle 110. In one embodiment, efficient in vivo or in vitro release of entrapped agents at non-targeted and or targeted sites are triggered by light emitted by one or more Light Sources when the cargo elements 102a-102f, and or vesicle 110 contain a photoisomerisable species.

In an illustrative embodiment, in vivo and or in vitro release from one or more SBN element 100 of one or more entrapped liposomal and or non-liposomal-entrapped agents is optically triggered by photons emitted by one or more Light Sources. In one illustrative SBN embodiment, one or more Light Sources produce specific light wavelength emissions caused by their coming into contact with, for example, a specific disease at in vivo target site and causes diagnostic, therapeutic, and or prosthetic agents contained in a photosensitive SBN delivery system to be triggered and released from cargo elements 102a-102f and or vesicle 110, thereby forming a highly targeted drug delivery system. For example, in one embodiment, cargo elements 102a-102f and or vesicle 110 contain an amphipathic lipid, such as a phospholipid, having two chains derived from fatty acid that allow the lipid to pack into a bilayer structure. One or more photosensitizers may be incorporated into the entrapped materials' cavity and or membranes.

In one illustrative embodiment, a phospholipid (1,2-(4'-n-butylphenyl)azo-4"(-phenylbutyroyl))-glycero-3-phosphocholine ('Bis-Azo PC'), substituted with azobenzene moieties in both acyl chains that can be photoisomerised by a fast ARC nanolaser pulse. One or more other photoisomerisable species can be used in other embodiments. Agent release from cargo elements 102a-102f and or vesicle 110 occurs on the milliseconds timescale and photosensitised cargo elements 102a-102f and or vesicle 110 thereby serve as light sensitive cages to allow for the triggered release of agents from cage 106, cargo elements 102a-102f, and or vesicle 110. In one embodiment, cholesterol additives may be used. The addition of cholesterol may have a marked effect on kinetics of agent release and in some circumstances can result in substantial enhancement of light sensitivity in photosensitised cargo elements 102a-102f and or vesicle 110.

In another embodiment, both thermal and photosensitive activation systems are packaged and contained in the same SBN element 100.

In another embodiment, one or more Light Sources in one or more SBN element 100 operate in an intelligently staged sequence or orchestrated series of actions, which may be multiplexed by using one or more light and or thermal energy emitting sources and or done in parallel by using one or more light and or thermal energy emitting sources, such that various optical and or thermal energies from one or more Light Sources operate on one or more photosensitive and or thermal sensitive cage 106, cargo elements 102a-102f, and or vesicle 110 that contain one or more entrapped agents, resulting in a staged series of overall actions that follow an intelligently ordered sequence of events. For example, first a diagnostic agent from SBN element 100 is released by an optical and or thermal trigger and the agent's positive finding of a disease, like cancer or HIV then causes one or more therapeutic agents to be released from the same and or another SBN element 100 by one or more optical and or thermal triggers. Agent dosages are released in calculated amounts, and the dosages may be non-targeted and or targeted.

In further illustrative embodiments, free-floating cargo may be carried in cavity forming, non-permeable, cargo elements 102a-102f that contain a fluid or vapor, and/or be carried within a cavity forming, non-permeable vesicle 110 filled with a fluid or a vapor within cage 106, which free-floating cargo, for example, may be one or more molecular ensembles for enhanced medical imaging, or therapeutic agents.

In one illustrative embodiment, one or more cage 106, cargo elements 102a-102f, and, or vesicle 110 contain one or more treated manganese minerals, such as oxides, silicates, and carbonates in one SBN configuration for imaging enhancement.

In another embodiment, cage 106, and or cargo elements 102a-102f and or vesicle 110 contain one or more agents conjugated to one or more molecules, which so combined they can cross one or more cell membranes, including, for example, but not limited to, cargo elements conjugated to the peptide polyarginine. In another embodiment, cage 106 and or cargo elements 102a-102f and or vesicle 110 contain one or more conjugated diagnostic and or therapeutic agents to permeate one or more cellular membranes.

In another embodiment, cargo elements 102a-102f and or vesicle 110 are protected from the external environment, in vivo or in vitro, and cage 106 is stable with respect to dissociation and the caged cargo elements 102a-102f and or elements contained within vesicle 110, which may be toxic, are for example, but not limited to, radiodiagnostic agents and are sequestered from the surrounding environment.

In another illustrative embodiment, cage 106 and or cargo elements 102a-102f and or vesicle 110 contain one or more diagnostic agents like imaging contrast or radioactive agents to perform site designation, site specificity, and site retention for targeted in vivo delivery of therapeutics.

In another embodiment, cage 106, cargo elements 102a-102f, and or vesicle 110 contain one or more contrast agents for developmental imaging and diagnostic studies, which contrast agents are capable of crossing cellular membranes. Cage 106, cargo elements 102a-102f, and or vesicle 110 may contain, for example, one or more metal ions including, but not limited to, the gadolinium (III) chelate compounds of DTPA, DO3A, DOTA and other variations of these linear and macrocyclic ligands that act as contrast agents.

In another configuration, one or more cage 106, cargo elements 102a-102f, and or vesicle 110 contain one or more radiodiagnostic agents for nuclear medicine.

In another embodiment, one or more cage 106, cargo elements 102a-102f, and or vesicle 110 contain one or more therapeutic agents in addition to one or more imaging contrast and diagnostic agents. During some operations, cage 106, cargo elements 102a-102f may interact with, for example, an externally applied magnetic field, like NMR. However, since cage 106 is electrically neutral, only minimal (e.g., no) structural distortion of the clathrin cage 106 occurs in the presence of the magnetic field. Therefore, using cage 106 to capture cargo elements 102a-102f and or vesicle 110, which may be, for example, one or more NMR contrast agents, protects and extends the utility of cage 106 and cargo elements 102a-102f and or vesicle 110.

According to one SBN embodiment, one or more cage 106, cargo elements 102a-102f and or vesicle 110 contain an ion with one or more unpaired electrons. According to one in vivo application for enhanced medical imaging, one or more cage 106, cargo elements 102a-102f, and or vesicle 110, contain for example, but not limited to, one or more paramagnetic lanthanide or transition metal ion complexes that decrease the NMR relaxation times of nearby proton nuclei of H2O molecules, leading to brighter images and enhanced contrast between areas containing the contrast agent and the surrounding tissues.

Figure 5:
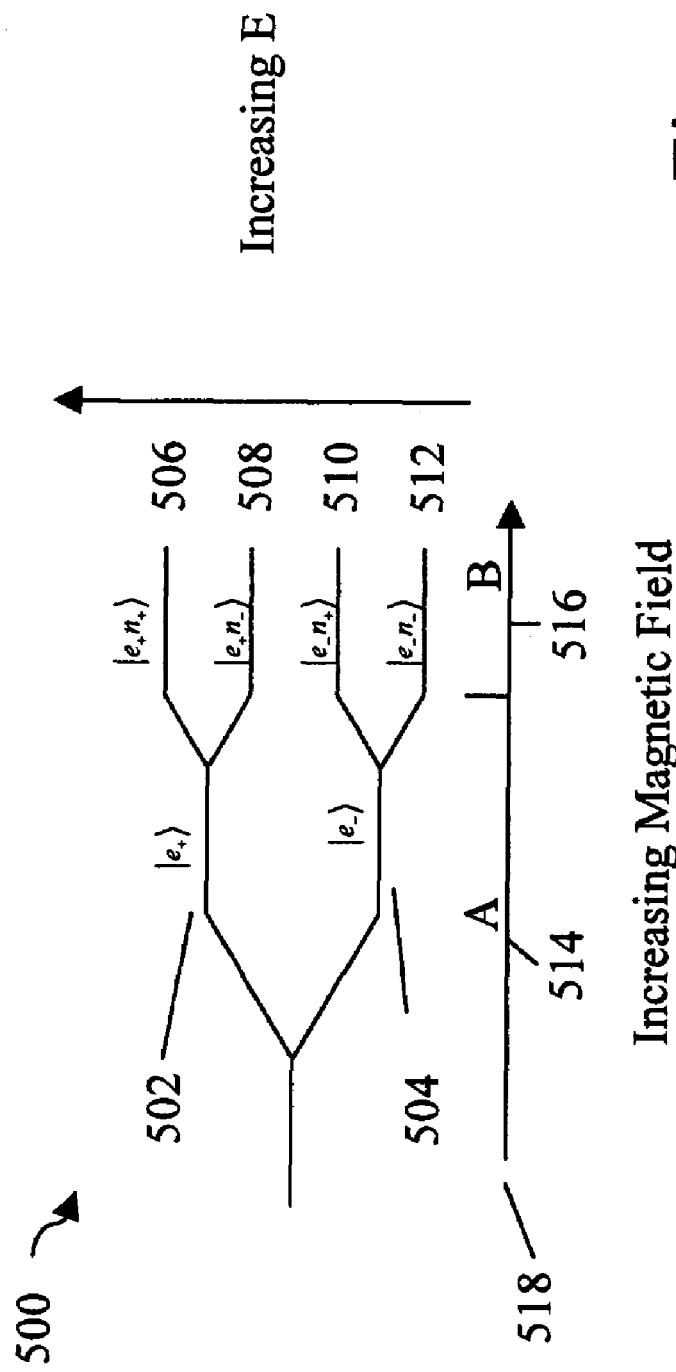
FIG. 5 is an exemplary energy level diagram 500 illustrating the energy levels associated with a hyperfine interaction between electron and nuclear spin in the presence of magnetic fields.

FIG. 5 is an exemplary energy level diagram 500 illustrating the energy levels associated with a hyperfine interaction between electron and nuclear spin in the presence of magnetic fields of the type used to do ESR spin label studies, which may be done in vivo and in vitro using the illustrative SBN element of FIG. 1 in one invention embodiment. The hyperfine interaction is a strictly quantum mechanical phenomenon. In an atom, the electron possesses an intrinsic quantum mechanical quantity known as spin. The nucleus of an atom also possesses spin. Intrinsic spin tends to generate a spin magnetic moment that is capable of interacting with other magnetic moments and fields. Generally, the spin magnetic moment of the nucleus does not interact with the spin magnetic moment of the electron. However, in the presence of a strong magnetic field, the spin magnetic moments of the electron and nucleus become coupled and interact.

In one illustrative embodiment, the electron is excited using pulses of electromagnetic radiation while maintaining its spin configuration. The source of the electromagnetic radiation may be, for example, an ordinary lamp, an LED, a time-varying magnetic field generator, a laser, or an electromagnetic field generator. A hyperfine interaction gives rise to electron nuclear double resonance (ENDOR) techniques. According to one illustrative embodiment of the invention, room temperature EPR and ENDOR techniques known in the art are used for performing in vivo spin probe studies.

Additionally, in other SBN embodiments, NMR are combined with other techniques, such as ENDOR, which combines the best aspects of ESR and NMR, to yield high sensitivity and nuclear selectivity, respectively, for in vivo and in vitro studies.

In one embodiment, one or more cage 106, cargo elements 102a-102f, and or vesicle 110 contain one or more metal ions including, but not limited to, gadolinium (III) chelate compounds of DTPA, DO3A, DOTA and other variations of these linear and macrocyclic ligands. Direct Gd3+-OH2 chemical bonds, which exchange rapidly with other bulk H2O molecules, produce the mechanism whereby unpaired 4f electrons on Gd3+ relax the proton nuclei of many nearby H2O molecules.

In one embodiment, one or more cage 106, cargo elements 102a-102f, and or vesicle 110 contain one or more of a wide range of lanthano-SBN labeled derivatives for custom-designed contrast agents. For example, it may be a water-soluble polyhydroxylated Gd3+-metallo-SBN, synthesized by a tetrabutylammonium hydroxide (TBA (OH)) phase transfer reaction.

In one embodiment, one or more element 100, cage 106, cargo elements 102a-102f, vesicle 110, receptors 104a-104f, adaptors 108a-108f, and or bonded elements utilize or exhibit quantum mechanical effects.

In another embodiment, one or more cage 106 and or cargo elements 102a-102f and or vesicle 110 contain one or more NMR/MRI contrast agents and during the same NMR/MRI operation, the same and or additional cages 106 and or cargo elements 102a-102f and or vesicle 110 may use quantum information processing techniques known in the art to modify, process, manipulate, encode and decode, input, output, transmit, communicate, store and read information using one or more modulated NMR/MRI signals or carrier signals.

In another illustrative SBN embodiment, targeted and or non-targeted in vivo and or in vitro delivery of cage element 106, and or cargo elements 102a-102f, and or vesicle 110 and or vesicle 110 cargo, and or bonded elements are internally and or externally monitored, directed, activated, deactivated and or regulated, locally and or at a remote distance by, for example, but not limited to, NMR, ESR, ultrasound, radio transmissions, and biochemical reactions.

In another embodiment, one or more cage 106 and or cargo elements 102a-102f and or vesicle 110 contain one or more diagnostic agents and during the same radiodiagnostic, EPR, or ESR, or ESEEM, or ENDOR or PET or SPECT or OCT operation, the same and or additional cages 106 and or cargo elements 102a-102f and or vesicle 110 use quantum information processing techniques known in the art to modify, process, manipulate, encode and decode, input, output, transmit, communicate, store and read information using one or more modulated EPR, ESR, ESEEM, ENDOR, PET, SPECT, or OCT signals, methodologies, or carrier signals.

In another illustrative embodiment, one or more SBN element 100 may perform guided and or targeted agent delivery, wherein one or more diagnostic, therapeutic, prosthetic, and or assay agents, but not limited to, and in any combination, are delivered to a target in vivo or in vitro using a variety of guiding and guidance techniques, including for example, optical, acoustic, electric, biological, chemical, and mechanical reactions and forces, but not limited to, and cage 106, cargo elements 102a-102f, and or vesicle 110 may be delivered singly and or in any combination to one or more targets.

In another embodiment, the SBN, cage 106 and or vesicle 110 and or cargo elements 102a-102f form a novel type of acoustically active Intelligent Bio-nanoparticle. Acoustic radiation forces and fragmentation techniques enable the invention to act as an acoustically active nanoparticle structure for use in vitro and in vivo, which, for example, may be used in precisely guided and targeted diagnostics and therapeutics. It is well known in the art that clinical ultrasound systems can generate pulses capable of fragmenting contrast agent microbubbles, and the general relationship between acoustic parameters and microbubble fragmentation has been documented in the prior art. Chomas et al. (2001) showed that the pressure threshold for fragmentation of a lipid-shelled microbubble increases with increasing bubble size, increases with increasing acoustic frequency, and decreases slightly with increasing pulse length.

Acoustically active liposomes (AALs) are available in the art in both micron and submicron size and can be filled with air or with low-solubility gases such as sulfur hexafluoride or perfluorocarbons, or can be liquid droplets that change phase at body temperature; their shells can be composed of lipids, albumin, or polymers. AALs in medicine can be used to guide and or deliver therapeutic and diagnostic agents. Ultrasound studies in the art have examined the effects of radiation force and fragmentation force on AALs and on ultrasound agents.

AAL systems in prior art are, however, unintelligent, and being dumb systems are incapable of doing anything more than very simple actions like rupturing and delivering cargo. The properties, capabilities and features of AALs suffer from limitations as found in other dumb delivery systems, like liposomes and whose limitations are discussed above. In marked contrast to prior art, in one embodiment, cage 106, and or vesicle 110, and or cargo elements 102a-102f comprise self-directed, smart, acoustically active structure(s) that may embody one or more of the above described invention's properties, features, and capabilities. In one embodiment, cage 106, vesicle 110, and or cargo elements 102a-102f are deliberately guided and precisely ruptured at one or more specific locales, in vitro or in vivo, via the use of acoustic techniques such as, for example, but not limited to, high frequency ultrasound techniques known in the art for head, body and organs, echo contrast microbubbles, ultrasound transducers implanted in transdermal patches, and or ultrasound transducer-tipped catheters that deliver one or more therapies and or perform imaging. Low, very low, and extremely low acoustic frequencies may also be used in other embodiments.

In another embodiment, inter-cranial ultrasound, including duplex ultrasound, is used to guide cage 106, cargo elements 102a-102f, and vesicle 110 to a specific site in the brain, and a fragmentation pulse is then applied that causes the rupture of the SBN carrier elements and the subsequent release of SBN-contained agents, which may be diagnostic, therapeutic, and or prosthetic agents. Ultrasound equipment available to clinicians combines both spectral Doppler analysis and real-time ultrasound imaging. This union is known as duplex ultrasound.

Further, the adult brain can today be examined with transcranial imaging (TCI) techniques to assess blood flow parameters within the Circle of Willis. This is of particular importance in evaluating stroke patients. In one illustrative embodiment, ultrasound techniques known in the art are used to guide cage 106, cargo elements 102a-102f, and vesicle 110 to a specific site in the brain, and a fragmentation pulse is then applied that causes the rupture of the SBN carrier elements and subsequent release of SBN-contained diagnostic agents and or therapeutic agents.

In one illustrative embodiment, ultrasound is used to guide cage 106, cargo elements 102a-102f, and vesicle 110 to a specific site in the body, and a fragmentation pulse is then applied that causes the rupture of the SBN carrier elements and subsequent release of SBN-contained blood clot-dissolving drugs; for example, tissue plasminogen activator (tPA), which is a thrombolytic agent. tPA is approved for use in certain patients having a heart attack or stroke. tPA can dissolve blood clots, which cause most heart attacks and strokes.

In one illustrative embodiment, ultrasound is used to guide cage 106, cargo elements 102a-102f, and vesicle 110 to a specific site in an in vivo fetus and a fragmentation pulse is then applied that causes the rupture of the SBN carrier elements and the subsequent release of SBN-contained agents to diagnose and or treat the fetus.

In another embodiment, particularly challenging hydrophobic drugs, for example, but not limited to, paclitaxel, are dissolved at high concentrations in a lipid-oil complex (e. g, 70 mg/ml, compared with 30 μg/ml in aqueous solutions and 1 mg/ml in lipid solutions) and are contained within cargo elements 102a-102f and or vesicle 110, with highly localized in vivo or in vitro drug delivery achieved via ultrasound radiation and or fragmentation forces. In another embodiment, an ultrasonic field causes diagnostic contrast agents contained within vesicle 110 and or cargo elements 102a-102f to localize along the wall of an arteriole. In another embodiment, models developed by Dayton, et al (1999) in the prior art are used to predict the displacement of the SBN produced by radiation forces acting on a contrast agent contained within vesicle 110 and or cargo elements 102-a-102f or by acting on vesicle 110 and or cargo elements 102-a-102f directly.

In another embodiment, resonant contrast nano-bubbles, for example, cage 106, vesicle 110 and or cargo elements 102a-102f are displaced on the order of millimeters during a 1-second ultrasound exposure at 3 MHz, thereby crossing a capillary, venule, or arteriole. In another embodiment, cage 106, vesicle 110, and or cargo elements 102a-102f are acoustically responsive, and their in vivo and in vitro movement in response to single radiation force pulses may be the same order as that of ultrasound contrast agents, approximately 1-2 nm per 200-kPa cycle at 2.5 MHz.

In one embodiment, ultrasound is used to precisely guide, and or deform, and or fragment the SBN, including cage. 106 and or vesicle 110 and or cargo elements 102a-102f in vivo or in vitro. In one embodiment, acoustic radiation-force parameters are used to variously deform the cage 106 and/or vesicle 110 and or cargo elements 102a-102F, which may also include other elements such as, for example, but not limited to, liposomes, and or other forms of nanodroplets. In another embodiment, fragmentation thresholds destroy the structural integrity of cage 106, vesicle 110, cargo elements 102a-102f, and or other contained elements, in vitro or in vivo for diagnostic and or therapeutic purposes.

In one embodiment, acoustic pulses are produced by an arbitrary waveform generator (like, for example, a Tektronix AWG 2021, Beaverton, OR), amplified approximately 55 dB with a radio frequency (RF) power amplifier (like, for example an ENI 3200LA, Electronic Navigation Industries, Rochester, N.Y.), and transmitted through a spherically focused ultrasound transducer (like, for example, a V305, Panametrics, Inc., Waltham, Mass.) with center frequency 2.25 MHz, -12 dB bandwidth 3 MHz, focal length 5.08 cm, and focal area ≈1 mm$^2$. Transmitted signals were calibrated using a needle hydrophone (like, for example a Specialty Engineering Associates PZT-0200, Soquel, Calif.) and a preamplifier (like, for example, a Specialty Engineering Associates' A17dB) linked to a digital oscilloscope.

In one illustrative embodiment, acoustic parameters for a radiation-force sequence acting upon SBN element 100, cage 106 and or vesicle 110 and or cargo elements 102a-102f consist of one pulse of 10 million cycles at a frequency of 3.0 MHz and a peak negative pressure of 50 kPa (ISPTA=46 mW/cm2). In another illustrative embodiment, fragmentation forces acting on cage 106, and or vesicle 110, and or cargo elements 102a-102f consist of a sequence of three pulses of 5 cycles each at 1.5 MHz and 2 MPa (MI=1.6), separated by 20 μs. A combined radiation force and fragmentation sequence may consist of one 10-million-cycle, 3.0-MHz, 50-kPa pulse (radiation force) followed by three 5-cycle, 1.5-MHz, 2-MPa pulses (fragmentation).

In one illustrative embodiment, one or more SBN element 100, cage 106 and or vesicle 110 and or cargo elements 102a-102f are placed in a static chamber that is mounted in a 500-ml optically and acoustically transparent polycarbonate tank with a spherically focused 2.25 MHz transducer mounted in one wall of the tank such that its focus falls at the center of the plastic cell plate holding cage 106 and or vesicle 110 and or cargo elements 102a-102f in the static chamber. The distance between the two unbreakable plastic cover slips (e.g., like those available from Structure Probe, Inc./SPI Supplies, West Chester, Pa.) holding the SBN specimens is approximately 1.5 mm. [Cling film, dialysis membrane, Parafilm, as well as SPI plastic cover slips are all equally acceptable as acoustically transparent windows for ultrasound, whereas glass cover slips of 'soft' surfaces (in which active bubbles may embed themselves) are not. SPI plastic cover slips are also nearly optically transparent. A 1-cm thick block of acoustically absorbent rubber (like, for example, an Aptflex F28, Precision Acoustics Ltd., Dorchester, UK) is placed in the tank behind the chamber, in the rear of the box, in order to minimize multiple reflections. The tank is filled with saline solution in order to provide acoustic coupling for the transducer.

In another illustrative in vivo or in vitro embodiment, one or more Light Sources in one or more SBN element 100 are used for a system that is a sensitive, benchtop flow analyzer, capable of performing hundreds of bioassays simultaneously. In one embodiment, one or more SBN element 100 does angiography. In another illustrative embodiment, one or more SBN element 100 are part of a Micro-Electro-Mechanical-System (MEMS) based sensor for detecting toxic, chemical, nuclear and or biological materials.

In another illustrative embodiment, the increasing interest in the targeting of foreign moieties at sites in the body where their activity is required is addressed by the invention.

In one illustrative embodiment, the invention is an improvement over in vivo nanoparticles because it enables targeted agent delivery systems that retain their structural integrity and may also loiter for a calculated period of time at the targeted area of concern after delivery of agent payload.

In one illustrative embodiment, the cargo elements 102a-102f and or vesicle 110 contain one or more cargo molecules arranged in specific patterns within clathrin cage 106. The pattern of cargo element 102a-102f attachment precisely mirrors or mimics a spatial or physical pattern a target cell in a human or animal body expects to see and will recognize, and clathrin cage 106 and its molecular cargo elements 102a-102f are accepted by the target cell, which can be a cancer cell or HIV infected cell, for example.

In one illustrative embodiment, the invention is an improvement over other in vivo biodegradable polymer nanospheres, liposomes, lipids, caspid agent delivery systems, as well as endohedral Fullerenes and other nanoparticles in prior art because, a) the invention enables the use of one or more targeting moieties and the use of one or more types of cargo, and or b) perform on the fly smart target prioritization for a single cargo type or for multiple cargo types, which orchestrated actions may be enabled by using natural control laws that govern biological elements, and or by using behaviors as defined by graphs and or an algebra, for example, a Lie algebra.

In one illustrative embodiment, one or more cage 106, receptors 104a-104f, adaptors 108a-108f, cargo elements 102a-102f, and or vesicle 110 follow a sequence of events that comprise a logically orchestrated set of agent targeting conditions, such as, "if this, then do that", and so forth, and which logical operations may utilize algebras, such as Lie and Clifford algebras and or biological control laws. In one embodiment, the invention is an improvement over other in vivo nanoparticles in the art, because it enables the ability to intelligently monitor, control, react, and further adjust cellular processes by interactively administering one or more types of agent payloads depending on dynamically changing intercellular and intra-cellular conditions. One consequence may be maximizing agent efficacy and patient safety.

In one illustrative embodiment, the invention enables smart targeted agent delivery systems, in vivo and or in vitro, that engage in an iterative, interactive, and dynamic dialog with one or more targets, that follow a sequence of actions governed by biological control laws, and or by using behaviors as defined by graphs and or an algebra, for example, a Lie algebra. In one illustrative example, cage 106 and or cargo elements 102a-102f, and or vesicle 110 and or element 100 follow an algorithm expressed by the invention, such as:

1) One or more SBN element 100 docks at one or more cell receptors on one or more cell membranes,
2) Docked element 100 releases its agent cargo that enters one or more target cells,
3) The docked element 100 waits for a time certain period,
4) The targeted cell produces one or more reactions, for example, manufactures and secretes an agent in response to the agent cargo delivery,
5) The docked element 100 analyze the new cell behavior and or its secretions,
6) The docked element 100 undergoes a conformational change in response to the cell's cargo-altered behavior,
7) The docked element 100 releases another round of one or more agents that are taken up by the targeted cell, and,
8) The foregoing process is repeated.

In one illustrative embodiment, the invention is an improvement over other in vivo nanoparticles in the art because, in one aspect, the invention uses molecular-imprint technology, wherein biodegradable films are used as a pliable template for biological elements, which elements are pressed into a film and then removed, leaving a physical mold of the biological element's shape. The film is hardened and then used to detect that particular biological element, like a receptor, protein, or cell, since its complex shape will bind only to that particular biological element. In one embodiment, this process provides for biodegradable polymeric nanocapsules with molecular-level features that provide lock and key biological element templates that may be used for site specific in vivo targeting and or enhancing agent/target receptor specificity.

It is important that agents, like drugs, particularly those having undesirable side effects, are delivered to the site where they are supposed to act. Many molecular species require that they be delivered in a site specific manner, often to particular cells, for example, polynucleotides (anti-sense or ribozymes), metabolic co-factors or imaging agents. One such system has been described by Wu et al., J. Biol. Chem., 263, 14621-14624 and WO-A-9206180, in which a nucleic acid useful for gene therapy is complexed with polylysine linked to galactose which is recognized by the asialoglycoprotein receptors on the surface of cells to be targeted. However, there are many occasions, such as in the delivery of a cytotoxic drug, when it would not be satisfactory to use a delivery system in which the targeting and or masking moiety and or vector to be delivered is so exposed. This need is addressed by various delivery system embodiments of the invention that possess the flexibility to target a wide range of biologically active foreign moieties.

According to one embodiment, the protein amino acid sequence of cage 106, and or cargo elements 102a-102f and or vesicle 110 are modified to provide a site suitable for attachment thereto of an in vivo or in vitro targeting and or masking moiety. In one illustrative SBN embodiment, one or more target-specific ligands and or targeting moieties are attached to cage 106, cargo elements 102a-102f, and or vesicle 110 via one or more short molecular tethers and/or one or more ligands are attached directly to cage 106, cargo elements 102a-102f, and or vesicle 110. Target-specific ligand binding and any subsequent changes within or to cage 106 and/or cargo elements 102a-102f, and/or vesicle 110 may be a result of either covalent or non-covalent interactions—the latter type including ionic interactions, hydrophobic interactions, or hydrogen bonds—depending on the application, system design, receptor design, cargo type and or the interaction/application environment.

In another illustrative SBN embodiment, reactions and forces arise from one or more ligands and or targeting moieties binding to targets, including covalent and non-covalent interactions, which ligands are tethered or attached to cage 106, cargo elements 102a-102f, and or vesicle 110. Ligand binding to one or more specific targets may produce one or more conformational changes sufficient to deform and or rupture one or more cage 106, and or cavity forming vesicle 110 and/or cavity forming cargo elements 102a-102f in whole or in part, thereby causing one or more agents or cargo elements to be released from cage 106, and or cargo elements 102a-102f and/or vesicle 110. Such deformations may also cause one or more ARC nanolasers to emit coherent laser light.

The targeting moieties can be selected by one of ordinary skill in the art keeping in mind the specific cell surface to be targeted. For example, if one wishes to target the asialoglycoprotein receptor on the hepatocytes in the liver, an appropriate targeting moiety would be clustered trigalactosamine. Once a specific targeting moiety has been selected for a particular cell to target, the different targeting moieties can be attached either by covalent linkage directly onto the surface of cage 106, and or cargo elements 102a-102f and or vesicle 110, or by indirect linkage via, for example, a biotin-avidin bridge. In another embodiment, depolymerization (e.g., by cytosolic Hsc 70) of the clathrin and or coatamer coated vesicle exposes one or more transmembrane proteins (V-SNARE) that direct cargo elements 102a-102f and or vesicle 110 to its destination by binding to a specific T-SNARE protein on the target organelle. The fusion protein SNAP25 causes the cargo elements 102a-102f and or vesicle 110 to fuse with the target membrane In one embodiment, avidin is attached covalently to the surface of cage 106, and or cargo elements 102a-102f and or vesicle 110 and a biotinylated ligand attaches non-covalently to the avidin. In another embodiment, biotin is covalently attached to the surface of cage 106, and or cargo elements 102a-102f and or vesicle 110, and then avidin is used as a bridge between the biotinylated polymer and the biotinylated ligand. Targeting agents may also include one or more biocompounds, or portions thereof, that interact specifically with individual cells, small groups of cells, or large categories of cells. Examples of useful targeting agents include, but are not limited to, low-density lipoproteins (LDS's), transferrin, asiaglycoproteins, gp120 envelope protein of the human immunodeficiency virus (HIV), and diptheria toxin, antibodies, and carbohydrates. A variety of agents that direct compositions to particular cells are known in the prior art (see, for example, Cotten et al., Methods Enzym, 1993, 217, 618).

In one embodiment, one or more masking moieties are attached to the surface of cage 106, and or cargo elements 102a-102f and or vesicle 110. These masking moieties prevent the recognition by a specific cell surface and instead allows for intravenous administration applications. For example, the surface masking characteristics may be provided by poly(ethylene glycol) (PEG) by using various PEG-PLA and PLGA mixture.

In one embodiment, the invention includes one or more element 100, cage 106, and or cargo elements 102a-102f, and or vesicle 110 having one or more suitable sites for subsequent attachment of a targeting and or masking moiety and or vector, and one or more element 100, cage 106, and or cargo elements 102a-102f and or vesicle 110 having one or more surfaces and or protein coats to which one or more targeting and or masking moieties and or vectors have already been attached.

In another illustrative SBN embodiment, one or more classical structural activity relationships (SARs) based drug discovery approaches are combined with one or more other techniques to form a specific case of targeted drug delivery, for example, but not limited to, one or more structural metabolism relationships (SMRs) that in combination with SARs are sometimes termed as retrometabolic drug design approaches. These active drugs are designed to undergo singular metabolic deactivation after they achieve their therapeutic roles, and may produce specific action at the site of application without affecting the rest of the body.

In another illustrative embodiment, cage 106 and or cargo elements 102a-102f and or vesicle 110 contain one or more agent functionalities that produce targeting by changing molecular properties of an overall target molecule, as a result of enzymatic conversion, but also, for example, may involve one or more pharmacophores. These elements, sometimes referred to as the targetor (Tor) moiety, are converted by site-specific enzymes to active functions. In addition to the Tor moiety, one or more other functions may be introduced into SBN elements for in vivo use, which can be named as "protector functions" that serve as lipophilicity modifiers or protectors of certain functional groups in therapeutic agent molecules.

The form in which the foreign moiety and or vector or cargo is held within cage 106 and or cargo carrying elements 102a-102f and or vesicle 110 will depend on the release properties required. For release at the targeted site, it will be important to ensure that the right conditions prevail, for example, to permit cell localization and internalization via receptor mediated endocytosis.

In another illustrative embodiment, one or more drug, agent, and or element targeting delivery systems and methods are used, for example, but not limited to, and in any combination in whole or in part: surfactants (surface-active substances) and or cosurfactants; enzymatic physical-chemical-based targeting; site-specific enzyme-activated targeting; vectors, such as ligand-based, non-viral-based, and Protein/DNA polyplex vector targeting; receptor-based chemical targeting; organic and or inorganic synthetic elements; transmembrane proteins (V-SNARE); peptides, including peptides that cross cell membranes and home specifically to certain diseases; nanostructured dendrimers and hyperbranched polymers; molecular Trojan horses; adenovirus, herpes simplex virus, adeno-associated virus or other virus vectors for targeted delivery that do not cause toxicity; antibodies, including monoclonal antibodies; nanoparticles, including polymer nanoparticles like polymer, polybutylcyanoacrylate, and ethyl alcohol nanoparticles; immunotoxins; hormonal therapy; tissue-specific gene expression; gene therapy; pegylated immunoliposomes; anti-sense therapy; biological elements and or agents, including biological elements and agents conjugated with other agents, such as transferrin, but not limited to such; chemical elements and agents; devices, systems, and or mechanisms; liposomes, including liposomes conjugated with transferrin, but not limited to such; conformationally-constrained peptide drugs targeted at the blood-brain barrier; endogenous blood brain barrier and or blood tumor capillary transporters; inhibiting and or modulating blood brain barrier active efflux transporters; air and or other gas bubbles; blood brain barrier breaking and or disrupting elements and agents; blood brain barrier tight junction separating and or endocytoses elements and agents; vector-mediated delivery of opioid peptides to the brain; and or brain drug delivery of peptides and protein drugs via vector-mediated transport at the blood brain barrier.

The invention, in one embodiment, the invention is used as new model to study, research and develop new, improved, and more accurate CNS models; new psychotropic drugs with minimal side effects; new psychiatric therapies; new prosthetics; and new, highly efficacious targeted psychotropic drug delivery systems. For example, some psychotropic drugs disrupt the clathrin endocytosis process, like the drug chlorpromazine (thorazine) that inhibits clathrin-dependent endocytosis. Chlorpromazine is a cationic amphiphilic drug, which prevents the recycling of clathrin and thus prevents endocytosis by clathrin-dependent mechanisms. Chlorpromazine, induces a redistribution of a clathrin-coated pit component, AP-2, to endosomes. Some studies show that chlorpromazine reduce transferrin, but not cytokine interleukin 2 (IL2) internalization. Thus, unexpectedly, this cytokine and its receptors can still be rapidly endocytosed in the absence of functional clathrin-coated structures. A new model for receptor-mediated endocytosis is therefore needed, and which requirement is fulfilled in one illustrative SBN embodiment that accounts for such results as well as published data on other receptors, especially when psychotropic drugs are involved.

In another illustrative SBN embodiment, cage 106, and or cargo elements 102a-102f, and or vesicle 110, and or their bonded elements cross the blood brain barrier for targeted delivery of agents and elements, including, but not limited to, small and or large molecules, non-lipid-soluble micromolecules, macromolecules, Light Sources, hydrophilic and or hydrophobic agents, such as therapeutic, diagnostic, and prosthetic agents, and other structured cargo to specific cells and areas within the brain, and such agents and cargo may contain one or more sensor agents, assay agents, diagnostic agents, prosthetic agents, and also may contain therapeutic agents like central nervous system drugs, antibiotics, and antineoplastic agents, but are not limited to such.

In another illustrative SBN embodiment, cage 106, and or cargo elements 102a-102f, and or vesicle 110, and or their bonded elements cross various in vivo biological barriers, such as the transmucosal passage, and also the blood-brain barrier (BBB) and the blood-cerebrospinal fluid (CSF) barrier for targeted in vivo delivery of agents and elements without requiring modification of the agents and elements.

In another illustrative SBN embodiment, cage 106, and or cargo elements 102a-102f, and or vesicle 110, and or their bonded elements are coated with one or more surfactants and or cosurfactants, including, but not limited to, polysorbate 20, 40, 60 and 80, and or with one or more other materials and substances to cross various biological barriers, such as the transmucosal passage, and also to overcome the blood-brain barrier (BBB), the transmucosal passage, and the blood-cerebrospinal fluid barrier (CSG) for targeted delivery of agents and elements nanoparticles.

In another illustrative SBN embodiment, cage 106, and or cargo elements 102*a*-102*f*, and or vesicle 110, and or their bonded elements cross the blood brain barrier without requiring the opening of the blood brain barrier.

Therapeutic efficacy in vivo, particularly with regard to the central nervous system (CNS), frequently is diminished or prevented by the inability of a therapeutic agent to reach and maintain active concentrations in the brain for an appropriate length of time. Frequently, the molecule is too large or has polar functional groups, so that its access to the brain target organ is limited by the blood-brain barrier (BBB). The BBB is a system of layers of cells at the cerebral capillary endothelium, the choroid plexus epithelium, and the arachnoid membranes that are connected by tight junctions (zonulae occludens), and that together separate the brain and cerebrospinal fluid (CSF) from blood The past few decades have witnessed a burgeoning interest in delivering blood-borne, non-lipid-soluble micromolecules and macromolecules (e.g., peptides, proteins) and chemotherapeutic substances into the brain to combat infections, tumors, enzyme and neurotransmitter deficiencies, toxins, and the like associated with disease or dysfunction of the central nervous system (CNS). Coupled to this interest are the CNS entry of psychotherapeutic drugs and the overwhelming health and socioeconomic consequences of drug abuse and addiction, which are addressed in one CNS embodiment of the invention, as are the issues of weight gain and diabetes associated with CNS medications in another CNS embodiment.

Scientific investigations have focused on the fluid-brain barriers, cells that inhibit the ready passage of non-lipid-soluble molecules, especially large molecules, between the environment external to the CNS (i.e., air, blood) and the CNS milieu. These fluid-brain barriers include (1) the blood-brain barrier (BBB) associated with capillary, venule, and arteriole nonfenestrated endothelia of cerebral blood vessels; (2) the bloodcerebrospinal fluid (CSF) barrier associated with epithelia of the choroid plexus and other circumventricular organs (e.g., median eminence, area postrema); (3) the nose-brain barrier associated with epithelia of the nasal mucosa; and (4) the arachnoid mater-CSF barrier. Each of the barriers are believed to be attributed to circumferential belts of intercellular tight junctional complexes that preclude the extracellular movement of non-lipid-soluble micromolecules and macromolecules bidirectionally between the external environment and the CNS.

Despite reports advocating experimental manipulation to open the fluid-brain barriers transiently, most notably the BBB, these barriers under normal conditions are not absolute. Each is circumvented in a noninvasive fashion by large-molecular-weight endogenous and exogenous proteins moving within patent extracellular routes and/or traversing intracellular pathways related to adsorptive and receptor-mediated endocytic processes. For example, in one embodiment, cage 106, and or cargo elements 102*a*-102*f* and vesicle 110 deliver small and large molecules, non-lipid-soluble micromolecules, macromolecules, Light Sources, and other structured cargo from the periphery and are capable of circumventing the fluid-brain barriers by intracellular routes related to three separate and distinct endocytic processes. The three endocytic processes from the least to the most specific are fluid- or bulk-phase endocytosis, adsorptive endocytosis, and receptor-mediated endocytosis.

In one embodiment, chimeric peptides are used to enhance cage 106, cargo elements 102*a*-102*f* and vesicle 110 for delivery of small or large molecule cargo elements through the blood-brain barrier chimeric peptides formed by linkage of a vasoactive intestinal peptide (VIP) analogue, which has been monobiotinylated, to a drug transport vector. One SBN embodiment is for the purpose of achieving a central nervous system pharmacologic effect. For example, successful targeted drug delivery across the blood-brain barrier to the brain via the transferrin receptor-mediated endocytosis pathway is described in the art (Qian, et al 2002), and the technique is used in one SBN embodiment. The brain capillary endothelium, which makes up the (BBB) in vivo, expresses high concentrations of transferrin receptor, and studies in the art have shown that an antitransferrin receptor monoclonal antibody may function as a BBB drug transport vector for targeted delivery. In one embodiment, a chimeric peptide is formed by linkage of a potent vasoactive intestinal peptide (VIP) analogue, which has been monobiotinylated, to a drug transport vector. The vector consists of a covalent conjugate of avidin and the OX26 monoclonal antibody to the transferrin receptor. Owing to the high concentration of transferrin receptors on brain capillary endothelia, OX26 targets brain and undergoes receptor-mediated transcytosis through the blood-brain barrier. In one study in the art (Bickel et al 1993), pharmacologic effects in vivo in the brain by vector-mediated peptide drug delivery resulted in an in vivo central nervous system pharmacologic effect: a 65% increase in cerebral blood flow. Biotinylated VIP analogue without the brain transport vector was ineffective.

In another embodiment, zonula occludens toxin and its eukaryotic analogue, zonulin, (zot) are protein ligands attached to cage 106 and or cargo elements 102*a*-102*f* and or vesicle 110. Zonulin, the natural ligand of the Zot target receptor, interacts with these receptors at the blood brain barrier, unlocking the tight junctions (TJ) in the brain that regulate the blood-brain barrier at that receptor. TJ-unlocking allows passage of cage 106 and cargo elements 102*a*-102*f* and or vesicle 110 through the BBB, and thereby enables delivery of small and large molecules, non-lipid-soluble micromolecules, macromolecules, Light Sources, and other structured cargo elements to the brain.

Extracellular pathways circumventing the fluid-brain barriers in humans are comparable in the CNS of rodents and a subhuman primate. The most highly documented extracellular route is through the circumventricular organs (e.g., median eminence, organum vasculosum of the lamina terminalis, subfomical organ, and area postrema), all of which contain fenestrated capillaries and, therefore, lie outside the BBB. In one embodiment, blood-borne macromolecules, specifically fluid-phase molecules released by an SBN, escaping fenestrated vessels supplying the circumventricular organs move extracellularly into adjacent brain areas located behind the BBB.

The potential intracellular and extracellular pathways that blood-borne substances carried within cage 106 and or cargo elements 102*a*-102*f* and or vesicle 110 may follow in various embodiments for circumventing the fluid-brain barriers and entry to the CNS are therefore numerous and various embodiments are used as appropriate.

In one illustrative SBN embodiment, cage 106, and or cargo elements 102*a*-102*f*, and or vesicle 110, and or their bonded elements contain one or more small and large molecules that cross the blood brain barrier by using acoustically active SBN element 100 and intracranial ultrasound for targeted delivery of diagnostic and or therapeutic agents to specific cells and areas within the brain.

In one illustrative SBN embodiment, cage 106, and or cargo elements 102a-102f, and or vesicle 110, and or their bonded elements contain one or more small and or large molecules that cross the blood brain barrier for targeted delivery of diagnostic and or therapeutic agents to specific cells and areas within the brain, like, for example, contrast agents, central nervous system drugs, antibiotics, and antineoplastic agents, which may be used for treating, but not limited to, Parkinson's, Multiple Sclerosis, brain tumors, meningitis, Alzheimer's disease, HIV infection, memory, stroke, and other disorders, diseases, and insults to the brain. In another illustrative SBN embodiment, cage 106, and or cargo elements 102a-102f, and or vesicle 110, and or their bonded elements, contain one or more psychotropic agents and or therapies for studying, alleviating, preventing, curing, and or controlling mental health, including, but not limited to, stress, anxiety, depression, mania, bipolar disorder, attention deficit (hyperactivity) disorder, panic attacks, phobias, addictions, anger, rage, suicidal thoughts and tendencies, post traumatic stress disorder, psychoses, mental retardation, autism, schizophrenia, and or neuroses, and or enhancing memory, cognition, cognitive functioning, and or the effects of cognitive therapy.

According to another feature, cage 106, and or cargo elements 102a-102f, and or vesicle 110, and or their bonded elements are encapsulated in, and or utilize, in whole or in part one or more molecular-imprinting technology methods, wherein biodegradable films, for example, but not limited to, polymer films, are used as a pliable template for biological elements. Biological elements are pressed in vitro into a pliable film and then removed, leaving a physical mold of the biological element's shape. The film may then be hardened and cast into a nanocapsule. In one embodiment, this invention process provides for imprinted biodegradable capsule production with target or site-specific feature sizes at the molecular level. In another embodiment. Other embodiments utilize imprinted membranes and thin films that also function as an artificial cell wall or barrier for the selective transport of targeted drugs, peptides and biologically important molecules.

In another illustrative embodiment, cage 106 and or cavity-forming cargo elements 102a-102f and/or cavity-forming vesicle 110 have one or more compartments that in whole or in part are separated by one or more barriers, for example, but not limited to, one or more phospholipid membrane barriers and or one or more barriers comprised of molecular-imprinted films. The barriers may exhibit structural transitions due to internal or external stimuli. In one embodiment, agents or cargo entrapped within cage 106 and or 102a-102f, and or vesicle 110 remain sequestered within their respective compartments until a change in barrier permeability state is triggered by contact, for example, by a ligand, with one or more specific targets or sites. The subsequent biochemical and or biological reactions cause the barriers to alter states into an opened state and release entrapped cargo and agents from cage 106 and or 102a-102f, and or vesicle 110. In one example embodiment, binary mixtures of therapeutic and or diagnostic agents are mixed together as needed to dynamically and more efficaciously deal with a disease, such as a cancer or HIV.

The emergence of molecular imprinting has its original source in the area of immunology and goes back more than fifty years. A wide variety of print molecules have been used in various imprinting protocols known in the art. Compounds such as drugs, amino acids, carbohydrates, proteins, nucleotide bases, hormones, pesticides and co-enzymes have been successfully used in prior art for the preparation of selective recognition matrices. Of all the imprinting strategies known in the art, it has become evident that the use of non-covalent interactions between the print molecule and the functional monomers is the more versatile. The apparent weakness of these interaction types, when considered individually, may be overcome by allowing a multitude of interaction points simultaneously. Together with the fast association and dissociation kinetics of these bond types, so that in a short time many possible combinations can be checked before the correct partners associate, this protocol has proven advantageous. Furthermore, the use of non-covalent interactions in the imprinting step closely resembles the recognition pattern observed in nature.

Molecularly imprinted polymers have been used in several configurations known in the art. By far the most used technique involves the preparation of bulk polymer monoliths, which after fragmentation and particle sieving (giving particles of usually about 25 µm) are used in several applications known in the art. For chromatographic applications other configurations have been developed in the art. Thus, polymers have been prepared in situ in chromatography columns, and in capillary electrophoresis systems. Since the flow properties in chromatography are dependent on particle size and shape, attempts have also been made in the art to acquire molecularly imprinted polymer particles homogeneous in dimensions and morphology. This has been accomplished in the known art by following two different routes: (1) grafting/coating of the imprinted polymer on pre-formed particles, such as silica or poly-(trimethylolpropane trimethacrylate) particles: (2) Preparation of beads through suspension, emulsion or dispersion polymerisation. In this manner, spherical molecularly imprinted polymer particles with narrow size distribution can be obtained, providing good flow performances in chromatography. For analytical or sensor-device applications, thin layers or polymer membranes have been developed in the art. In this case, the polymer is either directly cast as a thin layer on a surface or chip, or alternatively, molecularly imprinted polymer particles are glued together using a particle binding agent obtaining, e.g. coated glass plates similar to those used in thin layer chromatography, The obvious advantages with the direct approaches are that particle sizing is unnecessary and that the sites left in the polymer are undamaged from any fragmentation or sieving process. Example SBN molecular imprint embodiments in the art include, but are not limited to:

Fragmented polymer monoliths

Composite polymer beads

Polymer beads from suspension, emulsion or dispersion polymerisation

In-situ polymerisation

Polymer particles bound in thin layers

Polymer membranes

Surface-imprinted polymer phases

A further technique known in the art, which may be denoted surface imprinting, involves the following steps: The print molecule, usually a large one, is first allowed to form adducts with functional monomers in solution and the formed complexes are subsequently allowed to bind to an activated surface such as silica wafers or glass surfaces. Thus, with this technique, a designed imprinted, or imaged, surface is obtained. This approach should potentially be valuable for creating specific cell binding surfaces. When preparing molecularly imprinted polymer monoliths against large imprint species, there is a risk of permanent entrapment of the template in the polymer after polymerisation. When using thin polymeric layers or imprinted surfaces this drawback may be overcome.

In one embodiment, imprinted nanocapsules using techniques known in the art and also as discussed above, contain cage 106, and or cargo elements 102a-102f, and or vesicle 110, and or their bonded elements, and or non-SBN elements and constitute a smart nanocapsule with manifold, multi-tiered capabilities for in vivo administration and targeted delivery. The imprinted nanocapsule is delivered in vivo to detect and target a particular in vitro imprinted biological element, which may be, but is not limited to, a particular type of receptor, protein, or cell, since its complex imprint shape on the nanocapsule will only bind in vivo to that particular biological element target. The molecular-level imprint process thereby provides for a smart targeting SBN element 100 using biodegradable nanocapsules for in vivo agent delivery. In addition, vectors and targeting moieties, and blood brain barrier, transmucosal, and CSF barrier breaching elements, and other elements and substances may also be attached to the surface of the molecular imprint nanocapsule or otherwise be conjugated to it.

In another illustrative embodiment, cage 106, and or cargo elements 102a-102f, and or vesicle 110, and or their bonded elements may be used in conjunction with molecularly imprinted polymers known in the art as recognition elements in biosensor-like devices, as one of the most appealing applications developed in the area of molecular imprinting is the use of molecularly imprinted polymers as recognition elements in biosensor-like devices. Normally, a sensing element, such as an enzyme, antibody or receptor, is immobilized at the interface between the sensor and the analyte sample. A selective chemical signal, resulting from the binding process of the analyte to the recognition element is subsequently transduced into an electrical signal, amplified and converted to a "manageable" format. Characteristic of these devices is the close proximity between the sensing part and the transducing element. Substituting natural sensing elements with molecularly imprinted polymers has a number of potential advantages similar to those found with the aforementioned antibody substitutes. Thus, such sensor SBN embodiments are far more stable and may also perform in harsh environments, and in cases where no biological recognizing element is found, they may be the only alternative. Further, a close intermarriage between sensing and transducing function may be used in one SBN embodiment. Given the advantages of molecularly imprinted polymers over their natural counterparts, imprinted polymer SBN embodiments may be highly resistant sensing element alternatives.

In another illustrative embodiment, cage 106, and or cargo elements 102a-102f, and or vesicle 110, and or their bonded elements are encapsulated in whole or in part in one or more biodegradable controlled-release polymers, which polymers may also be conjugated with other elements and agents. The polymer capsule, and or cage 106, and or cargo elements 102a-102f, and or vesicle 110, and or their bonded elements may also be coated with one or more surfactants and or cosurfactants and or with other materials and substances. One or more targeting and or masking moieties and or other targeting vectors may also be attached on the polymer surface, and or on cage 106, and or cargo elements 102a-102f, and or vesicle 110, and or their bonded elements.

In one embodiment, cage 106, and or cargo elements 102a-102f, and or vesicle 110, and or their bonded elements are put into one or more biodegradable controlled-release polymeric capsules, and these SBN elements transform "dumb" polymeric delivery capsules into smart systems.

In the instance of polymeric nanocapsules, which may be molecular imprinted or not, illustrative controlled-release polymeric nanocapsule embodiments of the invention may include one or more of the following delivery systems, but are not limited to, and in any combination:

1. Diffusion-controlled systems, which can be subdivided into two categories: monolithic devices and membrane-controlled devices. In a monolithic device, the therapeutic agent is dispersed in a polymer matrix, and its release is controlled by diffusion from the matrix into the surrounding environment. In a membrane-controlled device, the therapeutic agent is contained in a core surrounded by a thin polymer membrane and is released to the surrounding environment by diffusion through the rate-limiting membrane.

2. Water penetration-controlled delivery devices, whereby rate control is achieved by the penetration of water into the device. In one type, the driving force is provided by osmosis. In this device, an osmotic agent is contained within a rigid housing and is separated from the therapeutic agent by a movable partition. One wall of the rigid housing is a semipermeable membrane and, when the device is placed in an aqueous environment, water is osmotically driven across this semipermeable membrane. The resultant increase in volume within the osmotic compartment exerts pressure on the movable partition, which then forces the therapeutic agent out of the device through the delivery orifice. In another type of water penetration device, the driving force is provided swelling. In swelling-controlled delivery systems, the agent is dispersed in a hydrophilic polymer that is glassy in the dehydrated state but which swells when placed in an aqueous environment.

3. Chemically controlled systems, whereby drug release from bioerodible polymers can occur by any one of the three basic mechanisms. In mechanism A, the active agent is covalently attached to the backbone of a biodegradable polymer and is released as its attachment to the polymer backbone cleaves by hydrolysis of bond A. because it is not desirable to release the drug with polymer fragments still attached for toxicological reasons, the reactivity of bond A should be significantly higher than the reactivity of bond B. In mechanism B, the active agent is contained within a core and is surrounded by a bioerodible rate-controlling membrane. Release of the active agent is controlled by its diffusion across the membrane. In mechanism C, the active agent is dispersed in a bioerodible polymer, and its release is controlled by diffusion, by a combination of diffusion and erosion, or in rare instances by pure erosion.

4. Drug covalently attached to polymer backbone systems, which delivery systems can be further subdivided into soluble systems and insoluble systems. Insoluble systems are used as a subcutaneous or intramuscular implant for the controlled release of the chemically tethered therapeutic agent. Soluble systems are used in targeting applications.

5. Drug release determined predominantly by erosion systems, whereby certain polymers can undergo a hydrolysis reaction at decreasing rates from the surface of a device inward, and under special circumstances the reaction can be largely confined to the outer layers of a solid device. Two such polymers are poly (ortho esters) and polyanhydrides, because the rates of hydrolysis of these polymers can be varied within very wide limits, considerable control over the rate of drug release can be achieved.

6. Poly (ortho esters) systems, which are highly hydrophobic polymers that contain acid-sensitive linkages in the polymer backbone.

7. Polyanhydrides materials as bioerodible matrices for the controlled release of therapeutic agents. Aliphatic polyanhydrides hydrolyze very rapidly while aromatic polyanhydrides hydrolyze very slowly, and excellent control over the hydrolysis rate can be achieved by using copolymers of aliphatic and aromatic polyanhydrides. In this way, erosion rates over many days have been demonstrated, and erosions rates measured in years have been projected.

8. In one illustrative embodiment, SBN element 100, bonded elements, and or Light Sources may be harmlessly dissolved, passed, and or excreted from the body.

The invention, in one aspect, remedies the deficiencies of the prior art by providing an in vitro and or in vivo nanoscale, smart, biomolecular electronics element and or nano-electronics element, which elements may be employed in a scalable, intelligent, in vivo and or in vitro biomolecular electronics device platform and or a nano-electronics device platform, and which platform may also be comprised of one or more non-SBN elements and devices, such as crystals, conductors, insulators, semiconductors, MEMS, and circuits, but not limited to such, and further, which platform may also be coated in one or more surfactants and or cosurfactants and or metals, elements, materials and substances. A biomolecular device platform and or a nano-device platform according to the invention may be used, for example, in biomedical, electronics, telecommunications, and information processing applications, in vivo and or in vitro.

In one embodiment, one or more SBN structures, elements, and or platforms are used for in vivo and or in vitro biomolecular electronics and or nano-electronics. Biological molecules, particularly proteins and lipids are used to perform the basic properties necessary for the functioning of biomolecular electronic devices. These biological materials conduct current, transfer molecules from one location to another, are capable of major color changes on application of an electric field or light and can produce cascades that can be used for amplification of an optical or an electronic signal. All these properties can be applied to electronic switches, gates, storage devices, biosensors, biological transistors, to name just a few. In general, the electrical properties of bilayer lipid membranes are easily measurable for signal generation and transduction. Cells with intact plasma membranes can be considered to act as tiny capacitors under the influence of an electric field. Whereas sufficiently high field strength may increase the membrane potential past a critical point leading to the breakdown of the membrane, experimental care must be taken. (Dielectric breakdown of biological membrane occurs at about 1 volt across the membrane.) On the other hand, the use of electrostatic potentials around the lipid molecules is very attractive, because they are controllable.

In one illustrative embodiment, a cage 106 protein chain is created via a molecular bridge group. To align the SBN elements with respect to one another and with respect to an external magnetic or electrical field, one or more cage 100, cage 106, cargo elements 102a-102f, vesicle 110, bonded elements, and or cage 100-entrapped materials, substances, devices, biological and or chemical agents and or elements and in any combination are embedded in another material, like liquid crystal.

In one embodiment, one or more cage 100, cage 106, cargo elements 102a-102f, vesicle 110, bonded elements and or cage 100-entrapped materials, substances, devices, biological, and or chemical elements are coated completely or partially in metal.

In another SBN embodiment, one or more cage 100, cage 106, cargo elements 102a-102f, vesicle 110, bonded elements, and or cage 100-entrapped materials, substances, devices, biological and or chemical agents and or elements and in any combination are coated completely or partially in reflective and or non-reflective coatings.

In one embodiment, one or more cage 100, cage 106, cargo elements 102a-102f, vesicle 110, bonded elements, and or cage 100-entrapped materials, substances, devices, biological and or chemical agents and or elements and in any combination are used to coat completely or partially metals, crystals, insulators, conductors, semiconductor components, wires, and devices.

In another illustrative embodiment, one or more cage 100, cage 106, cargo elements 102a-102f, vesicle 110, bonded elements, and or cage 100-entrapped materials, substances, devices, biological and or chemical agents and or elements and in any combination facilitate in vivo and or in vitro the externally and or mechanistically directed alignment of, for example, but not limited to, biological elements, nanoparticles such as Fullerenes, but not limited to such, carbon nanotubes, crystals, conductors, semiconductors, insulators, and or other devices, materials and substances, which aligned assemblies may further be coated in one or more surfactants and or metals, elements, materials and substances.

In another illustrative embodiment, one or more cage 100, cage 106, cargo elements 102a-102f, vesicle 110, bonded elements, and or cage 100-entrapped materials, substances, devices, biological and or chemical agents and or elements and in any combination facilitate in vivo and or in vitro the automatic self-alignment of, for example, but not limited to, biological elements, nanoparticles such as Fullerenes, but not limited to, carbon nanotubes, crystals, conductors, semiconductors, insulators, and or other devices, materials and substances, which self-aligned assemblies may further be coated in one or more surfactants and or metals, elements, materials and substances.

In one embodiment, one or more cage 100, cage 106, cargo elements 102a-102f, vesicle 110, bonded elements, and or cage 100-entrapped materials, substances, devices, biological and or chemical agents and or elements and in any combination, include optical elements such as, but not limited to, optics; optoelectronic elements; photoelectric elements; photodetectors; and photosensitive elements, which optical elements may also be coated or treated in whole or in part with materials that affect their optical properties.

In one embodiment, one or more cage 100, cage 106, cargo elements 102a-102f, vesicle 110, bonded elements, and or cage 100-entrapped materials, substances, devices, biological and or chemical agents and or elements and in any combination include imaging elements and sensors, such as, but not limited to, CCDs and CMOS optical elements.

In another illustrative SBN embodiment, one or more cage 100, cage 106, cargo elements 102a-102f, vesicle 110, bonded elements, and or cage 100-entrapped materials, substances, devices, biological and or chemical agents and or elements and in any combination contain one or more weaponized elements or agents.

In another illustrative SBN embodiment, one or more cage 100, cage 106, cargo elements 102a-102f, vesicle 110, bonded elements, and or cage 100-entrapped materials, substances, devices, biological and or chemical agents and or elements and in any combination contain one or more anti-terrorism elements or agents.

In one SBN embodiment, one or more or more cage 100, cage 106 elements and or cargo elements 102a-102f have faceted geometry. In one configuration, one or more cage 100, cage 106 elements and or cargo elements 102a-102f have one or more internal or external surfaces or facets that face one or more opposing elements and structures having one or more corresponding facets or surfaces. In one configuration, one or more cage 100, cage 106, and or cargo elements 102a-102f have one or more internal or external surfaces or facets, which in vivo and or in vitro, physically and or functionally contact, receive, grip, bond (e.g., covalently and or non-covalently), immobilize and structurally order one or more SBN elements, and or non-SBN elements and structures known in the art that have complementary faceted surfaces. In one shape programming embodiment, which constitutes another form of self-directed, self-assembly, one or more faceted cage 100, cage 106, and or cargo elements 102a-102f, and or suitably faceted non-SBN elements form self-assembling, self-directing, self-aligning three-dimensional multi-layer structures, which structures may further be coated in one or more surfactants and or cosurfactants and or metals, elements, materials and substances. In another embodiment, biological control laws govern and facilitate the shape programming process, and or follow geometrically derived algorithms such as graphs and Lie algebras, including Clifford algebras.

In another SBN embodiment, insulative, self-assembled monolayers (SAMs/SPMs) comprised of one or more insulative empty cage 106 elements, cargo elements 102a-102f, vesicle 110 elements, bonded elements and or cage 100-entrapped materials, substances, devices, biological and or chemical agents and or elements form in vivo and or in vitro an insulative substrate for one or more electronic, electromagnetic, optoelectronic, optical, photonic, photoelectric, and or ferromagnetic-based elements, components and or systems, which may further be coated in one or more surfactants and or cosurfactants and or metals, elements, materials and substances.

In another illustrative SBN embodiment, one or more cage 106 elements and or cargo elements 102a-102f and or vesicle 110, bonded elements, and or cage 100-entrapped materials, substances, devices, biological and or chemical agents and or elements, including, for example, but not limited to, cells, proteins, peptides, other biological elements, empty cage Fullerenes, endohedral Fullerenes, carbon nanotubes, crystals, insulators, conductors, semiconductors, materials, substances, and devices, are positioned and attached in vivo and or in vitro via techniques known in the art to one or more specific sites on one or more SBN-formed SAMs/SPMs, which further may be coated in one or more surfactants and or cosurfactants and or metals, elements, materials and substances.

In another SBN embodiment, biological and or biochemical elements and processes such as covalent and non-covalent bonding, one or more peptides, proteins, DNA, antibodies, monoclonal antibodies, other biological elements, biological control laws, and or geometrically derived algorithms such as graphs and Lie algebras, including Clifford algebras, but not limited to, facilitate the in vivo and or in vitro positioning, attaching, and binding and of one or more SBN elements and one or more other elements, including, but not limited to, cells, liposomes, micelles, proteins, peptides, surfactants, and or cosurfactants, other treated biological elements, empty cage Fullerenes, endohedral Fullerenes, carbon nanotubes, crystals, devices, structures, conductors, insulators, and semiconductors, on one or more specific sites on one or more SBN SAM layers, which assembled sites may further be coated in one or more surfactants and or cosurfactants and or metals, elements, materials and substances.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements form in vivo and or in vitro electronic circuit components, such as, but not limited to, one or more resistors, insulators, capacitors, transformers, conductors, and or semiconductors.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements form in vivo and or in vitro one or more electronic circuits, which circuit may also be comprised of one or more other elements such as empty Fullerenes, endohedral Fullerenes, nanotubes, crystals, insulators, conductors, semiconductors, and or other materials, substances and devices, which circuits also may be coated in one or more surfactants and or cosurfactants and or other materials and substances.

In one SBN embodiment, one or more externally directed, and or self-directed cage 100, cage 106, cargo elements 102a-102f, vesicle 110, bonded elements, and or cage 100-entrapped materials, substances, devices, biological and or chemical agents and or elements are switched on or off and or change states in vivo and or in vitro by applying an electric field, and may also comprise one or more transistors in another embodiment.

In another embodiment, one or more cage 100, cage 106, cargo elements 102a-102f, vesicle 110, bonded elements, and or cage 100-entrapped materials, substances, devices, biological and or chemical agents and or elements and in any combination self-assemble, and or are shape-programmed, and or use biological control laws and or processes, and or use geometrically derived algorithms such as graphs and Lie algebras, including Clifford algebras, but not limited to, and or are mechanically assembled via lithography, and or utilize other externally directed techniques known the art, and or some combination thereof, to form in vivo and or in vitro positions that are associated with electronic circuits and or information processing devices, such as atomic and molecular scale device design, their interconnection, nanofabrication and circuit architectures.

According to one illustrative embodiment, one or more externally directed, and or self-directed cage 100, cage 106, cargo elements 102a-102f, vesicle 110, bonded elements, and or cage 100-entrapped materials, substances, devices, biological and or chemical agents and or elements are embedded and or incorporated into one or more materials, substances, and or agents.

According to one illustrative embodiment, one or more externally directed, and or self-directed cage 100, cage 106, cargo elements 102a-102f, vesicle 110, bonded elements, and or cage 100-entrapped materials, substances, devices, biological and or chemical agents and or elements are embedded and or incorporated into one or more devices, systems, organisms, and or mechanisms.

In another embodiment, molecular imprinting is utilized to form in vivo and or in vitro SBN element positions that are associated with circuits and or information processing devices, such as atomic and molecular scale device design, their interconnection, nanofabrication and circuit architectures, which circuits and devices are then used to implement an SBN molecular-imprint technology embodiment, wherein polymer or other suitable films may be used as a pliable template for the assembled elements. The assemblies are pressed into a film and then removed, leaving a physical mold of one or more SBN elements or 3-D assemblies. The film is then hardened and used to detect that particular SBN element and or 3-D assembly since their complex shape will bind only to that particular SBN element or assembly configuration. In one SBN embodiment, this process provides a molecular-level lithographic process for silicon VLSI (very large scale integration) production and produces circuits at feature sizes beyond the reach of current optical lithographic methods.

In another illustrative SBN embodiment, one or more externally directed, and or self-directed cage 100, cage 106, cargo elements 102a-102f, vesicle 110, bonded elements, and or cage 100-entrapped materials, substances, devices, biological and or chemical agents and or elements contain one or more magnetic nanoparticles.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are nanoscale recording memory media or components, which may incorporate metals, ferromagnetic materials, and or ferroelectric materials and elements, and or may form into magnetic rings, and or may form vertically polarized magnetic domains and or form magnetic domains on isolated islands.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are photovoltaic cells or components.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are batteries or components for storing electronic charge.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are an environmental hazard and or toxic screening component or system.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are an opto-electronic system or component.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are chemical, nuclear, and or biological sensors.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are a spin-based electronics system or component.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements exploit in vivo and or in vitro the Coulomb blockade-like properties of self-assembled proteins, wherein a single particle at a time may move through a transmembrane protein-based channel.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements utilize and or exploit in vivo and or in vitro the Casimir effect, which is a small attractive force that acts between two close parallel uncharged conducting elements. It is due to quantum vacuum fluctuations of the electromagnetic field.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements utilize and or exploit in vivo and or in vitro the Jahn-Teller effect. The Jahn-Teller theorem states that a nonlinear polyatomic system in the nuclear configuration with a degenerate electronic ground state is unstable. The system distorts itself spontaneously so that the electronic term splits and the ground state becomes nondegenerate. This Jahn-Teller effect may also occur for some ionic states of an icosahedral SBN. For example, the fullerene molecule, C60, has a very high symmetry, and a nondegenerate ground state. Because of high symmetry, however, fullerene ions, both negative and positive have a high orbital degeneracy, and are therefore good candidates. The same conditions may also be bioengineered into a very high symmetry icosahedral SBN. These characteristics are of invention interest partly because it appears that properties such as superconductivity (the resistance-less flow of electricity) in solids comprising loosely bound collections of symmetrical structures with a high orbital degeneracy are closely related to the structure of isolated ions.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements contain one or more information processing elements such as, for example, but not limited to, encoders and decoders, memory, logic gates, registers, circuits, wiring and connectors, input and output elements, analog to digital and digital to analog converters and system architectures known in the art.

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements modify, process, manipulate, encode and decode, input, output, transmit, communicate, store and read various forms and types of information using a variety of suitable techniques known in the art, in vivo and in vitro.

In some illustrative embodiments, one or more cage 100, cage 106, cargo elements 102a-102f, vesicle 110, bonded elements, and or cage 100-entrapped materials, substances, devices, biological and or chemical agents and or elements and in any combination are physically linked via molecular addends, but are not limited to such addend types. In one embodiment, one or more cage 100, cage 106, cargo elements 102a-102f, vesicle 110, bonded elements, and or cage 100-entrapped materials, substances, devices, biological and or chemical agents and or elements and in any combination are connectors for carrying information from a storage, processing or communications element or device to another.

In another SBN embodiment, an additive approach in nanofabrication may be employed in vitro using one or more shadow mask techniques whereby complex patterns such as rings and intersecting lines are readily produced on a framework, substrate, or a structure comprised of one or more cage 100, cage 106, cargo elements 102a-102f, vesicle 110, bonded elements, and or cage 100-entrapped materials, substances, devices, biological and or chemical agents and or elements and in any combination, and which framework, substrate, or a structure may also contain non-SBN elements.

The shadow masking technique allows for arbitrary two-dimensional writing with SBN molecules. The endohedral doping of one or more cage 100, cage 106, cargo elements 102a-102f, and or vesicle 110 allows for precise control of electronic properties, and the blending of doped/undoped SBN elements allows for control of electrical behavior from insulating (or poorly semiconducting) to metallic conduction. Combining endohedral doping with shadow mask writing, the actual composition of an SBN comprised nanowire may be tailored in situ during patterning. Hence within a single SBN comprised nanowire, insulating and metallic regions may be precisely defined: a one-dimensional junction engineering becomes realistic allowing for straightforward implementation of nanoscale logic gate concepts. Isolation of individual atoms within the SBN elements provides a stable environment for one or more atoms. Electrical manipulation in vivo and or in vitro of one or more atoms in the SBN elements may also be interpreted as one or more bits of information.

In one embodiment, one or more externally directed, and or self-directed cage 100, cage 106, cargo elements 102a-102f, vesicle 110, bonded elements, and or cage 100-entrapped materials, devices, substances, biological, and or chemical elements and or SBN platforms utilize and or employ one or more antennae as sensors and or for transmission of information in vivo and in vitro.

in other illustrative configurations, one or more cage 100, cage 106, cargo elements 102a-102f, vesicle 110, bonded elements, and or cage 100-entrapped materials, devices, substances, devices, biological and or chemical agents and or elements and or SBN platforms are functionally linked via photonic, chemical, electromagnetic, electrical and/or quantum (non-classical) interactions, including the Internet, to work and cooperate locally and/or remotely.

In another embodiment, one or more cage 100, cage 106, cargo elements 102a-102f, vesicle 110, bonded elements, and or cage 100-entrapped materials, devices, substances, biological and or chemical agents and or elements and or SBN platforms are assigned a unique address that may be addressed via appropriate means, for example, but not limited to, an Internet Protocol address, and or be integrated into a personal area network (PAN), local area network (LAN), and or a wide area network (WAN).

In one embodiment, one or more externally directed, and or self-directed cage 100, cage 106, cargo elements 102a-102f, vesicle 110, bonded elements, and or cage 100-entrapped materials, substances, devices, biological and or chemical agents and or elements are an in vitro and or in vivo nanoscale information processing element and or platform, which may also be coated in one or more surfactants and or cosurfactants or other materials and substances, and which processing element and or platform may also follow and execute algorithms expressed by or use biological control laws and or processes, and or geometrically derived algorithms such as graphs and Lie algebras, including Clifford algebras, but not limited to.

In one embodiment, one or more externally directed, and or self-directed cage 100, cage 106, cargo elements 102a-102f, vesicle 110, bonded elements, and or cage 100-entrapped materials, devices, substances, biological, and or chemical elements are an in vivo and or in vitro nanoscale information processing element and or platform that utilizes photons emitted by SBN Light Sources as the basis of computation.

In another embodiment, one or more externally directed, and or self-directed cage 100, cage 106, cargo elements 102a-102f, vesicle 110, bonded elements, and or cage 100-entrapped materials, substances, devices, biological and or chemical agents and or elements comprise a cognitive information processing element and or platform that follows and executes algorithms expressed by or use biological control laws and or processes, and or geometrically derived algorithms such as graphs and Lie algebras, including Clifford algebras, but not limited to.

In another embodiment, one or more externally directed, and or self-directed cage 100, cage 106, cargo elements 102a-102f, vesicle 110, bonded elements, and or cage 100-entrapped materials, substances, devices, biological and or chemical agents and or elements comprise a hybrid digital and analog information processing element and or platform, wherein enlisting the rich repertoire biochemical reactions and adopting a nested hierarchical organization makes intermixing of digital an analog processing possible in bio-computing applications.

According to one illustrative embodiment, one or more externally directed and or self-directed SBN information processing elements and or platforms comprise in vivo and or in vitro bio-nano-computer elements and or platforms that are programmable, and or autonomous acting, and or do cognitive processing, which bio-nano-computers may also be self-directing, self-replicating, self-adapting, self-repairing, self-regulating, and or self-regenerating, and which are used for applications at the cellular, molecular, and nanoscale level that may include, but are not limited to, biomedical imaging, sensors, diagnostic systems, assay systems, therapeutic systems, drug delivery systems, prosthetic systems, cybernetic systems, cellular-level nano-fabrication systems, and inter- and intra-cellular imaging, repair, and engineering systems, the monitoring, sensing, imaging, diagnosing, repairing, constructing, fabricating, and or controlling of organic and or inorganic elements, and which bio-nano-computer elements and or platforms also may utilize and leverage biological control laws, and or geometrically derived algorithms such as graphs and Lie algebras, including Clifford algebras, but not limited to, in the performance of their tasks.

Cage 100, cage 106, cargo elements 102a-102f, vesicle 110, bonded elements, and or cage 100-entrapped materials, substances, devices, biological and or chemical agents and or elements, including SBN platform embodiments, may be encapsulated, packaged, stored, and or incorporated using methods known in the art, including for example, but not limited to: catheters; injections, including intramuscular injections; syringes; droppers and bulbs; pills; intravenous means; oral means; anal means; capsules; nanocapsules; nanoparticles; nano-devices; prescriptions; hospital and medical supplies; dental supplies; non-prescriptions; medications; over the counter products and remedies; alternative medicine supplies, systems, products and devices; hair care products; splints, casts, walkers, crutches, canes, wheelchairs, and other ambulatory aids; natural foods; vitamin and mineral supplements; first aid products; emergency health care procedures, systems, devices, and products, including combat medicine; health care products; grafts; skin patches; bandages; adhesives; wraps; masks; markers; powders; granules; geriatric care products; pediatric care products; diagnostic devices, systems, and products; medical imaging devices, systems, and products; telemedicine devices, systems, and products; in vivo monitoring systems, products, systems, and devices; in vitro monitoring systems, products, systems, and devices; laundry products; chemical, nuclear and biological sensors; sensors; bio-sensors; environmental sensors; combat systems, clothing, uniforms, and protective gear; food preparation products; food testing and safety devices, systems, and products; food storage wraps, systems, devices, and products; water treatment devices, systems and products; waste storage, management, and treatment systems and products; sewerage systems and products; plumbing systems and products; bed and bath products; animal care and veterinary products; animal feed; animal slaughter systems and products; cooking products; cookware; forensic devices, systems and products; home and office cleaning products; home products; office products; personal products; industrial products; home and office care products; paper products; personal hygiene products; sexual hygiene and safety products; sexual reproduction devices, systems, and products; sexual arousal products and devices; dental and dental care products; oral hygiene products, devices, and systems; robotic products, systems and devices; cybernetic devices; jewelry; novelties; solvents; agro-products; plants; animals; vehicles; biologicals; chemicals; cells; tissue; organs; proteins; liposomes; phages; micelles; peptides; antibodies; monoclonal antibodies; DNA; RNA; IRNA; siRNA; RISC; cloning; human contact; microelectromechanical systems (MEMS) and other types of nanosystems; food utensils; tools; appliances; consumer electronics; paints and finishes; heating, ventilation and air conditioning systems; construction, building, home and office materials; water; milk; food and other edible or chewable substances and items; prostheses; food and drink additives and supplements; drinks; beverages; soaps; creams; ointments; salves; topical agents; cosmetics; beautifying agents; liquids; fluids; oils; gels; adhesives; aerosols; vapors; airborne methods; pumps; fragrances and perfumes; textiles; sporting and athletic goods and devices; physical work out and training systems, devices, and products; sports medicine systems, devices, and products; recreational products and gear; shoes, clothing, and apparel; eyewear; sprays; dyes; biological elements; organ transplants; implants; stents; prosthetic devices; artificial skin, blood, limbs, joints, bones, cells, eyes, organs, and other artificial body parts and biological elements; subcutaneous means; incisions; surgical means; and in-patient and out-patient medical procedures.

The above-described embodiments have been set forth to describe more completely and concretely the present invention, and are not to be construed as limiting the invention. It is further intended that all matter and the description and drawings be interpreted as illustrative and not in a limiting sense. That is, while various embodiments of the invention have been described in detail, other alterations, which will be apparent to those skilled in the prior art, are intended to be embraced within the spirit and scope of the invention.

In view of the foregoing, what is claimed is:

1. An isolated bio-nanoparticle element comprising
a cage element defining a cavity, up to 100 nanometers in diameter, formed from a plurality of self-assembling, purified Clathrin protein molecules and or purified coatomerI/II protein molecules and
one or more types of cargo elements located within the cavity,
wherein at least one of the elements, under the guidance of one or more types of externally and or self-directed methods, executes one or more types of functions and or effects one or more ends, in vivo and or in vitro.

2. An isolated bio-nanoparticle element according to claim 1, comprising one or more active and or passive methods for capturing and or positioning one or more types of cargo elements within the cavity.

3. An isolated bio-nanoparticle element according to claim 1, comprising cage and one or more methods for internally and or externally to functionalizing cage and or one or all or a subset of cargo elements.

4. An isolated bio-nanoparticle element according to claim 1, wherein cage and or one or all or a subset of cargo elements respond to one or more types of internal and or external stimuli.

5. An isolated bio-nanoparticle element according to claim 1, wherein the one or more types of cargo elements, we a plurality of cargo elements.

6. An isolated bio-nanoparticle element according to claim 1, comprising one or more types of coatings on part or the entirety of cage and or one or all or a subset of cargo elements.

7. An isolated bio-nanoparticle element according to claim 1, wherein cage, and or one or all or a subset of cargo elements, are physically and or functionally incorporated in whole or in part in one or more types of elements.

8. An isolated bio-nanoparticle element according to claim 1, wherein cage, and or one or all or a subset of cargo elements are stable and or viable for an approximate and or specified period of time.

9. An isolated bio-nanoparticle element according to claim 1, wherein the self-assembling plurality of protein molecules is comprised of Clathrin molecule, in whole or in part.

10. An isolated bio-nanoparticle element according to claim 1, wherein the self-assembling plurality of protein molecules is comprised of a coatomer I/II molecules, in whole or in part.

11. An isolated bio-nanoparticle element according to claim 1, wherein the cage is substantially greater than one nanometer in diameter.

12. An isolated bio-nanoparticle element according to claim 1, wherein the cage is at least about 50 nanometers in diameter.

13. An isolated bio-nanoparticle element according to claim 1, wherein the cage is at least about 100 nanometers in diameter.

14. An isolated bio-nanoparticle element according to claim 1, wherein the elements comprise a platform comprised of a plurality of isolated bio-nanoparticle elements each having a cage defining a cavity formed from a plurality of self-assembling purified protein molecules, and one or more cargo elements of one or more types located within the cavity, in vitro and or in vivo.

15. An isolated bio-nanoparticle element according to claim 1, wherein cage is empty and includes no cargo elements.

16. An isolated bio-nanoparticle element according to claim 1, wherein cage produces ordered scaffolding, creating self-assembling multi-layer structures having one or more dimensions.

17. An isolated bio-nanoparticle element according to claim 1, wherein cage, and or one or all or a subset of cargo elements, form non-permeable, permeable, and or semi-permeable cavities.

18. An isolated bio-nanoparticle element according to claim 1, wherein cage has icosahedral geometry.

19. An isolated bio-nanoparticle element according to claim 1, wherein cage and or one or all or a subset of the cargo elements are comprised of recombinant and or synthetic biological elements, in whole or in part.

20. An isolated bio-nanoparticle element according to claim 1, wherein cage and or one or all or a subset of the cargo elements effect one or more self-modifying behaviors and actions of one or more types.

21. An isolated bio-nanoparticle element according to claim 1, wherein cage inhibits charge transfer between cage and its enclosed cargo and or prevents cage distortion.

22. An isolated bio-nanoparticle element according to claim 1, wherein more than one bio-nanoparticle element is physically and or functionally linked together.

23. An isolated bio-nanoparticle element according to claim 1, wherein the one or more types of externally and or self directed methods, executing one or more types of functions comprise a plurality of methods and or functions.

24. An isolated bio-nanoparticle element according to claim 7, wherein, the incorporated elements comprise a plurality of elements, in vitro and or in vivo.

25. An isolated bio-nanoparticle element according to claim 14, wherein the plurality of cargo elements of a subset of the bin-nanoparticle elements are a plurality of cargo elements.

26. An isolated bio-nanoparticle-element according to claim 14, wherein, a plurality of bio-nanoparticle elements are physically and or functionally incorporated in whole or in part in one or more types of elements, in vitro and or in vivo.

27. An isolated bio-nanoparticle element according to claim 26, wherein, the incorporated elements comprise a plurality of element.

28. An method for forming an isolated bin-nanoparticle element comprising forming a cage defining a cavity, up to 100 nanometers in diameter, formed from a plurality of self-assembling purified Clathrin protein molecules and or purified coatomerI/II protein molecules and one or more types of cargo elements located within the cavity, and, wherein at least one of the elements, under the guidance of one or more externally and or self-directed methods, executes one or more functions and or effects one or more ends in vivo and or in vitro.

* * * * *